(12) United States Patent
Gijsen et al.

(10) Patent No.: US 8,524,757 B2
(45) Date of Patent: Sep. 3, 2013

(54) BENZIMIDAZOLE CANNABINOID AGONISTS BEARING A SUBSTITUTED HETEROCYCLIC GROUP

(75) Inventors: Henricus Jacobus Maria Gijsen, Beerse (BE); Michel Anna Jozef De Cleyn, Beerse (BE); Michel Surkyn, Beerse (BE); Bie Maria Pieter Verbist, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 985 days.

(21) Appl. No.: 12/307,512

(22) PCT Filed: Jul. 2, 2007

(86) PCT No.: PCT/EP2007/056619
§ 371 (c)(1),
(2), (4) Date: Jan. 5, 2009

(87) PCT Pub. No.: WO2008/003665
PCT Pub. Date: Jan. 10, 2008

(65) Prior Publication Data
US 2009/0312339 A1    Dec. 17, 2009

(30) Foreign Application Priority Data
Jul. 4, 2006    (EP) .................................... 06116564

(51) Int. Cl.
*A01N 43/52* (2006.01)
*A61K 31/415* (2006.01)
*C07D 231/56* (2006.01)

(52) U.S. Cl.
USPC ...................................... 514/394; 548/361.1

(58) Field of Classification Search
USPC ...................................... 548/361.1; 514/394
See application file for complete search history.

(56) References Cited

FOREIGN PATENT DOCUMENTS
JP          08272028         * 10/1996

OTHER PUBLICATIONS

Lietuvos TSR Mokslu Akademijos Darbai, Serija B: Chemija, Technika, Fizine Geografija (1974), (2), 61-7.*
Subasinghe, N.L. et al. "A Novel Series of Arylsulfonylthiophene-2-Carboxamidine Inhibitors of the Complement Component C1S", Bioorganic & Medicinal Chemistry Letters 16 (2006) 2200-2204.

* cited by examiner

*Primary Examiner* — Paul V. Ward
(74) *Attorney, Agent, or Firm* — Thomas J. Dodd

(57) ABSTRACT

The present invention is related to novel benzimidazole compounds of formula (I) having cannabinoid receptor agonistic properties, pharmaceutical compositions comprising these compounds, chemical processes for preparing these compounds and their use in the treatment of diseases linked to the mediation of the cannabinoid receptors in animals, in particular humans.

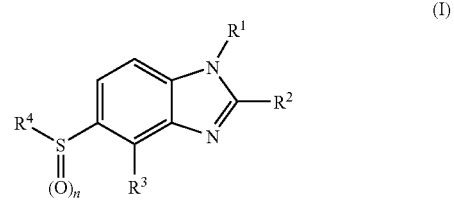

11 Claims, No Drawings

BENZIMIDAZOLE CANNABINOID AGONISTS BEARING A SUBSTITUTED HETEROCYCLIC GROUP

CROSS REFERENCE TO RELATED APPLICATIONS

This application is a national stage application of Pat. application Ser. No. PCT/EP2007/056619, filed Jul. 2, 2007 and EPO Patent Application No. 06116564.3, filed Jul. 4, 2006, all of which are hereby incorporated by reference in their entirety.

The present invention is related to novel benzimidazole compounds of formula (I) having selective cannabinoid receptor 2 agonistic properties, pharmaceutical compositions comprising these compounds, chemical processes for preparing these compounds and their use in the treatment of diseases linked to the mediation of the cannabinoid receptors in animals, in particular humans.

Classical cannabinoids such as the marijuana derived cannabinoid $\Delta^9$-tetrahydro-cannabinol, ($\Delta^9$-THC) produce their pharmacological effects via interaction with specific cannabinoid receptors in the body. So far, two cannabinoid receptors have been characterized: CB1, a receptor found in the mammalian brain and peripheral tissues and CB2, a receptor found predominantly in the peripheral tissues. Compounds that are agonists or antagonists for one or both of these receptors have been shown to provide a variety of pharmacological effects. There is considerable interest in developing cannabinoid analogs that have selective CB2 agonistic activity since it is believed high selectivity for CB2 receptor may offer avenues for harnessing the beneficial effect of CB receptor agonists while avoiding the central adverse events seen with cannabinoid structures (see e.g. Expert Opinion on Investigational Drugs (2005), 14(6), 695-703).

WO-2006/048754 discloses sulfonyl benzimidazole derivatives having CB2 agonistic activity.

The compounds of the present invention differ structurally from the cited art known compounds by the presence of a heterocyclic moiety on the sulfonyl group which is always substituted.

It was found the compounds of the present invention unexpectedly have a higher ratio of CB2 agonism over CB1 agonism than the cited art known compounds. Hence the compounds of the present invention are more selective CB2 agonists than the art known compounds from WO-2006/048754.

The present invention relates to novel compounds of formula (I)

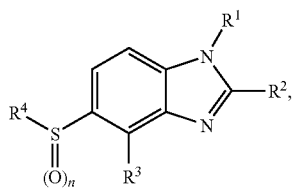

(I)

the pharmaceutically acceptable acid addition salts and the stereochemically isomeric forms thereof, wherein
n is an integer 1 or 2;
$R^1$ is $C_{2-6}$alkyl;
  $C_{1-6}$alkyl substituted with 1, 2 or 3 substituents each independently selected from halo, hydroxy, $C_{1-4}$alkyl, $C_{1-4}$alkyloxy, cyano, nitro, amino, and mono- or di($C_{1-4}$alkyl)amino;
  $C_{1-6}$alkyl substituted with a cyclic group selected from $C_{3-8}$cycloalkyl, oxo$C_{3-8}$cycloalkyl, $C_{5-8}$cycloalkenyl, bicyclo[2.2.1]hept-2-enyl, bicyclo[2.2.2]octanyl and bicyclo[3.1.1]heptanyl, wherein said cyclic group is optionally substituted with one or more substituents each independently selected from halo, hydroxy, $C_{1-4}$alkyl, $C_{1-4}$alkyloxy, cyano, nitro, $NR^5R^6$ or $CONR^5R^6$ wherein $R^5$ and $R^6$ are independently selected from hydrogen or $C_{1-4}$alkyl; or
  $C_{1-6}$alkyl substituted with a heterocycle selected from pyrrolidinyl, piperidinyl, homopiperidinyl, piperazinyl, morpholinyl, tetrahydrofuranyl, tetrahydropyranyl, 1,1-dioxo-tetrahydrothiopyranyl, [1,3]dioxolanyl, [1,4]dioxolanyl, [1,3]dioxanyl, 5-oxo-pyrrolidin-2-yl, or 2-oxo-oxepanyl; wherein said heterocycle is optionally substituted with one or two substituents each independently selected from $C_{1-4}$alkyl, polyhalo$C_{1-4}$alkyl, halo, hydroxy, $C_{1-4}$alkyloxy, cyano, trifluoromethyl, $COR^5$, $COOR^5$, $CONR^5R^6$, $SO_2R^5$ wherein $R^5$ and $R^6$ are independently selected from hydrogen or $C_{1-4}$alkyl or polyhalo$C_{1-4}$alkyl;
$R^2$ is $C_{2-6}$alkyl;
  $C_{1-6}$alkyl substituted with 1, 2 or 3 substituents each independently selected from halo, hydroxy, $C_{1-4}$alkyl, $C_{3-6}$cycloalkyl, $C_{1-4}$alkyloxy, polyhalo$C_{1-4}$alkyloxy, trifluoromethyl, cyano, nitro, $NR^7R^8$, $CONR^7R^8$, or $NHCOR^7$ wherein $R^7$ and $R^8$ are independently selected from hydrogen, $C_{1-4}$alkyl or polyhalo$C_{1-4}$alkyl;
  $C_{3-6}$alkenyl;
  $C_{3-6}$alkynyl;
  $C_{3-6}$cycloalkyl; or
  cyclic group selected from pyrrolidininyl, piperidinyl, piperazinyl, morpholinyl, tetrahydrofuranyl, tetrahydropyranyl, [1,3]dioxolanyl, [1,3]dioxanyl, [1,4]dioxanyl, 5-oxo-pyrrolidin-2-yl, bicyclo[2.2.1]hept-2-enyl, and bicyclo[3.1.1]heptanyl; wherein said cyclic group is optionally substituted with one or two substituents each independently selected from $C_{1-4}$alkyl, halo, hydroxy, $C_{1-4}$alkyloxy, or trifluoromethyl;
$R^3$ is hydrogen, halo, $C_{1-4}$alkyl, $C_{1-4}$alkyloxy, trifluoromethyl or cyano;
$R^4$ is heteroaryl;
heteroaryl is selected from N-oxy-pyridinyl, N-oxy-pyridazinyl, N-oxy-pyrimidinyl or N-oxy-pyrazinyl; or
  selected from furanyl, thiophenyl, pyrrolyl, pyrazolyl, imidazolyl, isoxazolyl, thiazolyl, triazolyl, tetrazolyl, isothiazolyl, thiadiazolyl, oxadiazolyl, pyridinyl, pyridazinyl, pyrimidinyl, pyrazinyl, triazinyl, N-oxy-pyridinyl, N-oxy-pyridazinyl, N-oxy-pyrimidinyl, N-oxy-pyrazinyl or 2-oxo-1,2-dihydro-pyridinyl, each substituted with 1, 2 or 3 substituents each independently selected from halo; hydroxy; $C_{1-4}$alkyl; $C_{3-6}$cycloalkyl; $C_{2-6}$alkenyl; $C_{2-6}$alkenyl substituted with 1 or 2 substituents selected from halo; $C_{2-6}$alkynyl; $C_{2-6}$alkynyl substituted with $C_{1-4}$alkyloxy; $C_{1-4}$alkyloxy; $C_{1-4}$alkyloxy$C_{1-4}$alkyl; polyhalo$C_{1-4}$alkyl; polyhalo$C_{1-4}$alkyloxy; cyano; nitro; $NR^9R^{10}$; $R^{11}$-carbonyl; $R^{11}$—$SO_2$—; $C_{1-4}$alkyl substituted with hydroxy, $NR^9R^{10}$, $R^{11}$-carbonyl or $R^{11}$—$SO_2$—; oxadiazolyl optionally substituted with $C_{1-4}$alkyl, polyhalo$C_{1-4}$alkyl or $C_{3-6}$cycloalkyl; dioxolanyl optionally substituted with 1 or 2 $C_{1-4}$alkyl; $C_{1-4}$alkyloxy substituted with hydroxy, $C_{1-4}$alkyloxy, $C_{1-4}$alkylcarbonylamino, $C_{1-4}$alkyloxycarbonylamino, amino, di($C_{1-4}$alkyl) amino or morpholinyl; $C_{1-4}$alkylcarbonylamino $C_{1-4}$alkylamino; $C_{1-4}$alkyloxy$C_{1-4}$alkylamino;

wherein $R^9$ and $R^{10}$ are independently from another selected from hydrogen, $C_{1-4}$alkyl, polyhalo$C_{1-4}$alkyl, aminosulfonyl, or $C_{1-8}$alkylsulfonyl; or $R^{11}$-carbonyl;

wherein $R^9$ and $R^{10}$ are taken together with the nitrogen atom bearing $R^9$ and $R^{10}$ may form a pyrrolidinyl, piperidinyl, piperazinyl or morpholinyl ring; and wherein $R^{11}$ is $C_{1-4}$alkyl, $C_{1-4}$alkyloxy, hydroxy, amino, mono- or di-($C_{1-4}$alkyl)amino, (hydroxy$C_{1-4}$alkyl) amino, ($C_{1-4}$alkyloxy$C_{1-4}$alkyl)amino, di($C_{1-4}$alkyl) amino$C_{1-4}$alkyl, pyrrolidinyl, piperidinyl, morpholinyl, N-methyl-piperazinyl, or $C_{1-4}$alkyl substituted with hydroxy, $C_{1-4}$alkyloxy, trifluoromethyl, $C_{1-4}$alkyloxy$C_{1-4}$alkyl, pyrrolidinyl, piperidinyl, morpholinyl, N-methyl-piperazinyl, or 2-oxo-imidazolidin-1-yl.

As used in the foregoing definitions:

halo is generic to fluoro, chloro, bromo and iodo;

$C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;

$C_{1-6}$alkyl is meant to include $C_{1-4}$alkyl and the higher homologues thereof having 5 or 6 carbon atoms, such as, for example, 2-methylbutyl, pentyl, hexyl and the like;

$C_{2-6}$alkyl defines straight and branched chain saturated hydrocarbon radicals having from 2 to 6 carbon atoms such as, for example, ethyl, propyl, butyl, 1-methylethyl, 2-methylpropyl 2-methylbutyl, pentyl, hexyl and the like;

$C_{1-8}$alkyl is meant to include $C_{1-6}$alkyl and the higher homologues thereof having 7 to 8 carbon atoms, such as for instance heptyl, ethylhexyl, octyl, and the like;

polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like;

$C_{2-6}$alkenyl defines straight and branched chain hydrocarbon radicals containing one double bond and having from 2 to 6 carbon atoms such as, for example, ethenyl, 2-propenyl, 3-butenyl, 2-butenyl, 2-pentenyl, 3-pentenyl, 3-methyl-2-butenyl, 3-hexenyl, 2-hexenyl and the like;

$C_{3-6}$alkenyl defines straight and branched chain hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl, 3-hexenyl, 2-hexenyl and the like;

$C_{2-6}$alkynyl defines straight and branched chain hydrocarbon radicals containing one triple bond and having from 2 to 6 carbon atoms such as, for example, ethynyl, 2-propynyl, 3-butynyl, 2-butynyl, 2-pentynyl, 3-pentynyl, 3-methyl-2-butynyl, 3-hexynyl, 2-hexynyl and the like;

$C_{3-6}$alkynyl defines straight and branched chain hydrocarbon radicals containing one triple bond and having from 3 to 6 carbon atoms such as, for example, 2-propynyl, 3-butynyl, 2-butynyl, 2-pentynyl, 3-pentynyl, 3-methyl-2-butynyl, 3-hexynyl, 2-hexynyl and the like;

$C_{3-6}$cycloalkyl is generic to cyclopropyl, cyclobutyl, cyclopentyl, and cyclohexyl;

$C_{3-8}$cycloalkyl is generic to cyclopropyl, cyclobutyl, cyclopentyl, cyclohexyl, cycloheptyl and cyclooctyl;

$C_{6-8}$cycloalkyl is generic to cyclohexyl, cycloheptyl and cyclooctyl;

$C_{5-8}$cycloalkenyl is generic to cyclopentenyl, cyclohexenyl, cycloheptenyl and cyclooctenyl.

The pharmaceutically acceptable acid addition salts as mentioned hereinabove are meant to comprise the therapeutically active non-toxic acid addition salt forms which the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular complex comprising a compound of the invention and one or more pharmaceutically acceptable solvent molecules, e.g. ethanol. The term 'hydrate' is used when said solvent is water.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy, the keto-form may be the mainly populated tautomer.

In the framework of this application, with the expression "a compound according to the invention" it is also meant to include a compound according to the general formula (I) and a pro-drug thereof, or a isotopically labelled compound thereof.

Also within the scope of the invention are so-called "pro-drugs" of the compounds of formula (I). Pro-drugs are certain derivatives of pharmaceutically active compounds which may have little or no pharmacological activity themselves which can, when administered into or onto the body, be converted into compounds of formula (I) having the desired pharmaceutical activity, e.g. by hydrolytic cleavage. Such derivatives are referred to as "pro-drugs".

In an embodiment, the present invention relates to compounds of formula (I) wherein wherein n is an integer 1 or 2;

$R^1$ is $C_{2-6}$alkyl;

$C_{1-6}$alkyl substituted with 1, 2 or 3 substituents each independently selected from halo, hydroxy, $C_{1-4}$alkyl, $C_{1-4}$alkyloxy, cyano, nitro, amino, and mono- or di($C_{1-4}$alkyl)amino;

$C_{1-6}$alkyl substituted with a cyclic group selected from $C_{3-8}$cycloalkyl, $C_{5-8}$cycloalkenyl, bicyclo[2.2.1]hept-2-enyl, bicyclo[2.2.2]octanyl and bicyclo[3.1.1]heptanyl, wherein said cyclic group is optionally substituted with one or more substituents each independently selected from halo, hydroxy, $C_{1-4}$alkyl, $C_{1-4}$alkyloxy, cyano, nitro, $NR^5R^6$ or $CONR^5R^6$ wherein $R^5$ and $R^6$ are independently selected from hydrogen or $C_{1-4}$alkyl; or $C_{1-6}$alkyl substituted with a heterocycle selected from pyrrolidinyl, piperidinyl, homopiperidinyl, piperazinyl, morpholinyl, tetrahydrofuranyl, tetrahydropyranyl, 1,1-dioxo-tetrahydrothiopyranyl, [1,3]dioxolanyl, [1,4]dioxanyl, [1,3]dioxanyl, 5-oxo-pyrrolidin-2-yl; wherein said heterocycle is optionally substituted with one or two substituents each independently selected from $C_{1-4}$alkyl, polyhalo$C_{1-4}$alkyl, halo, hydroxy, $C_{1-4}$alkyloxy, cyano, trifluoromethyl, $COR^5$, $COOR^5$, $CONR^5R^6$, $SO_2R^5$ wherein $R^5$ and $R^6$ are independently selected from hydrogen or $C_{1-4}$alkyl or polyhalo $C_{1-4}$alkyl;

$R^2$ is $C_{2-6}$alkyl;

$C_{1-6}$alkyl substituted with 1, 2 or 3 substituents each independently selected from halo, hydroxy, $C_{1-4}$alkyl, $C_{3-6}$cycloalkyl, $C_{1-4}$alkyloxy, polyhalo$C_{1-4}$alkyloxy, trifluoromethyl, cyano, nitro, $NR^7R^8$, $CONR^7R^8$, or $NHCOR^7$ wherein $R^7$ and $R^8$ are independently selected from hydrogen, $C_{1-4}$alkyl or polyhalo$C_{1-4}$alkyl;

$C_{3-6}$alkenyl;

$C_{3-6}$alkynyl;

$C_{3-6}$cycloalkyl; or cyclic group selected from pyrrolidininyl, piperidinyl, piperazinyl, morpholinyl, tetrahydrofuranyl, tetrahydropyranyl, [1,3]dioxolanyl, [1,3]dioxanyl, [1,4]dioxanyl, 5-oxo-pyrrolidin-2-yl, bicyclo[2.2.1]hept-2-enyl, and bicyclo[3.1.1]heptanyl; wherein said cyclic group is optionally substituted with one or two substituents each independently selected from $C_{1-4}$alkyl, halo, hydroxy, $C_{1-4}$alkyloxy, or trifluoromethyl;

$R^3$ is hydrogen, halo, $C_{1-4}$alkyl, $C_{1-4}$alkyloxy, trifluoromethyl or cyano;

$R^4$ is heteroaryl;

heteroaryl is selected from N-oxy-pyridinyl, N-oxy-pyridazinyl, N-oxy-pyrimidinyl or N-oxy-pyrazinyl; or selected from furanyl, thiophenyl, pyrrolyl, pyrazolyl, imidazolyl, isoxazolyl, thiazolyl, triazolyl, tetrazolyl, isothiazolyl, thiadiazolyl, oxadiazolyl, pyridinyl, pyridazinyl, pyrimidinyl, pyrazinyl, triazinyl, N-oxy-pyridinyl, N-oxy-pyridazinyl, N-oxy-pyrimidinyl or N-oxy-pyrazinyl, each substituted with 1, 2 or 3 substituents each independently selected from halo; hydroxy; $C_{1-4}$alkyl; $C_{3-6}$cycloalkyl; $C_{2-6}$alkenyl; $C_{2-6}$alkynyl; $C_{1-4}$alkyloxy; $C_{1-4}$alkyloxy$C_{1-4}$alkyl; polyhalo$C_{1-4}$alkyl; polyhalo$C_{1-4}$alkyloxy; cyano; nitro; $NR^9R^{10}$; $R^{11}$-carbonyl; $R^{11}$—$SO_2$—; $C_{1-4}$alkyl substituted with hydroxy, $NR^9R^{10}$, $R^{11}$-carbonyl or $R^{11}$—$SO_2$—; oxadiazolyl optionally substituted with $C_{1-4}$alkyl, polyhalo$C_{1-4}$alkyl or $C_{3-6}$cycloalkyl; or dioxolanyl optionally substituted with 1 or 2 $C_{1-4}$alkyl;

wherein $R^9$ and $R^{10}$ are independently from another selected from hydrogen, $C_{1-4}$alkyl, polyhalo$C_{1-4}$alkyl, aminosulfonyl, or $C_{1-8}$alkylsulfonyl; or $R^{11}$-carbonyl;

wherein $R^9$ and $R^{10}$. are taken together with the nitrogen atom bearing $R^9$ and $R^{10}$ may form a pyrrolidinyl, piperidinyl, piperazinyl or morpholinyl ring; and wherein $R^{11}$ is $C_{1-4}$alkyl, hydroxy, amino, mono- or di-($C_{1-4}$alkyl)amino, (hydroxy$C_{1-4}$alkyl)amino, ($C_{1-4}$alkyloxy$C_{1-4}$alkyl)amino, di($C_{1-4}$alkyl)amino $C_{1-4}$alkyl, pyrrolidinyl, piperidinyl, morpholinyl, N-methyl-piperazinyl, or $C_{1-4}$alkyl substituted with hydroxy, $C_{1-4}$alkyloxy, $C_{1-4}$alkyloxy$C_{1-4}$alkyl, trifluoromethyl, pyrrolidinyl, piperidinyl, morpholinyl, N-methyl-piperazinyl, or 2-oxo-imidazolidin-1-yl.

Interesting compounds of formula (I) are those compounds of formula (I) wherein one or more of the following restrictions apply a) n is an integer 1, or n is an integer 2; or
b) $R^1$ is $C_{1-6}$alkyl substituted with a cyclic group selected from $C_{3-8}$cycloalkyl; or
c) $R^1$ is $C_{1-6}$alkyl substituted with a heterocycle selected from tetrahydropyranyl; or
d) $R^2$ is $C_{1-6}$alkyl, in particular $R^2$ is tert-butyl or —$CH_2$-tert-butyl; or
e) $R^3$ is hydrogen; or
f) $R^4$ is N-oxy-pyridinyl; or
g) $R^4$ is furanyl, thiophenyl, oxadiazolyl, pyridinyl, or pyridazinyl; each substituted with 1, 2 or 3 substituents each independently selected from halo; hydroxy; $C_{1-4}$alkyl; $C_{1-4}$alkyloxy; polyhalo$C_{1-4}$alkyl; polyhalo $C_{1-4}$alkyloxy; cyano; $NR^9R^{10}$; $R^{11}$-carbonyl; $R^{11}$—$SO_2$—; or oxadiazolyl optionally substituted with $C_{1-4}$alkyl; wherein $R^9$ and $R^{10}$ are independently from another selected from hydrogen or $R^{11}$-carbonyl; and wherein $R^{11}$ is $C_{1-4}$alkyl, amino, or morpholinyl.

In an embodiment, the present invention relates to those compounds of formula (I), the N-oxides, the pharmaceutically acceptable acid addition salts and the stereochemically isomeric forms thereof, wherein n is an integer 1 or 2; $R^1$ is $C_{1-6}$alkyl substituted with $C_{3-8}$cycloalkyl or tetrahydropyranyl; $R^2$ is $C_{1-6}$alkyl; $R^3$ is hydrogen; $R^4$ is N-oxy-pyridinyl, or $R^4$ is furanyl, thiophenyl, oxadiazolyl, pyridinyl, or pyridazinyl; each substituted with 1, 2 or 3 substituents each independently selected from halo; hydroxy; $C_{1-4}$alkyl; $C_{1-4}$alkyloxy; polyhalo$C_{1-4}$alkyl; polyhalo$C_{1-4}$alkyloxy; cyano; $NR^9R^{10}$; $R^{11}$-carbonyl; $R^{11}$—$SO_2$—; or oxadiazolyl optionally substituted with $C_{1-4}$alkyl; wherein $R^9$ and $R^{10}$ are independently from another selected from hydrogen or $R^{11}$-carbonyl; and wherein $R^{11}$ is $C_{1-4}$alkyl, amino, or morpholinyl.

Compounds of formula (I-a), defined as compounds of formula (I) wherein n represents 1, and compounds of formula (I-b), defined as compounds of formula (I) wherein n represents 2, can be prepared by art known S-oxidation of intermediates (A).

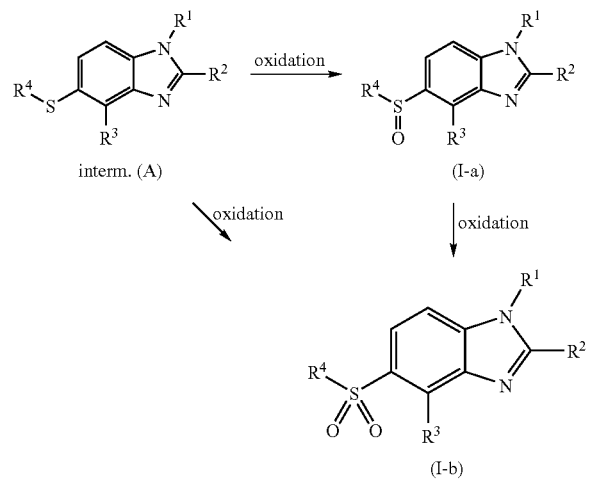

S-oxidation reactions can be performed using a 30% aqueous solution of hydrogen peroxide, or by other oxidizing agents such as, $NaIO_4$, tert-butyloxychloride, acyl nitrites, sodium perborate and peracids such as mCPBA (meta-chloroperbenzoic acid). Sulfides can be oxidized to sulfoxides which can be further oxidized to sulfones by addition of another equivalent of hydrogen peroxide, $KMnO_4$, sodium perborate, potassium hydrogen persulfate, mCPBA or the like reagents. If enough oxidizing agent is present, sulfides can be converted directly to sulfones without isolation of the sulfoxides.

Compounds of formula (I-b), defined as compounds of formula (I) wherein n is 2, can be prepared as described in Scheme 1.

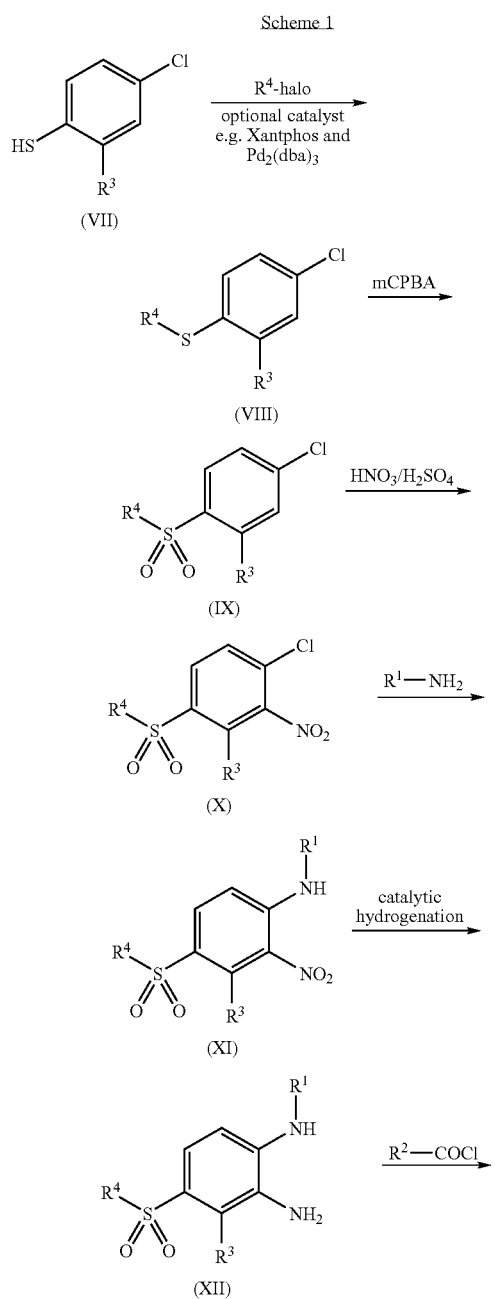

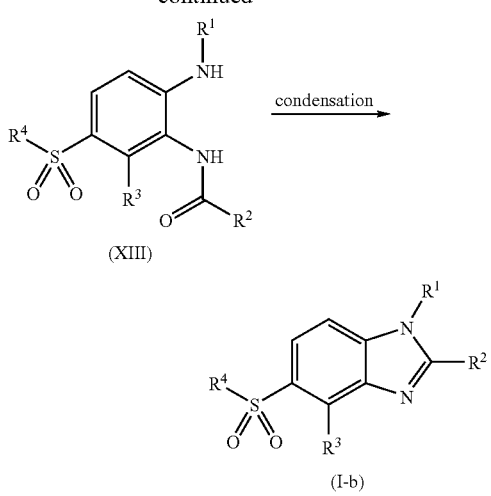

The condensation reaction for obtaining compounds of formula (I-b) can be performed under acidic or basic conditions. Under acidic conditions, the condensation is done in the presence of an organic acid such as acetic acid, or an inorganic acid such as HCl or $H_2SO_4$, or a combination thereof, in a solvent such as acetic acid, $H_2O$, methanol, ethanol, dioxane, toluene, or dichloroethane. Under basic conditions, the condensation reaction is performed in the presence of an inorganic base such as e.g. $K_2CO_3$ in a reaction-inert solvent such as DMSO, or in an alcoholic NaOH solution The reaction may conveniently be carried out at a temperature ranging between room temperature and the reflux temperature of the reaction mixture. Reaction rate and yield may be enhanced by microwave assisted heating e.g. at 190° C. in dichloroethane as solvent, possibly eliminating the need of an additionally added acid or base.

Intermediates (A) can be prepared as set out below in Scheme 2.

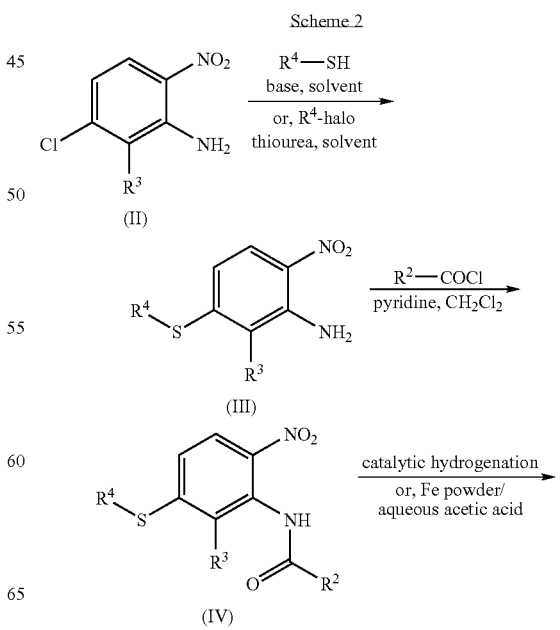

-continued

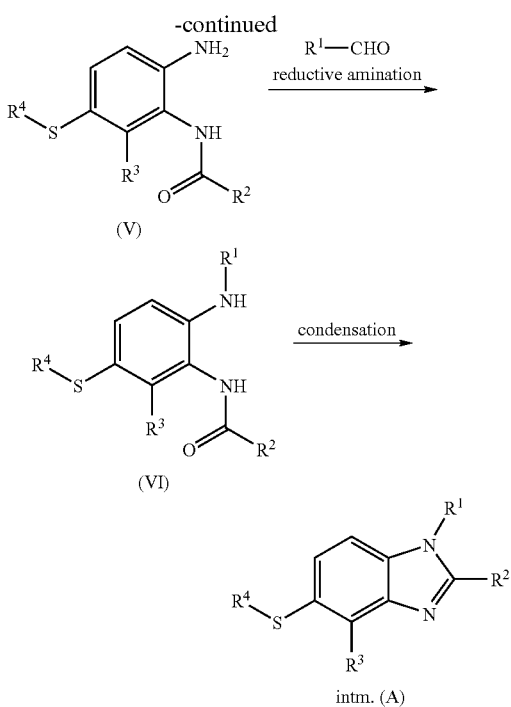

The condensation reaction to obtained an intermediate of formula (A) can be performed under similar conditions as described in Scheme 1 for obtaining compounds of formula (I-b).

Intermediates (A) can also be prepared by reacting intermediate (XVI) with the intermediate (XV), wherein L is a leaving group such as halo, methanesulfonyloxy, benzenesulfonyloxy, trifluoromethanesulfonyloxy and the like reactive leaving groups, in the presence of a suitable base such as $Cs_2CO_3$ in a reaction-inert solvent such as e.g. 2-propanone or dioxane. Depending upon the type of substituents present in intermediate (XV) it may be necessary to introduce protecting groups in intermediate (XV) which can be removed after the coupling reaction. The reaction may also be performed in the presence of a catalyst such as $Pd_2(dba)_3$ and a suitable ligand such as Xantphos.

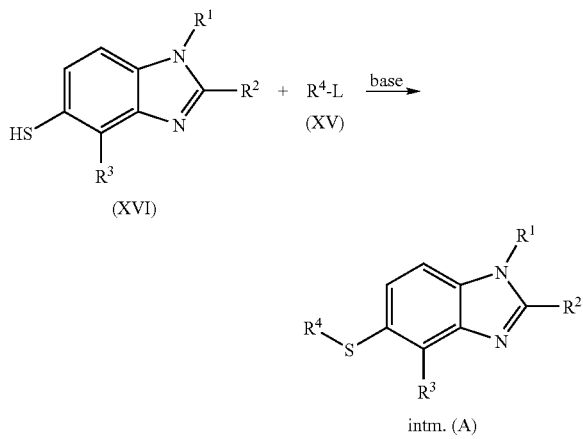

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof possess selective cannabinoid recepter 2 (CB2) agonistic properties as demonstrated in the Pharmacological Examples. Pharmacological example C.1 describes the methodology to measure CB1 and CB2 agonism and the ratio of CB2 agonism over CB1 agonism is listed in Table C.1.

Therefore the present compounds of formula (I) are useful as a medicine especially in the treatment of a condition or disease mediated by the cannabinoid 2 receptor, in particular CB2 agonistic activity. Subsequently the present compounds may be used for the manufacture of a medicine for treatment of a condition or a disease mediated by CB2 receptor activity, in particular CB2 agonistic activity.

Preferably, the present invention also provides the use of a compound of formula (I) or a pharmaceutically acceptable salt thereof for the manufacture of a medicament for the treatment of conditions or diseases selected from CB2 conditions or diseases.

Further, the present invention provides a method of treatment of a condition mediated by CB2 receptor activity, in a mammalian subject, which comprises administering to a mammal in need of such treatment a therapeutically effective amount of a compound of formula (I) or a pharmaceutically acceptable salt thereof.

Cannabinoid receptor 2 mediated conditions or disorders are e.g. cardiovascular diseases, such as e.g. atherosclerosis, hypertension, myocardial ischemia; chronic pain disorders, such as e.g. hyperalgesia, neuropathic pain, peripheral pain, visceral pain, inflammatory pain, thermal hyperalgesia, nociceptive pain, fibromyalgia, chronic low back pain, and dental pain; inflammation, oedema, bladder inflammation, neuroinflammatory diseases, immune system disorders, autoimmune diseases, multiple sclerosis, rheumatoid arthritis, gastrointestinal disorders, intestinal motility disorders, irritable bowel syndrome (IBS), inflammatory bowel disease (IBD), Crohn's disease, chronic liver injury (cirrhosis), cancer, prostate cancer, cancer pain, glioma, allergy, nausea and vomiting, asthma, chronic obstructive pulmonary diseases, psoriasis, epilepsy, and bone loss disorders, such as e.g., osteoporosis (hereinafter, referred as 'CB2 disorders or diseases').

The term "treating" and "treatment", as used herein, refers to curative, palliative and prophylactic treatment, including reversing, alleviating, inhibiting the progress of, or preventing the disease, disorder or condition to which such term applies, or one or more symptoms of such disease, disorder or condition.

The compounds of the present invention may show less toxicity, good absorption, distribution, good solubility, less protein binding affinity other than CB2 receptor, and less drug-drug interaction by reduced interaction with CYP3A4 en 2D6.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the cannabinoid receptors will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible increase or decrease in stimulation of cannabinoid receptors.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

EXPERIMENTAL PART

In the procedures described hereinafter the following abbreviations were used: 'DCM' means dichloromethane; 'DMF' means N,N-dimethyl-formamide; 'THF' means tetrahydrofuran; 'DIPE' means diisopropylether, 'DMF' means N,N-dimethyl-formamide, 'DMSO' means dimethyl sulfoxide 'NaBH$_3$(CN)' means sodium cyanotrihydroborate, 'mCPBA' means 3-chlorobenzenecarboperoxoic acid, 'Cs$_2$CO$_3$' means cesium carbonate, 'MgSO$_4$' means magnesium sulphate, 'NaHCO$_3$' means carbonic acid monosodium salt, 'NaBH$_4$' means sodium tetrahydroborate(−1), 'Na$_2$SO$_4$' means sodium sulfate, 'NH$_4$Cl' means ammonium chloride, 'K$_2$CO$_3$' means potassium carbonate, 'NH$_4$HCO$_3$' means carbonic acid mono-ammonium salt, 'NaOH' means sodium hydroxide, 'NaCl' stands for sodium chloride, 'NaHCO$_3$' means sodium hydrogen carbonate, 'Pd$_2$(dba)$_3$' means tris[μ-[(1,2-η:4,5-η)-(1E,4E)-1,5-diphenyl-1,4-pentadien-3-one]] dipalladium, 'Xantphos' means (9,9-dimethyl-9H-xanthene-4,5-diyl)bis[diphenylphosphine], 'TFA' means trifluoroacetic acid, 'Et$_3$N' means triethylamine, 'EtOAc' means ethyl acetate, 'CH$_3$OH' means methanol, 'PPTS' means pyridinium p-toluenesulfonate and 'PS' means polystyrene.

Isolute HM-N™ filter is a product of Argonaut, Foster City, Calif. 94404, USA, and is a short column comprising a modified form of diatomaceous earth that can remove water from a sample in combinatorial chemistry applications. Extrelut™ is a product of Merck KgaA, Darmstadt, Germany, and is a short column comprising diatomaceous earth.

For some compounds that were purified by reversed phase high-performance liquid chromatography (HPLC) the used method is described below (indicated in the compound procedure with HPLC method A, HPLC method B, HPLC method C).

When necessary, these methods can be slightly adjusted by a person skilled in the art to obtain a more optimal result for the separation.

HPLC Method A

The product was purified by reversed-phase high-performance liquid chromatography (Shandon Hyperprep® C18 BDS (Base Deactivated Silica) 8 μm, 250g, I.D. 5 cm). Three mobile phases were used (phase A: a 0.25% NH$_4$HCO$_3$ solution in water; phase B: CH$_3$OH; phase C: CH$_3$CN). First, 75% A and 25% B with a flow rate of 40 ml/min was hold for 0.5 minutes. Then a gradient was applied to 50% B and 50% C in 41 minutes with a flow rate of 80 ml/min. Then a gradient was applied to 100% C in 20 minutes with a flow rate of 80 ml/min and hold for 4 minutes.

HPLC Method B

The product was purified by reversed-phase high-performance liquid chromatography (Shandon Hyperprep® C18 BDS (Base Deactivated Silica) 8 μm, 250 g, I.D. 5 cm). Three mobile phases were used (phase A: a 0.25% NH$_4$HCO$_3$ solution in water; phase B: CH$_3$OH; phase C: CH$_3$CN). First, 75% A and 25% B with a flow rate of 40 ml/min was hold for 0.5 minutes. Then a gradient was applied to 100% B in 41 minutes with a flow rate of 80 ml/min. Then a gradient was applied to 100% C in 20 minutes with a flow rate of 80 ml/min and hold for 4 minutes.

HPLC Method C

The product was purified by reversed-phase high-performance liquid chromatography (Shandon Hyperprep® C18 BDS (Base Deactivated Silica) 8 μm, 250g, I.D. 5 cm). Two mobile phases were used (phase A: a 0.25% NH$_4$HCO$_3$ solution in water; phase B: CH$_3$CN). First, 85% A and 15% B with a flow rate of 40 ml/min was hold for 0.5 minutes. Then a gradient was applied to 10% A and 90% B in 41 minutes with a flow rate of 80 ml/min. Then a gradient was applied to 100% C in 20 minutes with a flow rate of 80 ml/min and hold for 4 minutes.

A. Synthesis of the Intermediates

EXAMPLE A.1 a) Preparation of

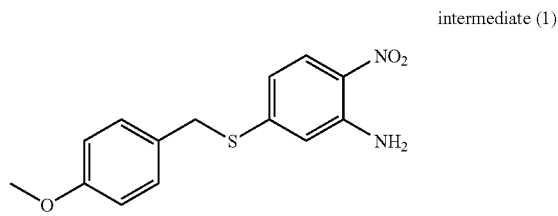 [SMILES: COc1ccc(CSc2ccc([N+](=O)[O-])c(N)c2)cc1]

intermediate (1)

A mixture of 5-chloro-2-nitrobenzenamine (0.16 mol), 4-methoxybenzenemethanethiol (0.16 mol) and potassium hydroxide (0.30 mol) in ethanol (500 ml) was stirred and refluxed for 2 hours. The reaction mixture was cooled. The precipitate was filtered off, washed with ethanol and dried, yielding 48.5 g of intermediate (1).

b) Preparation of

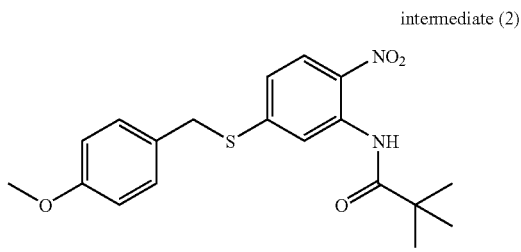 [SMILES: COc1ccc(CSc2ccc([N+](=O)[O-])c(NC(=O)C(C)(C)C)c2)cc1]
intermediate (2)

2,2-Dimethylpropanoyl chloride (0.14 mol) was added dropwise to a mixture of intermediate (1) (0.125 mol) and pyridine (500 ml). The reaction mixture was stirred and refluxed for 2 hours. The reaction mixture was cooled and the solvent was evaporated. The residue was taken up into DCM and washed with water. The organic layer was separated, dried, filtered and the solvent was evaporated. The residue was crystallized from DIPE with a drop of hexane. The precipitate was filtered off, washed and dried, yielding 28.9 g of intermediate (2).

c) Preparation of

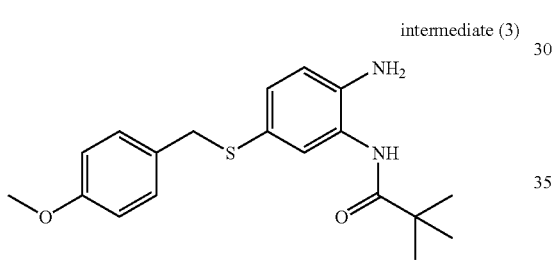
intermediate (3)

A mixture of intermediate (2) (0.0748 mol), Fe powder (56 g) and acetic acid (10 ml) in water (500 ml) was stirred and refluxed for 4 hours. The mixture was cooled. The solvent was decanted. The residue was taken up into methanol and THF. The mixture was filtered over diatomite. The solvent was evaporated. The residue was taken up into DCM. The organic layer was separated and filtered over MgSO$_4$ and diatomite. The solvent was evaporated. The residue was crystallized from DIPE. The precipitate was filtered off and dried, yielding 21g of intermediate (3).

d) Preparation of

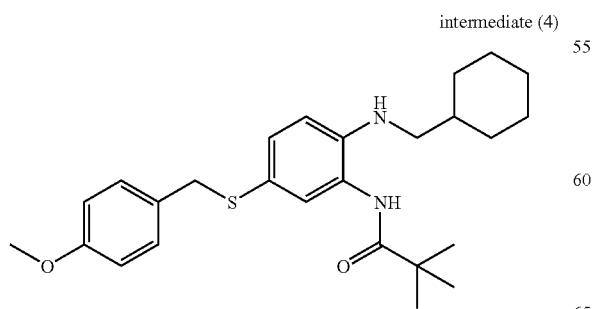
intermediate (4)

Nitrogen gas was bubbled through a mixture of intermediate (3) (0.03 mol), DCM (600 ml) and acetic acid (5 ml) at room temperature. Cyclohexanecarboxaldehyde (4g) was added. After 5 minutes NaBH$_3$(CN) (1.8 g) was added. The reaction mixture was stirred at room temperature for 1 hour. Water was added. The mixture was extracted. The organic layer was separated, dried, filtered and the solvent was evaporated. The residue was crystallized from DIPE. The precipitate was filtered off and dried, yielding 10.5 g of intermediate (4).

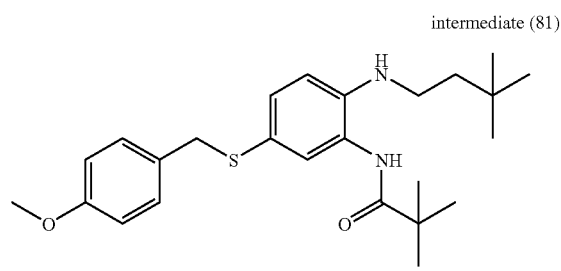 [SMILES: COc1ccc(CSc2ccc(NCCC(C)(C)C)c(NC(=O)C(C)(C)C)c2)cc1]
intermediate (81)

Intermediate (81) was prepared in a similar procedure as intermediate (4) using 3,3-dimethylbutanal.

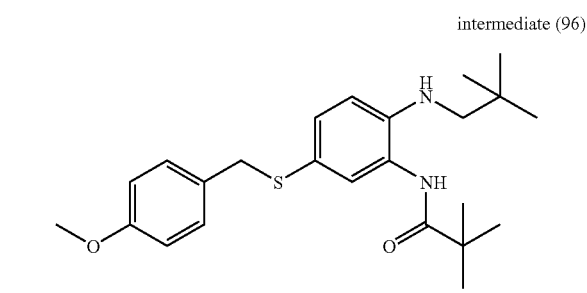 [SMILES: COc1ccc(CSc2ccc(NCC(C)(C)C)c(NC(=O)C(C)(C)C)c2)cc1]
intermediate (96)

Intermediate (96) was prepared in a similar procedure as intermediate (4) using 2,2-dimethylpropanal.

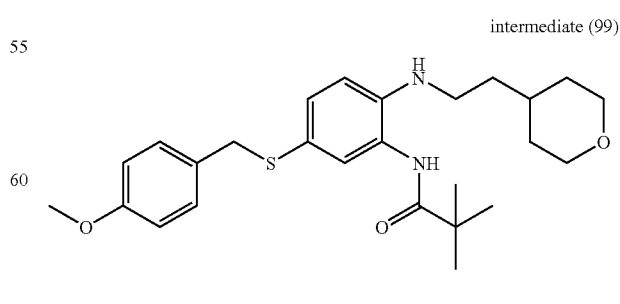
intermediate (99)

Intermediate (99) was prepared in a similar procedure as intermediate (4) using tetrahydro-2H-pyran-4-acetaldehyde.

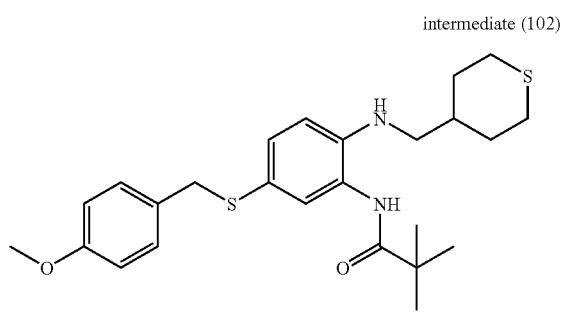 [SMILES: COc1ccc(CSc2ccc(NCC3CCSCC3)c(NC(=O)C(C)(C)C)c2)cc1]

intermediate (102)

Intermediate (102) was prepared in a similar procedure as intermediate (4) using tetrahydro-2H-thiopyran-4-carboxaldehyde. Additionally, titanium (IV) isopropoxide (4:1) was added for the synthesis of intermediate (102).

Intermediate (102) was also prepared in a similar procedure as intermediate (4) using methyl tetrahydro-2H-thiopyran-4-yl ketone.

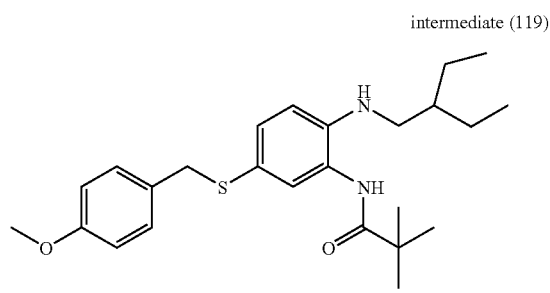 [SMILES: CCC(CC)CNc1ccc(SCc2ccc(OC)cc2)cc1NC(=O)C(C)(C)C]

intermediate (119)

Intermediate (119) was prepared in a similar procedure as intermediate (4) using 2-ethylbutanal.

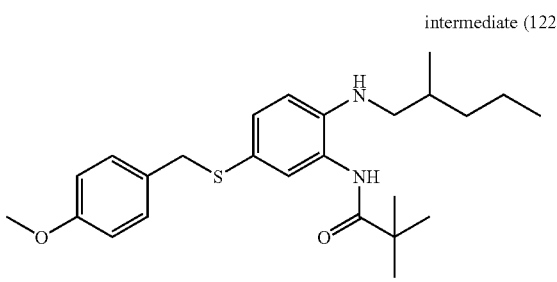

intermediate (122)

Intermediate (122) was prepared in a similar procedure as intermediate (4) using 2-methylpentanal.

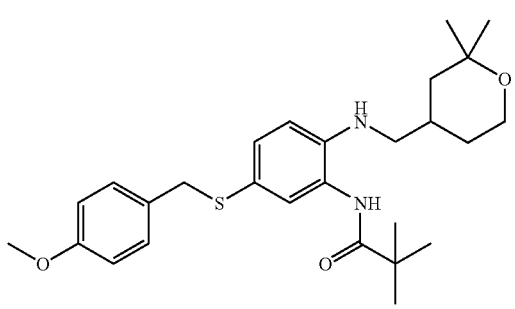

intermediate (125)

Intermediate (125) was prepared in a similar procedure as intermediate (4) using tetrahydro-2,2-dimethyl-2H-pyran-4-carboxaldehyde.

e) Preparation of

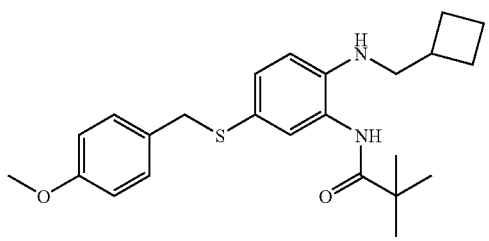

intermediate (105)

Intermediate (105) was prepared in a similar procedure as intermediate (4) using 1,4-dioxaspiro[4.5]decane-8-carboxaldehyde. Additionally, titanium (IV) isopropoxide (4:1) was added for the synthesis of intermediate (105).

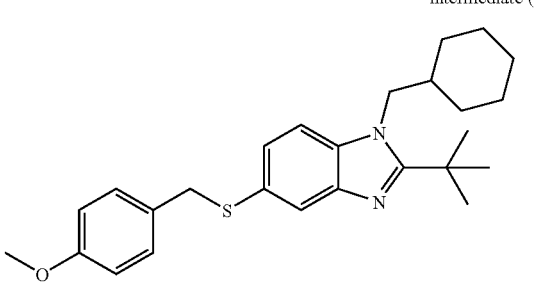

intermediate (92)

Intermediate (92) was prepared in a similar procedure as intermediate (4) using cyclobutanecarboxaldehyde. Additionally, titanium (IV) isopropoxide (4:1) was added for the synthesis of intermediate (92).

intermediate (5)

A mixture of intermediate (4) (0.0045 mol) and acetic acid (40 ml) was stirred and refluxed for 6 hours. The mixture was cooled and the solvent was evaporated. The residue was taken up into DCM and water. The mixture was neutralized with NaHCO$_3$. The organic layer was separated, dried, filtered and the solvent was evaporated. The residue was purified by column chromatography on silicagel (eluent: DCM/methanol 100/0 to 98/2). The product fractions were collected and the solvent was evaporated. The residue was crystallized from DIPE. The precipitate was filtered off, washed and dried, yielding 1g of intermediate (5).

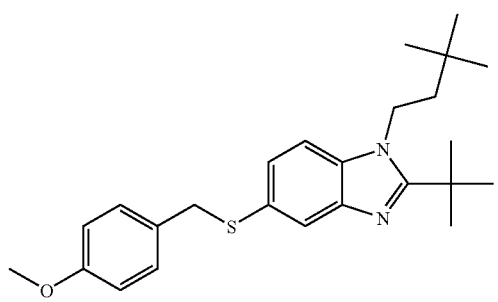

intermediate (82)

Intermediate (82) was prepared in a similar procedure as intermediate (5) starting from intermediate (81).

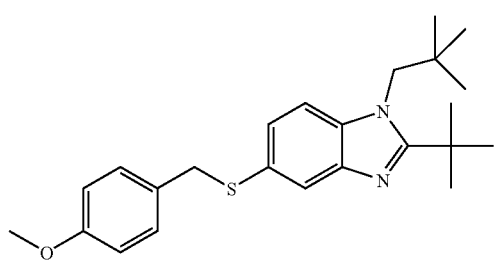

intermediate (97)

Intermediate (97) was prepared in a similar procedure as intermediate (5) starting from intermediate (96).

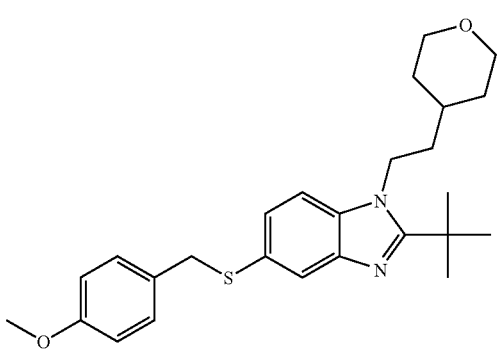

intermediate (100)

Intermediate (100) was prepared in a similar procedure as intermediate (5) starting from intermediate (99).

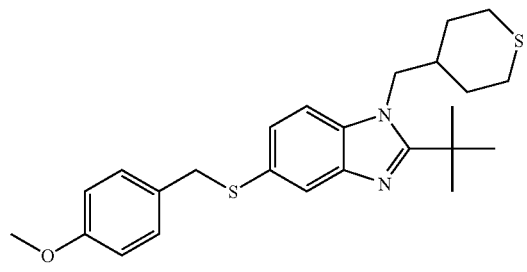

intermediate (103)

Intermediate (103) was prepared in a similar procedure as intermediate (5) starting from intermediate (102).

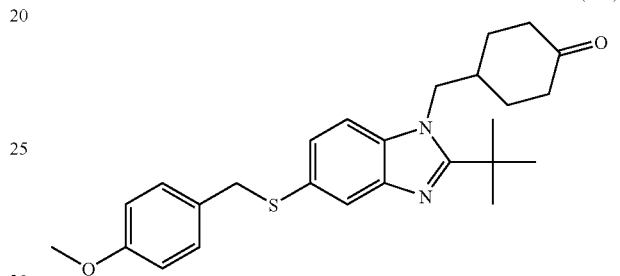

intermediate (106)

Intermediate (106) was prepared in a similar procedure as intermediate (5) starting from intermediate (105).

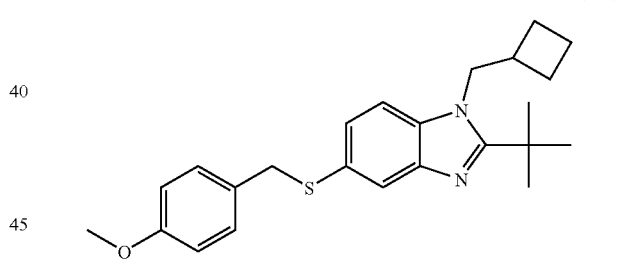

intermediate (110)

Intermediate (110) was prepared in a similar procedure as intermediate (5) starting from intermediate (92).

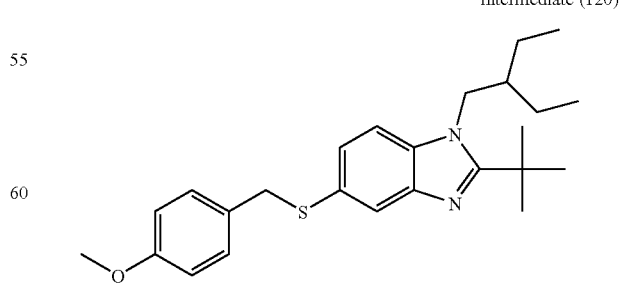

intermediate (120)

Intermediate (120) was prepared in a similar procedure as intermediate (5) starting from intermediate (119).

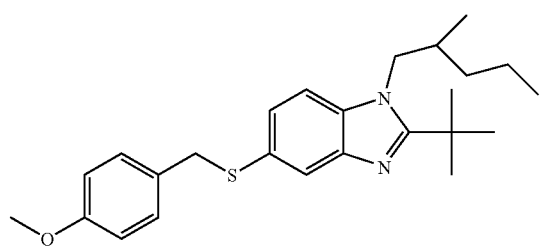

intermediate (123)

Intermediate (123) was prepared in a similar procedure as intermediate (5) starting from intermediate (122). Additionally, a few drops of HCl were added to the reaction mixture.

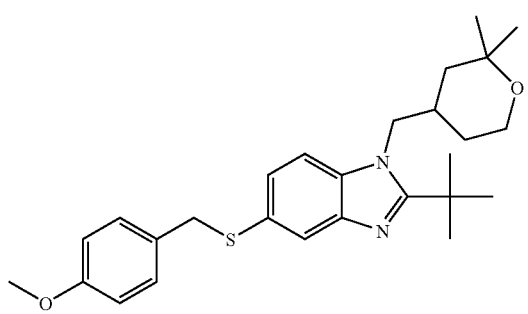

intermediate (126)

Intermediate (126) was prepared in a similar procedure as intermediate (5) starting from intermediate (125).

f) Preparation of

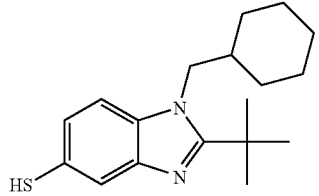

intermediate (6)

A mixture of intermediate (5) (0.019 mol) and trifluoroacetic acid (200 ml) was stirred and refluxed for 5 hours. The mixture was cooled and the solvent was evaporated. The residue was taken up into ethyl acetate and water. The mixture was neutralized with NaHCO₃. The organic layer was separated, dried, filtered and the solvent was evaporated, yielding 8g of intermediate.(6).

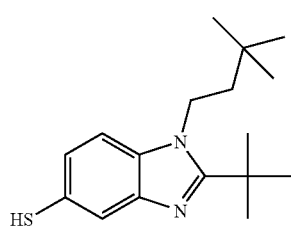

intermediate (83)

Intermediate (83) was prepared in a similar procedure as intermediate (6) starting from intermediate (82).

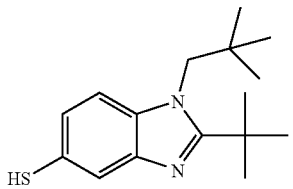

intermediate (98)

Intermediate (98) was prepared in a similar procedure as intermediate (6) starting from intermediate (97).

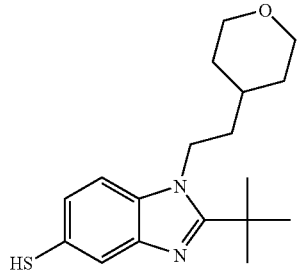

intermediate (101)

Intermediate (101) was prepared in a similar procedure as intermediate (6) starting from intermediate (100).

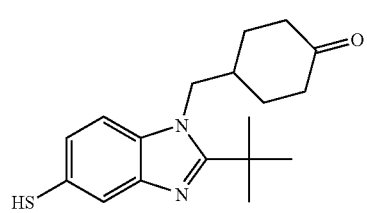

intermediate (118)

Intermediate (104) was prepared in a similar procedure as intermediate (6) starting from intermediate (103).

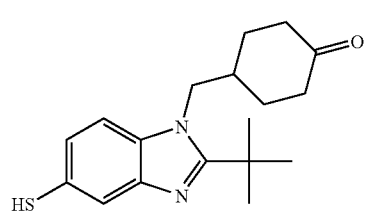

intermediate (118)

Intermediate (118) was prepared in a similar procedure as intermediate (6) starting from intermediate (106).

intermediate (111)

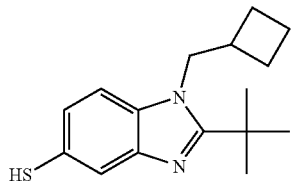

Intermediate (111) was prepared in a similar procedure as intermediate (6) starting from intermediate (110).

intermediate (121)

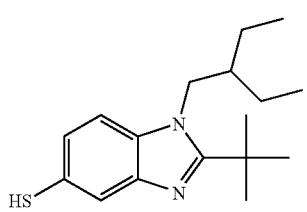

Intermediate (121) was prepared in a similar procedure as intermediate (6) starting from intermediate (120).

intermediate (124)

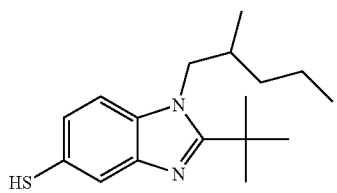

Intermediate (124) was prepared in a similar procedure as intermediate (6) starting from intermediate (123).

intermediate (127)

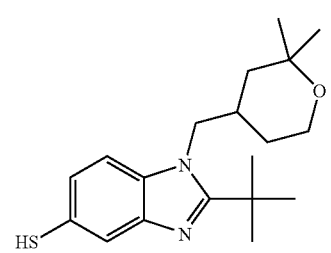

Intermediate (127) was prepared in a similar procedure as intermediate (6) starting from intermediate (126).

EXAMPLE A.2 a) Preparation of intermediate (7)

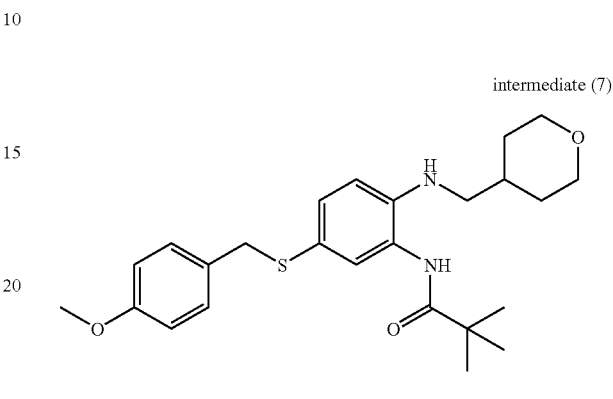

Nitrogen gas was bubbled through a mixture of intermediate (3) (0.032 mol), DCM (650 ml) and acetic acid (5 ml) at room temperature. Tetrahydro-2H-pyran-4-carboxaldehyde (0.039 mol) was added. After 5 minutes $NaBH_3(CN)$ (2g) was added. The reaction mixture was stirred at room temperature for 1 hour. Water was added. The mixture was extracted. The organic layer was separated, dried, filtered and the solvent was evaporated. The residue was crystallized from DIPE. The precipitate was filtered off and dried, yielding 12 g of intermediate (7).

b) Preparation of intermediate (8)

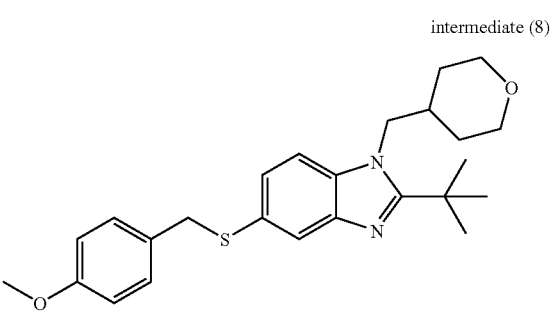 [SMILES: COc1ccc(CSc2ccc3c(c2)nc(C(C)(C)C)n3CC2CCOCC2)cc1]

A mixture of intermediate (7) (0.027 mol) and acetic acid (200 ml) was stirred and refluxed for 6 hours. The mixture was cooled and the solvent was evaporated. The residue was taken up into DCM and water. The mixture was neutralized with $NaHCO_3$. The organic layer was separated, dried, filtered and the solvent was evaporated. The residue was purified by column chromatography (eluent: $DCM/CH_3OH$ 100/0 to 96/4). The product fractions were collected and the solvent was evaporated. The residue was crystallized from DIPE. The precipitate was filtered off, washed and dried, yielding 8 g of intermediate (8).

c) Preparation of

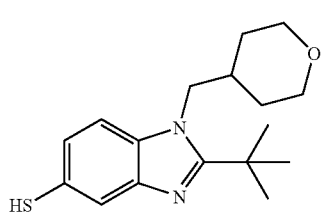
intermediate (9)

A mixture of intermediate (8) (0.019 mol) in trifluoroacetic acid (200 ml) was stirred and refluxed for 5 hours. The mixture was cooled and the solvent was evaporated. The residue was taken up into ethyl acetate and water. The mixture was neutralized with NaHCO₃. The organic layer was separated, dried, filtered and the solvent was evaporated, yielding 7 g of intermediate (9).

EXAMPLE A.3 a) Preparation of

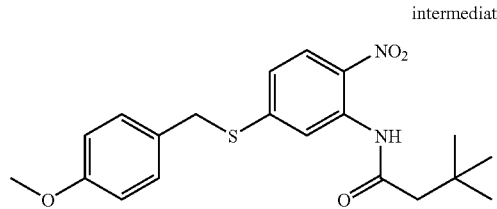
intermediate (10)

3,3-Dimethylbutanoyl chloride (0.20 mol) was added dropwise to a mixture of intermediate (1) (0.16 mol) in pyridine (600 ml) at room temperature and stirred for 1 hour at room temperature. The solvent was evaporated. The residue was taken up in DCM. This mixture was washed with water, diluted HCl aqueous solution and with diluted NH₄Cl aqueous solution. The separated organic layer was dried, filtered and the solvent was evaporated, yielding 62 g of intermediate (10).

b) Preparation of

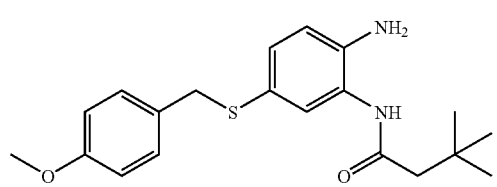
intermediate (11)

A mixture of intermediate (10) (0.12 mol) in THF (500 ml) was hydrogenated at a temperature below 30° C. with a mixture of platinum on activated carbon (5%)+vanadium pentoxide (0.5%) (5g) as a catalyst. After uptake of hydrogen (3 equiv.), the catalyst was filtered off and the filtrate's solvent was evaporated. The residue was suspended in DIPE. The precipitate was filtered off, washed and dried, yielding 39g of intermediate (11)

c) Preparation of

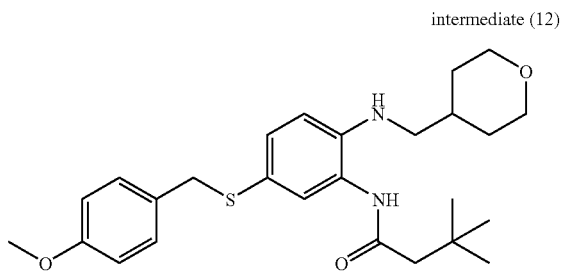 [SMILES: COc1ccc(CSc2ccc(NCC3CCOCC3)c(NC(=O)CC(C)(C)C)c2)cc1]
intermediate (12)

A mixture of intermediate (11) (0.07 mol) in DCM (1300 ml) and acetic acid (10 ml) at room temperature was bubbled with nitrogen. Tetrahydro-2H-pyran-4-carboxaldehyde (0.088 mol) was added at room temperature to the reaction mixture and stirred for 30 minutes at room temperature. Sodium cyanotrihydroborate (4.5 g) was added in 10 portions at room temperature. The reaction mixture was stirred for 30 minutes. Water was added and after extraction, the separated organic layer was dried, filtered and the solvent was evaporated. The residue was suspended in DIPE. The precipitate was filtered off, washed and dried, yielding 23.5 g of intermediate (12).

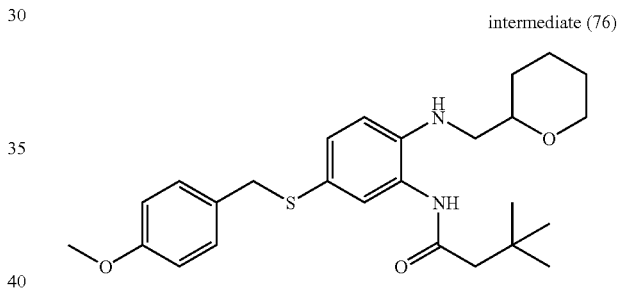
intermediate (76)

Intermediate (76) was prepared in a similar procedure as intermediate (12) using tetrahydro-2H-pyran-2-carboxaldehyde.

d) Preparation of

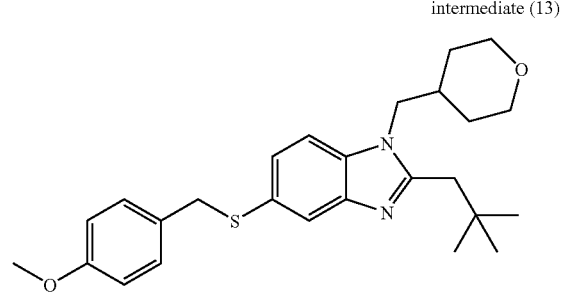 [SMILES: COc1ccc(CSc2ccc3c(c2)nc(CC(C)(C)C)n3CC2CCOCC2)cc1]
intermediate (13)

Intermediate (12) (0.051 mol) in acetic acid (500 ml) was stirred for 2 hours at reflux temperature. The reaction mixture was cooled and the solvent was evaporated. The residue was taken up in DCM and water. This mixture was neutralized to pH=7 with NaHCO₃. After extraction, the separated organic layer was dried, filtered and the solvent was evaporated, yielding 23g of intermediate (13).

EXAMPLE A.4 a) Preparation of intermediate (15)

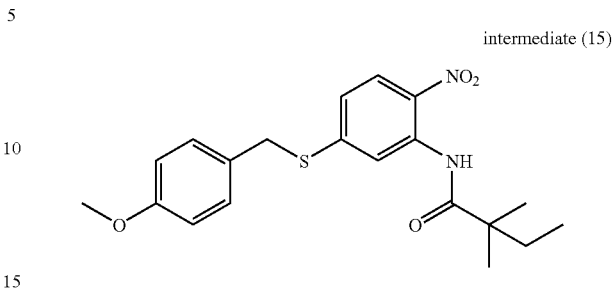

2,2-Dimethylbutyric acid chloride (0.2 mol) was added to intermediate (1) (0.18 mol) in pyridine (550 ml). The reaction mixture was stirred and refluxed for 2 hours. The reaction mixture was cooled and the solvent was evaporated. The residue was partitioned between water and DCM. The organic layer was separated, dried, filtered and the solvent was evaporated. The residue was suspended in DIPE. The resulting precipitate was filtered off and dried, yielding 62g of intermediate (15).

b) Preparation of intermediate (16)

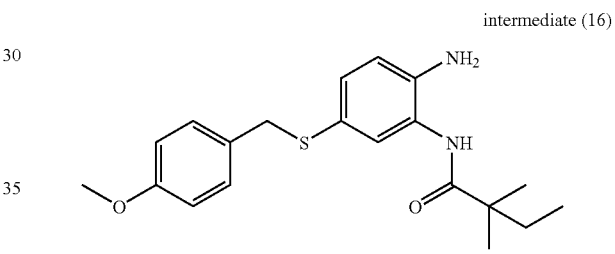

A mixture of intermediate (15) (0.16 mol) in THF (500 ml) was hydrogenated at 25° C. with platinum-on-carbon (5%, 5g) as a catalyst in the presence of a small quantity of V₂O₅. After uptake of hydrogen, the catalyst was filtered off and to the filtrate, extra platinum-on-carbon (5%, 5g) and a small quantity of V₂O₅ were added. The hydrogenation was continued until hydrogen (3 equiv.) were taken up. The catalyst was filtered off and the filtrate was evaporated. The residue was suspended in DIPE, filtered off and dried, yielding intermediate (16).

c) Preparation of intermediate (17)

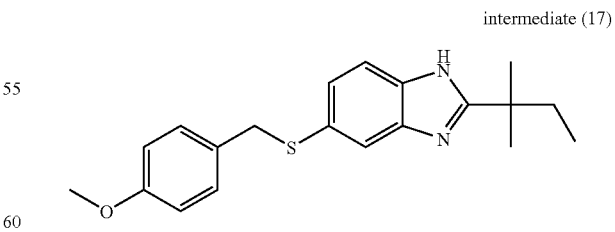

A mixture of intermediate (16) (0.056 mol) in acetic acid (300 ml) was stirred and refluxed for 3 hours, then cooled and the solvent was evaporated. The residue was partitioned between water and DCM. The mixture was neutralized with an aqueous NaHCO₃ solution. The organic layer was separated, dried, filtered and the solvent was evaporated. Part (2.5 intermediate (77)

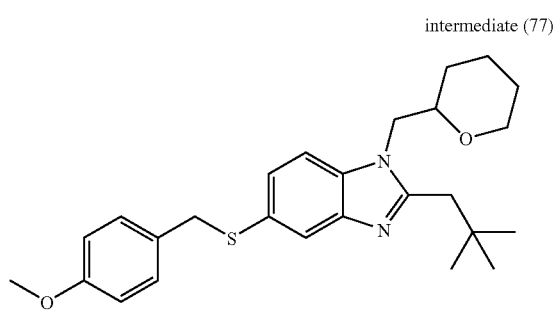 [SMILES: COc1ccc(CSc2ccc3c(c2)nc(CC(C)(C)C)n3CC2CCCCO2)cc1]

Intermediate (77) was prepared in a similar procedure as intermediate (13) starting from intermediate (76).

e) Preparation of intermediate (14)

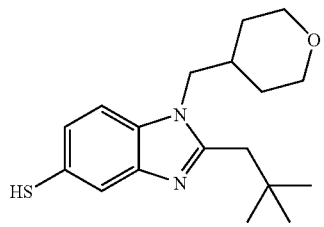

Intermediate (13) (0.0044 mol) in trifluoroacetic acid (20 ml) was heated in a microwave at 150° C. for 15 minutes. The reaction mixture was cooled and the solvent was evaporated. The residue was taken up in ethyl acetate and water. This mixture was neutralized to pH=7 with NaHCO₃. After extraction, the separated organic layer was dried, filtered and the solvent was evaporated, yielding 2.2 g of intermediate (14).

intermediate (78)

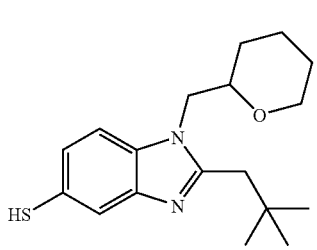

Intermediate (78) was prepared in a similar procedure as intermediate (14) starting from intermediate (77).

g) of the residue was dissolved in ethanol (50 ml). NaBH$_4$ (0.160g) was added and the reaction mixture was stirred and refluxed for 2 hours. Extra NaBH$_4$ (0.500g) was added and the reaction mixture was stirred and refluxed for 20 hours. The remaining residue was dissolved in ethanol. NaBH$_4$ (6 g) was added and the reaction mixture was stirred and refluxed for 20 hours. The reaction mixture was cooled. Water was added The solvent was evaporated. The residue was partitioned between water and DCM. The organic layer was separated, dried, filtered and the solvent was evaporated. The residue was suspended in DIPE, filtered off and dried, yielding 15 g of intermediate (17).

d) Preparation of intermediate (18)

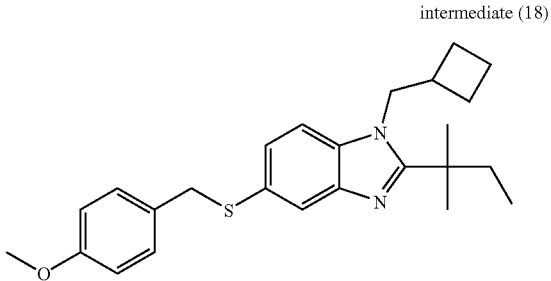 [SMILES: CCC(C)(C)c1nc2cc(SCc3ccc(OC)cc3)ccc2n1CC1CCC1]

Reaction under nitrogen atmosphere. A solution of intermediate (17) (0.021 mol) in THF (250 ml) was stirred. Sodiumhydride (0.025 mol) was added and the reaction mixture was stirred for 30 minutes at 40° C. Cyclobutylmethyl bromide (0.025 mol) was added and the reaction mixture was stirred for 2 hours at 40° C. More cyclobutyl-methyl bromide (1 equiv.) was added and the reaction mixture was stirred for 20 hours at 60° C. More sodium hydride (0.3 g) was added. Extra cyclobutylmethyl bromide (1 g) was added and the reaction mixture was stirred for 20 hours at 60° C. Extra sodium hydride (0.3 g) was added, followed by addition of cyclobutylmethyl bromide (1g). Upon reaction completion, the reaction mixture was cooled. The solvent was evaporated. The residue was partitioned between water and DCM. The organic layer was separated, dried, filtered and the solvent was evaporated. The residue was purified by column chromatography over silica gel (eluent: CH$_2$Cl$_2$/CH$_3$OH 99/1). The product fractions were collected and the solvent was evaporated, yielding 1.2 g of intermediate (18).

e) Preparation of intermediate (19)

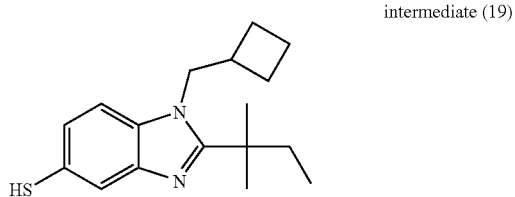 [SMILES: CCC(C)(C)c1nc2cc(S)ccc2n1CC1CCC1]

Reaction in microwave oven. Intermediate (18) (0.003 mol) in trifluoroacetic acid (15 ml) was heated for 15 minutes at 110° C. The reaction mixture was cooled and the solvent was evaporated. The residue was partitioned between water and ethyl acetate. The mixture was neutralized with an aqueous NaHCO$_3$ solution. The organic layer was separated, dried, filtered and the solvent was evaporated, yielding intermediate (19).

EXAMPLE A.5

Preparation of intermediate (20)

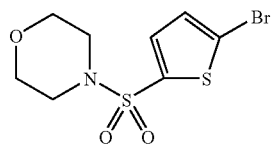

A mixture of morpholine (0.007 mol) in THF (30 ml) and triethylamine (0.800 g) was stirred at room temperature. A solution of 5-bromo-2-thiophenesulfonyl chloride (0.005 mol) in THF (10 ml) was added slowly at room temperature. The reaction mixture was stirred overnight at room temperature in a closed reaction vessel. Then, the mixture was taken up into ethyl acetate, washed with water, with 1 N HCl (20 ml), with a saturated aqueous NaHCO$_3$ solution, then dried, filtered and the solvent was evaporated, yielding 1.6 g of intermediate (20).

EXAMPLE A.6

Preparation of intermediate (21)

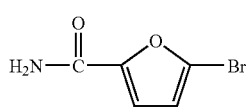

Ammonia was bubbled in excess through a THF (20 ml) solution. A solution of 2-bromo-5-furancarbonyl chloride (0.005 mol) in THF (10 ml) was added dropwise. The resultant reaction mixture was stirred for 3 hours at 50° C. DCM (100 ml) was added. Water (40 ml) was added. The biphasic mixture was shaken for a while. The layers were separated. The organic layer was dried, filtered and the solvent was evaporated, yielding 0.970 g of intermediate (21).

EXAMPLE A.7

Preparation of intermediate (22)

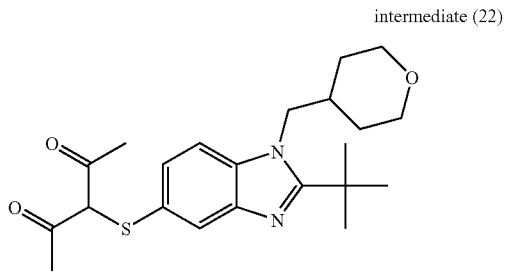 [SMILES: CC(=O)C(Sc1ccc2c(c1)nc(C(C)(C)C)n2CC1CCOCC1)C(C)=O]

Reaction under Argon flow. Intermediate (8) (0.00235 mol) was dissolved in degassed trifluoroacetic acid (20 ml) and stirred overnight at 80° C. The solvent was evaporated. The residue was taken up in degassed toluene. The mixture was washed with degassed saturated aqueous NaHCO$_3$ solution. The organic layer was separated, dried, filtered and the solvent was evaporated. The residue was dissolved in degassed dioxane (20 ml). 3-Bromo-2,4-pentanedione (0.00235 mol) and Cs₂CO₃ (1.15 g) were added. The reaction mixture was stirred at 100° C. for 3 hours. The reaction mixture was cooled and the solvent was evaporated. The residue was taken up in ethyl acetate. The organic layer was separated, washed with water and then with brine, dried, filtered and the solvent was evaporated. The residue was purified by column chromatography over silica gel (eluent: hexane/ethyl acetate 1/2). The product fractions were collected and the solvent was evaporated, yielding 0.090 g of intermediate (22).

EXAMPLE A.8

Preparation of

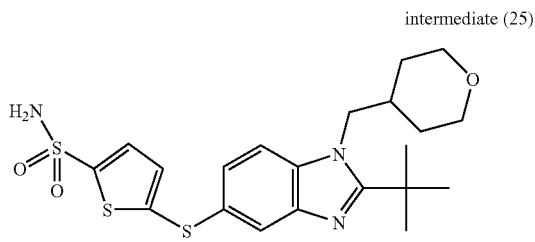 [SMILES: CC(C)(C)c1nc2cc(Sc3ccc(S(N)(=O)=O)s3)ccc2n1CC1CCOCC1]

intermediate (25)

A mixture of intermediate (9) (0.002 mol) and 5-bromo-2-thiophenesulfonamide (0.0025 mol) in dioxane (40 ml) was degassed and a flow of nitrogen was brought over the reaction mixture (3 times). Then Cs₂CO₃ (0.004 mol) was added and the mixture was degassed and nitrogen was brought over the reaction mixture again. (twice). Then Pd₂(dba)₃ (0.0001 mol) and Xantphos (0.0001 mol) were added and degassing and the nitrogen action were performed (twice). A nitrogen balloon was left on the reaction mixture and the mixture was stirred overnight at 100° C. The mixture was cooled, filtered and the filtrate was evaporated, yielding intermediate (25).

The heterocyclic reagent 5-bromo-2-thiophenesulfonamide can be replaced by other heterocycles such as e.g. 5-bromo-2(1H)-pyridinone, 4-chloro-pyridine hydrochloride, 1-(6-chloro-3-pyridinyl-1-ethanone, 5-bromo-2-thiophenesulfonamide, 3-(bromo-3-thienyl)-5-methyl-1,2,4-oxadiazole, 2-(ethylsulfonyl)-5-iodo-thiophene, 4-bromo-1H-pyridin-2-one, 4-bromo-2-ethoxy-pyridine, 2,4,6-trichloropyridine, 4-chloro-2-methyl-pyridine, 3-chloro-6-methoxy-pyridazine, 4-chloro-3-(trifluoromethyl)pyridine hydrochloride, N-(4-chloro-2-pyridinyl)-acetamide, 4-bromo-2-methyl-pyridine, 4-bromo-2-fluoro-pyridine, 1-(5-bromopyridin-2-yl)ethanone, 2-methylsulfonyl-5-bromopyridine, intermediate (20), intermediate (21), 4-bromo-2-chloropyridine, 2-chloro-4-pyrimidinecarboxamide, 6-chloro-3-pyridinecarboxylic acid, methyl ester, 5-bromo-3-pyridinecarbonitrile, 5-bromo-2(1H)-pyridinone, 1-(5-bromo-2-thienyl)-ethanon, 5-bromo-2-thiophenecarbonitrile, 5-bromo-2-pyridinecarbonitrile], 1-(4-iodophenyl)-ethanone, 5-bromo-2-methoxy-pyridine, 2-(4-bromo-2-furanyl)-1,3-dioxolan, 5-bromo-2-(methylsulfonyl)pyridine, 2-bromo-5-(methylsulfonyl)thiophene, 5-bromo-N-ethyl-2-thiophenesulfonamide, 5-bromo-2-furancarbonitrile, intermediate 34, 4-[(4,5-dibromo-2-thienyl)sulfonyl]morpholine, 4-[(6-chloro-3-pyridinyl)sulfonyl]-morpholine, 2-chloro-5-(methylsulfonyl)pyridine, intermediate 36, 5-bromo-2-thiophenecarboxamide, 1-[(5-bromo-2-furanyl)carbonyl]pyrrolidine, 3-chlorobenzene-carboperoxoic acid, 4-[(5-bromo-2-thienyl)carbonyl]morpholine, 4-[(5-bromo-2-furanyl)carbonyl]morpholine, 5-bromo-4-methyl-2-thiophenecarboxylic acid, methyl ester, 4-[(4,5-dibromo-2-thienyl)sulfonyl]morpholine, 3-chloro-6-methoxypyridazine, 6-bromo-2-pyridinecarbonitrile, 4-bromo-2-methylpyridine, 4-chloro-2-methyl-pyrimidine, 4-bromo-2-fluoropyridine, 4-bromo-3-methoxypyridine, 3-iodo-2-(trifluoromethyl)pyridine, intermediate (84), intermediate (116), 4-chloropyridine hydrochloride (1:1), intermediate (129), intermediate (135), 2-chloro-5-thiazole-carbonitrile, 4-bromo-2(1H)-pyridinone and 4-bromo-2-ethoxypyridine for the preparation of other compounds of the invention.

The starting material intermediate (9) can be replaced by other intermediates such as e.g. intermediate (6), intermediate (14), intermediate (62), intermediate (66), intermediate (70), intermediate (78), intermediate (83), intermediate (98), intermediate (101), intermediate (104), intermediate (111), intermediate (118), intermediate (121), intermediate (124), intermediate (127) for the preparation of other compounds of the invention.

The following intermediates are prepared according to a similar procedure as intermediate (25) (Example A.8) starting from intermediate (9) and a variable heterocyclic reagent as indicated were used.

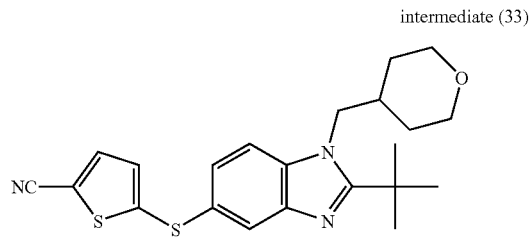

intermediate (33)

heterocycle: 5-bromo-2-thiophenecarbonitrile

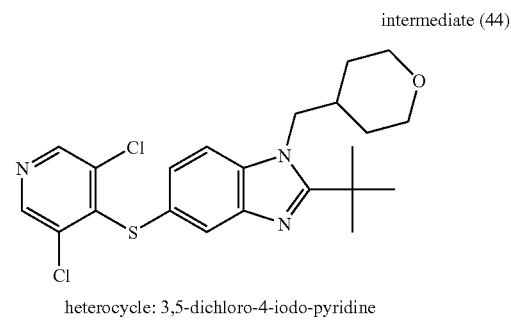

intermediate (44)

heterocycle: 3,5-dichloro-4-iodo-pyridine

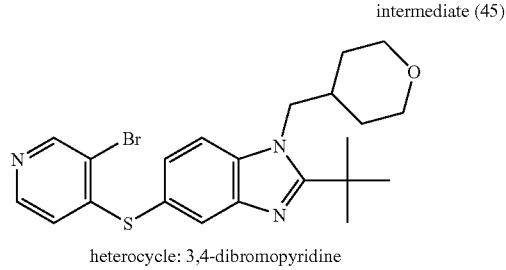

intermediate (45)

heterocycle: 3,4-dibromopyridine

-continued

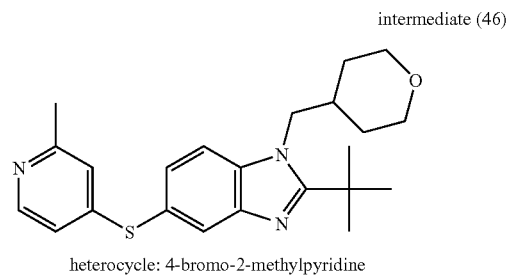
intermediate (46)
heterocycle: 4-bromo-2-methylpyridine

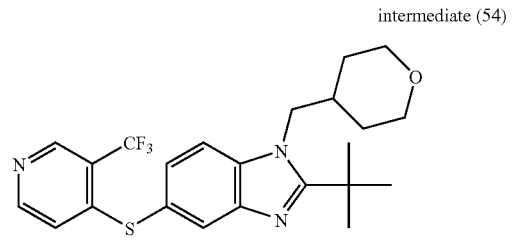
intermediate (54)
heterocycle: 4-chloro-3-(trifluoromethyl)-pyridine, hydrochloride

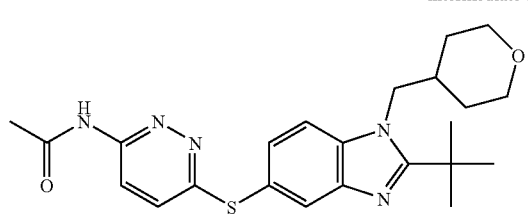
intermediate (56)
heterocycle: N-(6-chloro-3-pyridazinyl)-acetamide

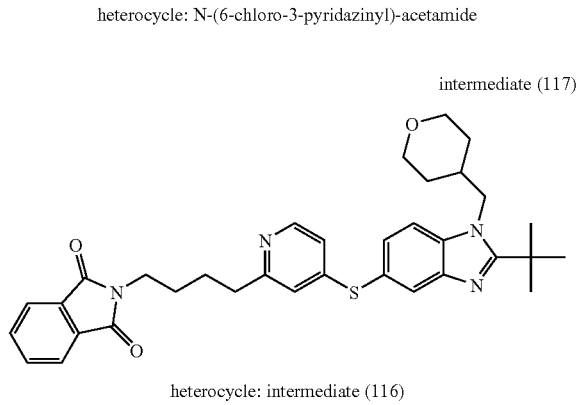
intermediate (117)
heterocycle: intermediate (116)

The following intermediate was also prepared according to a similar procedure as intermediate (25) (Example A.8), but starting from intermediate (111) and 4-bromo-2-fluoropyridine (as the heterocyclic reagent)

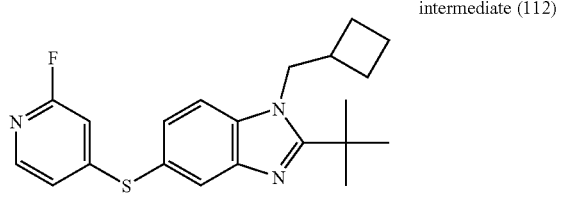 [SMILES: CC(C)(C)c1nc2cc(Sc3ccnc(F)c3)ccc2n1CC1CCC1]
intermediate (112)

EXAMPLE A.9 a) Preparation of

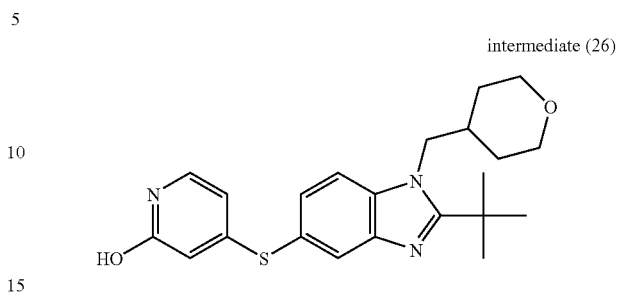
intermediate (26)

$Cs_2CO_3$ (0.0061 mol) was added to 4-bromo-2(1H)-pyridinone (0.004 mol) in dioxane (10 ml). The mixture was degassed three times with nitrogen. A degassed solution of intermediate (9) (0.0023 mol) in dioxane (10 ml) was added. The reaction mixture was degassed once more. $Pd_2(dba)_3$ (0.047 g) and Xantphos (0.060 g) were added. The reaction mixture was degassed, then stirred overnight at 100° C. The reaction mixture was cooled. DCM (150 ml) was added. A 5% aqueous $NH_4Cl$ solution (150 ml) was added and mixed. The layers were separated. The aqueous phase was extracted with DCM (100 ml). The combined organic layers were dried, filtered and the solvent was evaporated. The residue was purified by CombiFlash flash column chromatography (eluent: $CH_2Cl_2/CH_3OH$ from 100/0 to 94/6). The product fractions were collected and the solvent was evaporated, yielding 0.93 g of intermediate (26).

b-1) Preparation

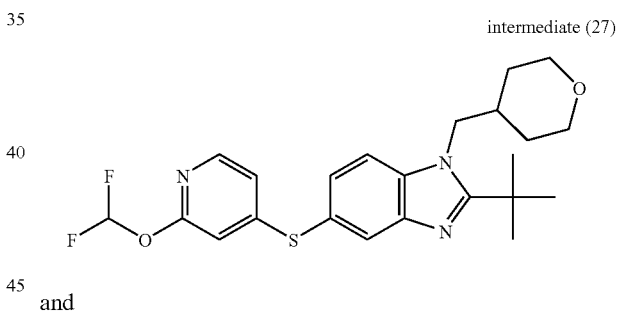
intermediate (27)

and

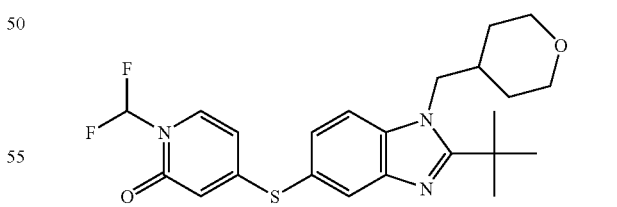
intermediate (43)

A mixture of intermediate (26) (0.005 mol), chlorodifluoroacetic acid sodium salt (0.01 mol) and $K_2CO_3$ (0.006 ml) in $DMF/H_2O$ (5 ml) was degassed for 15 minutes. The reaction mixture was stirred overnight at 100° C. The reaction mixture was cooled and a mixture (4 ml) of HCl 12N and water (ratio 1/1.5) was added. The separated organic layer was dried, filtered and the solvent was evaporated. The residue was purified by reversed-phase HPLC (gradient elution with $NH_4HCO_3$ buffer (0.25% in water)/$CH_3OH/CH_3CN$). Two different product fractions were collected and worked-up, yielding crude intermediate (43) (used as such in the next reaction) and 0.221 g of intermediate (27).

b-2) Preparation of intermediate (47)

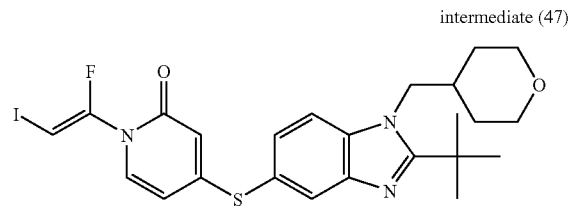 [SMILES: CC(C)(C)c1nc2cc(Sc3ccn(/C(F)=C/I)c(=O)c3)ccc2n1CC1CCOCC1]

and intermediate (48)

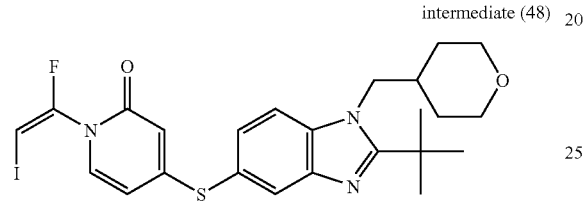

1,1,1-Trifluoro-2-iodoethane (0.0075 mol) was added to a mixture of intermediate (26)(0.005 mol) and sodium hydride (0.006 mol) in DMF (5 ml). The reaction mixture was stirred at 0° C. for 4 hours. The reaction mixture was partitioned between DCM and water. The separated organic layer was dried (MgSO$_4$), filtered and the solvent was evaporated. The residue was purified by reversed-phase HPLC (gradient elution with NH$_4$HCO$_3$ buffer (0.25% in water)/CH$_3$OH/CH$_3$CN). The desired product fractions were collected and worked-up, yielding 0.176 g of intermediate (48) (E-isomer) and 0.367 g intermediate (47) (Z-isomer).

b-3) Preparation of intermediate (55)

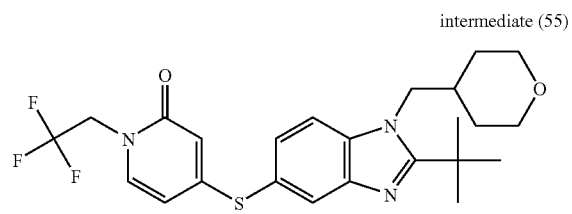 [SMILES: CC(C)(C)c1nc2cc(Sc3ccn(CC(F)(F)F)c(=O)c3)ccc2n1CC1CCOCC1]

A mixture of intermediate (26) (0.000722 mol), 2,2,2-trifluoro-ethanol, 1-(4-methyl-benzenesulfonate) (0.00144 mol) and potassium carbonate (0.132 g) in DMF (5 ml) was heated to 60° C. The reaction mixture was extracted with DCM/water. The separated organic layer was dried, filtered and the solvent was evaporated. The residue was purified by reversed-phase HPLC (gradient elution with NH$_4$HCO$_3$ buffer (0.25% in water)/CH$_3$OH/CH$_3$CN). The desired product fraction was collected and the solvent was evaporated, yielding 0.116 g of intermediate (55).

Intermediate (58) was prepared in a similar procedure as intermediate (55), starting from intermediate (23) and 1,1,2,2,3,3,4,4,4-nonafluoro-1-butanesulfonic acid, 2,2,2-trifluoroethyl ester.

intermediate (58)

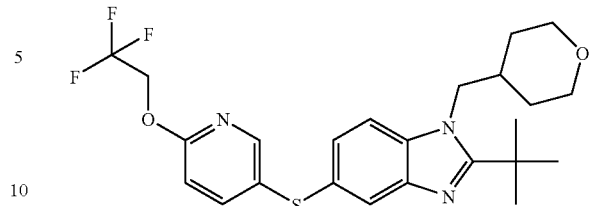

EXAMPLE A.10

Preparation of intermediate (28)

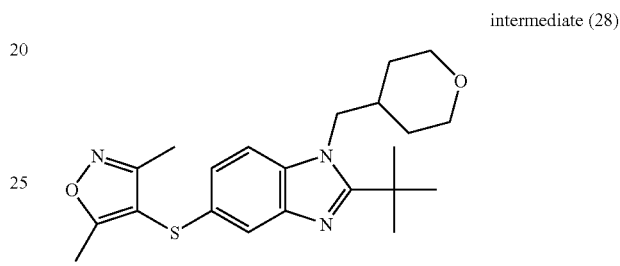

Hydroxylamine hydrochloride (0.000211 mol) and then water (0.5 ml) were added to a solution of intermediate (22) (0.000211 mol) dissolved in methanol (3.5 ml) and stirred overnight at a temperature between 60° C. and 70° C. The reaction mixture was cooled and diluted with chloroform. The separated organic layer was dried, filtered and the solvent was evaporated. The residue was purified by column chromatography over silica gel (eluent: ethyl acetate/hexane 50/50). The product fractions were collected and the solvent was evaporated, yielding 0.050 g of intermediate (28).

EXAMPLE A.11 a) Preparation of intermediate (29)

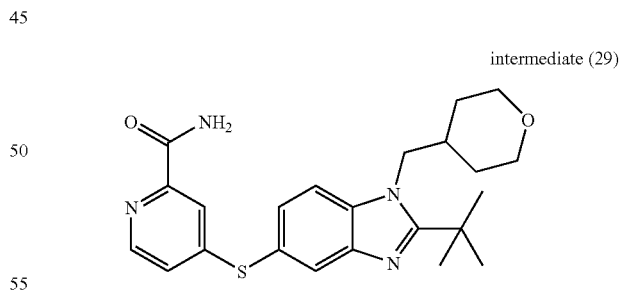

Cs$_2$CO$_3$ (0.0032 mol) was added to 4-chloro-2-pyridinecarboxamide (0.00318 mol) in dioxane (10 ml). The mixture was degassed three times using nitrogen. A degassed solution of intermediate (9) (0.003 mol) in dioxane (10 ml) was added. The reaction mixture was degassed once more. Pd$_2$(dba)$_3$ (0.100 g) and Xantphos (0.130 g) were added. The reaction mixture was degassed, then put in a sealed reaction vessel under nitrogen atmosphere, then stirred overnight at 100° C. The reaction mixture was cooled, and water (200 ml) was added. This mixture was extracted with DCM (2×150 ml). The combined organic layers were dried, filtered and the solvent was evaporated. The residue was purified by reversed-phase HPLC. The product fractions were collected and the solvent was evaporated, yielding 0.6 g of intermediate (29).

b) Preparation of

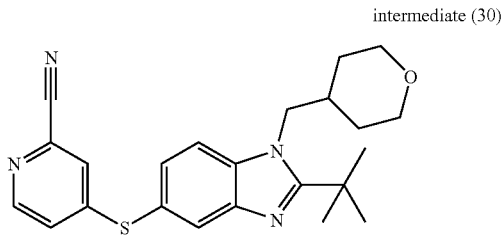 [SMILES: CC(C)(C)c1nc2cc(Sc3ccnc(C#N)c3)ccc2n1CC1CCOCC1]

intermediate (30)

Intermediate (29) (0.00075 mol) in DMF (5 ml) was cooled on an ice-bath. Phosphoric trichloride (0.0016 mol) was added dropwise. The reaction mixture was stirred for 4 hours at a temperature between 0° C. and 5° C. The reaction mixture was poured out into ice-water (75 ml). The pH was neutralized by addition of NaHCO$_3$. The resulting precipitate was filtered off, washed with water, and dried, yielding 0.270g of intermediate (30).

EXAMPLE A.12

Preparation of

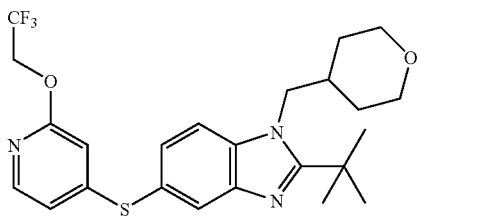

intermediate (31)

A mixture of intermediate (26) (0.000722 mol), 2,2,2-trifluoroethanol, 4-methyl-benzenesulfonate (0.00144 mol) and K$_2$CO$_3$ (0.132 g) in DMF (3 ml) was heated to 60° C. The reaction mixture was extracted using DCM and water. The separated organic layer was dried, filtered and the solvent was evaporated. The residue was purified by reversed-phase HPLC (gradient elution with NH$_4$HCO$_3$ buffer (0.25% in water)/CH$_3$OH/CH$_3$CN). The product fractions were collected and the solvents were evaporated, yielding 0.085 g of intermediate (31).

EXAMPLE A.13

Preparation of

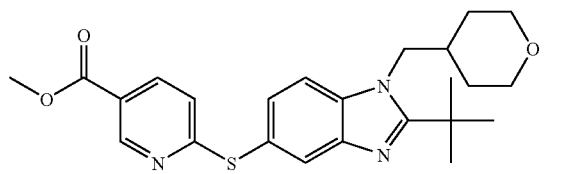

intermediate (32)

A mixture of intermediate (9) (max. 0.0016 mol), 6-chloro-3-pyridinecarboxylic acid methyl ester (0.004 mol) and Cs$_2$CO$_3$ (0.003 mol) in dioxane (10 ml) was stirred overnight at room temperature. The solvent was evaporated under a stream of N$_2$. The residue was partitioned between DCM and water. The separated organic layer was dried by passing through an Isolute filter and the solvent was evaporated. The residue was purified by reversed-phase HPLC. The product fractions were collected and the solvent was evaporated, yielding 0.344 g of intermediate (32)

The heterocyclic reagent 6-chloro-3-pyridinecarboxylic acid, methyl ester can be replaced by other heterocycles such as e.g. 2-chloro-5-(trifluoromethyl)pyridine, 2-chloro-3-pyridinecarbonitrile, 2-chloro-4-(trifluoromethyl)pyridine, 2-chloro-6-(trifluoromethyl)pyridine for the preparation of other intermediates.

EXAMPLE A.14

Preparation of

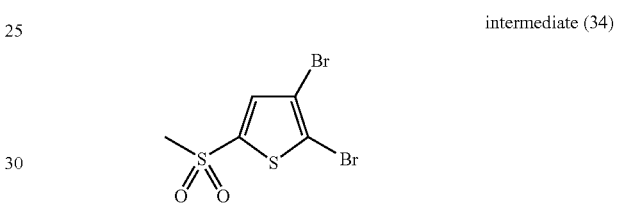

intermediate (34)

A mixture of sodium hydrogen carbonate (0.570 g) and sodium sulfite (0.800 g) in water (15 ml) was stirred. A solution of 4,5-dibromo-2-thiophenesulfonyl chloride (0.005 mol) in THF (10 ml) was added. The resultant mixture was stirred for 2 hours at 75° C. Then, the mixture was cooled to 30° C. Iodomethane (1.4 ml) was added and the resultant reaction mixture was stirred overnight at 50° C., then cooled, taken up into ethyl acetate, washed with water and the layers were separated. The aqueous phase was extracted once more with ethyl acetate. The organic layers were combined, dried, filtered and the solvent was evaporated, yielding 1.120 g of intermediate (34).

EXAMPLE A.15 a) Preparation of

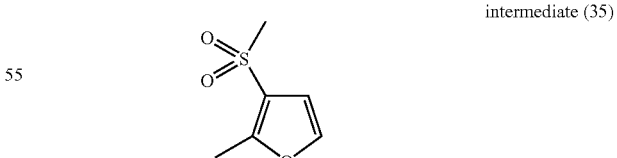

intermediate (35)

mCPBA (77%) (5.7 g) was added to a mixture of 2-methyl-3-(methylthio)furan (1.4 g, 0.011 mol) in chloroform (50 ml) at room temperature (slightly exothermic). The reaction mixture was stirred for 2 hours and was then washed with water and a NaOH solution (30%). The separated organic layer was dried (MgSO$_4$), filtered and the solvent was evaporated, yielding 1.75 g of intermediate (35).

b) Preparation of

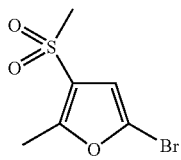
intermediate (36)

Intermediate (35) (0.004 mol) was stirred in DMF (7 ml). 1-Bromo-2,5-pyrrolidinedione (0.0048 mol) was added carefully over a 2-minutes period. The reaction mixture was stirred for one hour. The mixture was poured out into water and this mixture was extracted with ethyl acetate. The separated organic layer was dried (MgSO$_4$), filtered and the solvent evaporated, yielding 1.00 g of intermediate (36).

EXAMPLE A.16

Preparation of

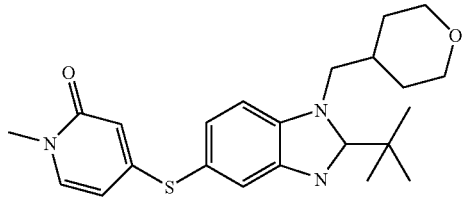
intermediate (37)

and

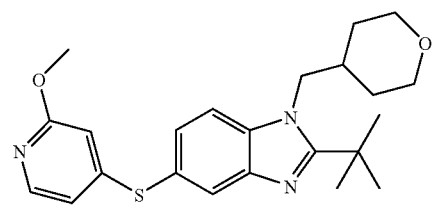
intermediate (38)

A mixture of intermediate (26) (0.00116 mol) and sodium hydride in mineral oil (60%) (0.0015 mol) in DMF (10 ml) was stirred for 30 minutes at 60° C. Then the mixture was cooled to room temperature. Iodomethane (0.0015 mol) was added and the resultant reaction mixture was shaken overnight at room temperature. Ethyl acetate (100 ml) was added. Water (100 ml) was added and the whole was mixed. The layers were separated. The aqueous phase was extracted with ethyl acetate (100 ml). The combined organic layers were dried (MgSO$_4$), filtered and the solvent was evaporated. The residue was purified by reversed-phase HPLC. Two product fraction groups were collected and their solvent was evaporated, yielding 0.36 g of intermediate (37) and 0.015 g of intermediate (38).

EXAMPLE A.17

Preparation of

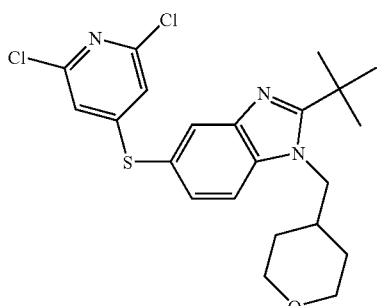
intermediate (39)

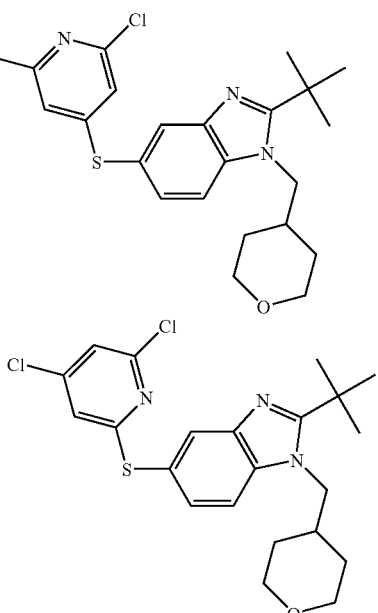

A mixture of 2,4,6-trichloropyridine (0.01034 mol), Cs$_2$CO$_3$ (3.3 g), Pd$_2$(dba)$_3$ (0.130 g) and Xantphos (0.163 g) in degassed dioxane was stirred. A solution of intermediate (9) (0.0047 mol) in dioxane was added. The reaction mixture was heated for 20 hours at 100° C., then cooled, filtered and the filtrate's solvent was evaporated. The residue was partitioned between water and DCM. The organic layer was separated, dried, filtered and the solvent evaporated, yielding of intermediate (39) as a mixture of region-isomers.

EXAMPLE A.18

Preparation of

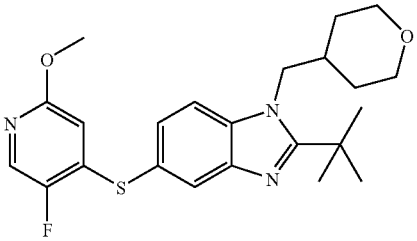
intermediate (40)

All apparatus was flushed with N$_2$ and dried by heating. Reaction under Ar flow. Intermediate (8) (0.00187 mol) was dissolved in degassed TFA (15 ml), then stirred for 4 hours at 85° C. The mixture was cooled. The solvent was evaporated in vacuo. The residue was taken up into degassed toluene. The organic layer was separated, washed with a degassed aqueous NaHCO$_3$ solution (2×50 ml), dried, filtered and the solvent was evaporated in vacuo to give a yellow foam (*). Under Ar, 4-bromo-5-fluoro-2-methoxypyridine (1.3 equiv.; 0.500 g)

was dissolved in degassed dioxane (10 ml). $Cs_2CO_3$ (0.914 g) was added to give suspension (**). A solution of the crude residual oil (*) in degassed dioxane (10 ml) was added to the suspension (**). Then, $Pd_2(dba)_3$ (0.029 g) and Xantphos (0.032 g) were added. The resultant brown reaction suspension was stirred overnight at 100° C. The reaction mixture was cooled, and the solvent was evaporated. The residue was dissolved in ethyl acetate, then washed with an aqueous $NaHCO_3$ solution, and once with brine. The organic layer was separated, dried, filtered and the solvent was evaporated. The residue was purified by column chromatography over silica gel. The product fractions were collected and the solvent was evaporated, yielding 0.5113 g of intermediate (40).

EXAMPLE A.19 a) Preparation of

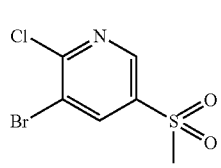

intermediate (139)

A mixture of $NaHCO_3$ (0.570 g) and sodium sulfite (0.800 g) in water (15 ml) was stirred. A solution of 5-bromo-6-chloro-3-pyridinesulfonyl chloride (0.005 mol) in THF (10 ml) was added. The resultant mixture was stirred for 2 hours at 75° C. Then, the mixture was cooled to 30° C. Iodomethane (1.4 ml) was added and the resultant reaction mixture was stirred overnight at 50° C., then cooled, taken up into ethyl acetate, washed with water and the layers were separated. The aqueous phase was extracted once more with ethyl acetate. The organic layers were combined, dried ($MgSO_4$), filtered and the solvent was evaporated, yielding 1.400 g of intermediate (139).

b) Preparation of

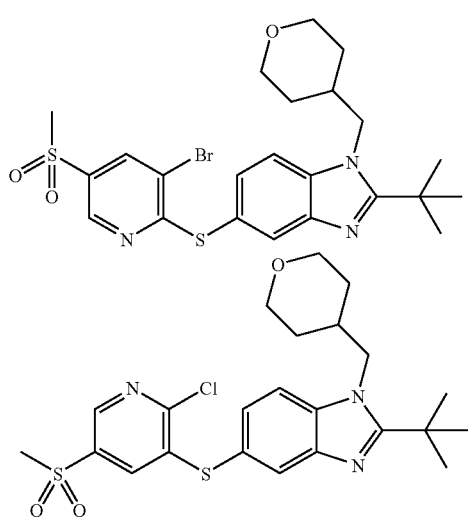

intermediate (41)

$Cs_2CO_3$ (0.00307 mol) was added to intermediate (139) (0.003 mol) in dioxane (10 ml). The mixture was degassed ((3×) vacuum, followed by $N_2$ inlet). A degassed solution of intermediate (9) (0.0023 mol) in dioxane (10 ml) was added. The reaction mixture was degassed once more. $Pd_2(dba)_3$ (0.047 g) and Xantphos (0.060 g) were added. The reaction mixture was stirred overnight at 100° C. The reaction mixture was cooled. DCM (150 ml) was added. The organic layer was washed with water (150 ml). The aqueous layer was extracted again with DCM (150 ml). The combined organic layers were dried ($MgSO_4$), filtered and the solvent was evaporated. The residue was purified by reversed-phase HPLC (gradient elution with $NH_4HCO_3$ buffer (0.25% in water)/$CH_3OH$/$CH_3CN$). The product fractions were collected and the solvent was evaporated, yielding 0.83 g of intermediate (41) as a mixture of two compounds.

EXAMPLE A.20

Preparation of

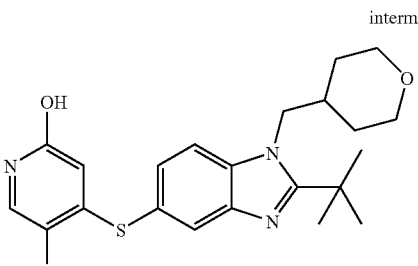

intermediate (42)

4-Bromo-5-fluoro-2(1H)-pyridinone (0.0026 mol) was dissolved in degassed dioxane (10 ml). $Cs_2CO_3$ (0.00325 mol) was added. A solution of intermediate (9) (0.002167 mol) in dioxane (10 ml) was added and the mixture was stirred. Xantphos (0.040 g) and $Pd_2(dba)_3$ (0.120 g) were added and the resultant reaction mixture was stirred for 2 hours. The solvent was evaporated in vacuo. The residue was partitioned between chloroform (100 ml) and water (2×75 ml). The organic layer was separated, washed with brine (75 ml), dried ($Na_2SO_4$), filtered and the solvent was evaporated (vacuum pump). The residue was purified by column chromatography over silica gel (eluent: ethyl acetate/$CH_3OH$ 9/1). The product fractions were collected and the solvent was evaporated, yielding 0.474 g of intermediate (42).

EXAMPLE A.21 a) Preparation of

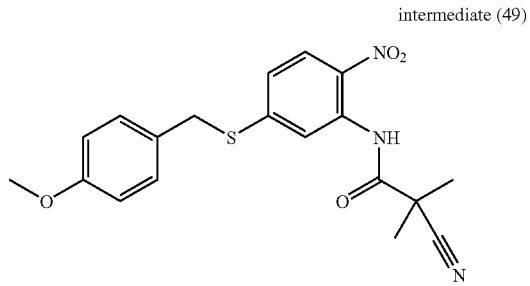 [SMILES: COc1ccc(CSc2ccc([N+](=O)[O-])c(NC(=O)C(C)(C)C#N)c2)cc1]

intermediate (49)

Reaction under nitrogen flow. Phosphoric trichloride (21 ml) was added drop wise to a mixture at 0° C. of intermediate (1) (0.13 mol) and 2-cyano-2-methyl-propanoic acid (0.17 mol) in pyridine (600 ml) while stirring vigorously at 0° C.

The reaction mixture was allowed to warm up to room temperature. Water (1500 ml) was added. This mixture was extracted with ethyl acetate. The separated organic layer was dried (MgSO₄), filtered and the solvent was evaporated, yielding 44g of intermediate (49).

b) Preparation of

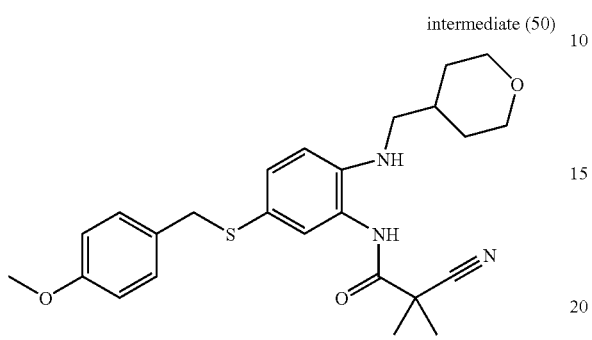

intermediate (50)

A mixture of intermediate (49) (0.010 mol) in THF (100 ml) was hydrogenated at room temperature with a mixture of palladium of activated carbon (10%) and vanadium pentoxide (0.5%) (5g) as a catalyst in the presence of a thiophene in DIPE solution (4%) (1 ml). After uptake of hydrogen (3 equivalents), the catalyst was filtered off and the filtrate was diluted with methanol (300 ml). Acetic acid (2 ml) and then tetrahydro-2H-pyran-4-carboxaldehyde (0.015 mol) were added to the mixture. Nitrogen was bubbled through the reaction mixture for 10 minutes. Sodium cyanotrihydroborate (400 mg) was added to the reaction mixture. The reaction mixture's solvent was evaporated to 1/3 of original volume. DCM (700 ml) and water (500 ml) was added to the concentrate. After extraction, the separated organic layer was dried (MgSO₄), filtered and the solvent was evaporated, yielding 4.5 g of intermediate (50).

c) Preparation of

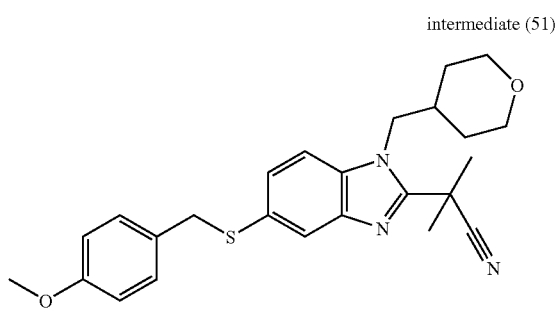 [SMILES: COc1ccc(CSc2ccc3c(c2)nc(C(C)(C)C#N)n3CC2CCOCC2)cc1]

intermediate (51)

Intermediate (50) (0.0066 mol) in acetic acid (15 ml) was heated in a microwave at 160° C. for 10 minutes. The solvent was evaporated. The reaction was performed 8 times). All residues were combined and then taken up in DCM. This mixture was washed with H₂O/NaHCO₃. After extraction, the separated organic layer was dried (MgSO₄), filtered and the solvent was evaporated. The residue was purified by combiflash column chromatography over silica gel (eluent: DCM/CH₃OH from 100/0 to 98/2). The product fractions were collected and the solvent was evaporated, yielding 10.5 g of intermediate (51).

d) Preparation of

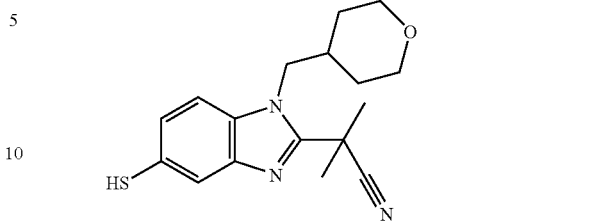

intermediate (52)

Intermediate (51) (0.0023 mol) in TFA (10 ml) was heated in a microwave at 150° C. for 15 minutes. The reaction mixture was cooled and the solvent was evaporated. The residue was taken up in ethyl acetate and water and then neutralized with NaHCO₃. After extraction, the separated organic layer was dried (MgSO₄), filtered and the solvent was evaporated. This procedure was repeated another 2 times, resulting in a combined residue, yielding 3 g of intermediate (52).

e) Preparation of

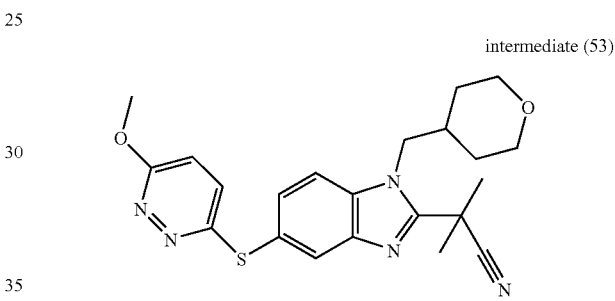

intermediate (53)

First Pd₂(dba)₃ (200 mg), then Xantphos (130 mg) and finally Cs₂CO₃ (0.003 mol) were added to a mixture of 3-chloro-6-methoxypyridazine (0.007 mol) in dioxane (10 ml) in a sealed tube and degassed. Intermediate (52) (0.0023 mol; theoretical, crude) was added and again the reaction mixture was degassed with N₂. The reaction mixture was stirred for 2 hours at 100° C. The reaction mixture was cooled and then filtered. The filtrate's solvent was evaporated. The residue was purified by combiflash column chromatography over silica gel (eluent: DCM/CH₃OH from 100/0 to 99/1). The product fractions were collected and the solvent was evaporated, yielding 0.310 g of intermediate (53).

EXAMPLE A.22

Preparation of

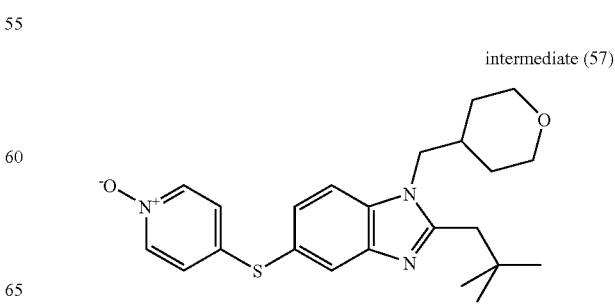

intermediate (57)

4-Chloropyridine N-oxide (0.010 mol) and cesium carbonate (0.008) were added to a mixture of intermediate (14) (0.0042 mol) in dioxane (50 ml). The reaction mixture was degassed with nitrogen and stirred at reflux for 4 hours. The reaction mixture was filtered over dicalite. The filtrate's solvent was evaporated and the residue was dried, yielding 3g of intermediate (57).

EXAMPLE A.23 a) Preparation

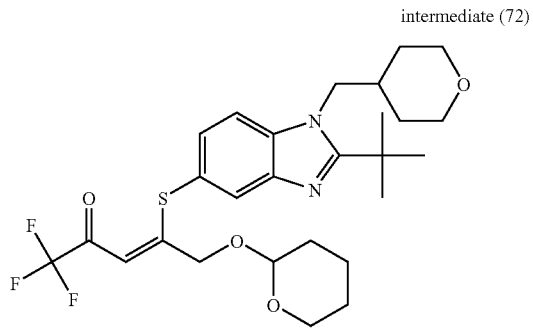

intermediate (72)

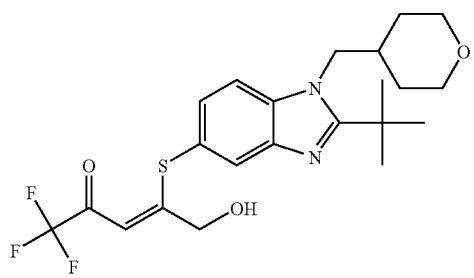

Reaction under inert argon atmosphere. Intermediate (8) (0.5 g, 0.00117 mol) was dissolved in TFA (98%) (10 ml) and the mixture was heated overnight at 80° C. The resulting brown solution was concentrated in vacuo and the residue was taken up in degassed toluene. The organic layer was washed with NaHCO₃ (saturated),dried (Na₂SO₄) and the solvent was evaporated to yield a thick yellow oil. This oil was dissolved in THF (5 ml) and this mixture was added drop wise to a solution of 1,1,1-trifluoro-5-[(tetrahydro-2H-pyran-2-yl)oxy]-3-pentyn-2-one (0.333 g, 1.2 eq) in THF (5 ml). The yellow mixture was then stirred for 2 hours at room temperature and then first PPTS (0.03 g, 0.1 eq) and then ethanol (10 ml) were added. The reaction mixture was stirred at room temperature and an additional amount of PPTS (0.4 eq) was added. The mixture was heated for 3 hours at 60° C. Then the solvent was evaporated and the residue was taken up in chloroform. The organic layer was washed with NaHCO₃ (saturated), water and brine, dried (Na₂SO₄) and the solvent was evaporated, yielding a brown foam. The crude product was purified by column chromatography over silica gel (eluent: ethyl acetate/hexane 3/2). The desired fractions were collected and the solvent was evaporated, yielding 0.16 g of intermediate (72) as mixture of two products.

b) Preparation of intermediate (73)

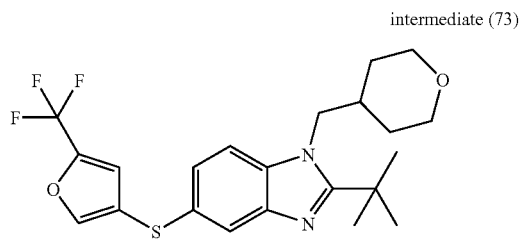 [SMILES: CC(C)(C)c1nc2cc(Sc3coc(C(F)(F)F)c3)ccc2n1CC1CCOCC1]

Intermediate (72) (0.123 g; crude) was dissolved in DCM (4 ml) and the solution was cooled to 0° C. A solution of hydrobromic acid (33%) in glacial acetic acid was added dropwise (the yellow mixture turned to slightly brown). Then the reaction mixture was kept at 0° C. for 2 hours and then the mixture was quenched with NaHCO₃ (saturated). The crude product was extracted with DCM. The separated organic layer was washed with water and brine, dried (Na₂SO₄) and the solvent was evaporated to yield a brown foam. The crude product was purified by column chromatography over silica gel (eluent: hexane/ethyl acetate 1/1). The desired fractions were collected and the solvent was evaporated, yielding 0.044 g of intermediate (73).

EXAMPLE A.24 a) Preparation of intermediate (59)

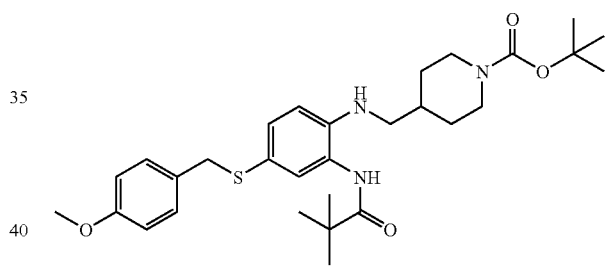

To a mixture of intermediate (3) (0.0290 mol) in acetic acid (250 ml) were added 4-formyl-1-piperidinecarboxylic acid, 1,1-dimethylethyl ester (0.0468 mol), acetic acid (2 ml) and titanium (IV) isopropoxide (4:1) (3g). The reaction mixture was stirred for 20 minutes. Then sodium cyanotrihydroborate (0.03 mol) was added. The reaction mixture was stirred for 2 hours. Water was added to the reaction mixture. The organic layer was dried (MgSO₄), filtered and evaporated, yielding 120g of intermediate (59).

b) Preparation of intermediate (60)

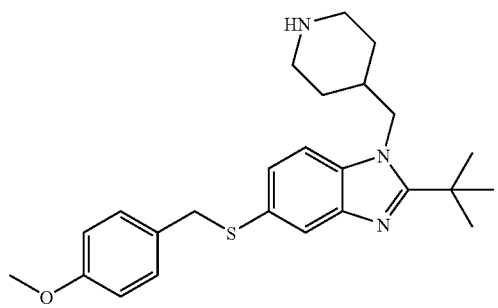

A mixture of intermediate (59) (0.071 mol), acetic acid (800 ml) and hydrochloric acid (40 ml) was stirred at reflux overnight. The reaction mixture was concentrated. The residue was taken up in DCM and water. Then the mixture was neutralized with NaHCO₃. The organic layer was dried (MgSO₄), filtered and evaporated. The residue was used as such in the next reaction, yielding 35g of intermediate (60).

c-1) Preparation of intermediate (61)

A mixture of intermediate (60) (0.071 mol), acetic acid, 1,1'-anhydride (0.14 mol) and DCM (700 ml) was stirred at room temperature for 3 hours. An aqueous NaHCO₃ solution was added and the mixture was stirred for 1 hour to destroy excess acetic acid, 1,1'-anhydride. The organic layer was dried (MgSO₄), filtered and evaporated. The residue was used as such in the next reaction, yielding 35g of intermediate (61).

c-2) Preparation of intermediate (65)

A mixture of intermediate (60) (0.026 mol) in formic acid, methyl ester (300 ml) was stirred and refluxed overnight. The reaction mixture was cooled and the solvent was evaporated. Toluene was added and azeotroped on the rotary evaporator, yielding 12 g of intermediate (65).

d) Preparation of intermediate (62)

A mixture of intermediate (61) (0.01 mol) and TFA (40 ml) was stirred in the microwave at 100° C. for 25 minutes. The reaction mixture was cooled. The solvent was evaporated. The residue was taken up in ethyl acetate and then washed with a water/NaHCO₃ solution. The organic layer was dried (MgSO₄), filtered and evaporated. The crude residue was used in the next step, yielding 4.7 g of intermediate (62).

e-1) Preparation of intermediate (63)

N₂ atmosphere. A mixture of intermediate (62) (0.0021 mol), 5-bromo-2-thiophene-carbonitrile (0.004 mol), Xantphos (0.1 g) and Pd₂(dba)₃ (0.13 g) in 1,4-dioxane (20 ml) was degassed. DIPE was added and the reaction mixture was degassed again. The reaction mixture was stirred at 80-90° C. for 2 hours. After cooling, the reaction mixture was filtered over dicalite. The filtrate was concentrated and the residue was purified on silica gel using DCM/CH₃OH (7N NH₃) (from 100% to 99/1) as eluent. The product fractions were collected and evaporated to dryness. The residue was used as such in the next reaction, yielding 0.45 g of intermediate (63).

e-2) Preparation of intermediate (64)

N₂ atmosphere. A mixture of intermediate (62) (0.004 mol), 4-iodo-1-methyl-1H-pyrazole (0.0035 mol), 1,4-dioxane (25 ml) and Cs₂CO₃ (1.6 g) in Xantphos (0.1 g) was degassed. Pd₂(dba)₃ (0.13 g) was added and the reaction mixture was degassed again. The reaction mixture was stirred at 80-90° C. for 2 hours. After cooling, the reaction mixture was filtered over dicalite. The filtrate was concentrated and the residue was purified on silica gel using DCM/CH₃OH (from 100% to 96/4) as eluent. The product fractions were collected and evaporated to dryness. The residue was used as such in the next reaction, yielding 0.14 g of intermediate (64).

f) Preparation of

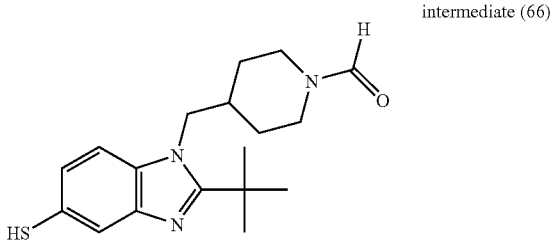 [SMILES: CC(C)(C)c1nc2cc(S)ccc2n1CC1CCN(C=O)CC1]
intermediate (66)

A mixture of intermediate (65) (0.00155 mol) in TFA (18 ml) was stirred at 100° C. for 25 minutes in a microwave oven. The reaction mixture was concentrated. The residue was partitioned between an aqueous NaHCO₃ solution and ethyl acetate. The organic layer was separated, dried (MgSO₄), filtered and the solvent was evaporated, yielding ±0.7 g of intermediate (66).

g) Preparation of intermediate (67)

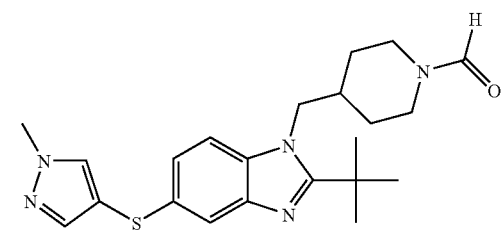

To a mixture of 4-iodo-1-methyl-1H-pyrazole (0.003 mol) and Cs₂CO₃ (1 g) was added 10 ml dioxane. The mixture was degassed by applying alternating N₂ atmosphere and vacuum. Intermediate (66) (0.0022 mol) was added in 10 ml dioxane, and degassed as above. Pd₂(dba)₃ (0.1 g) and Xantphos (0.13 g) were added, degassed again, and the reaction mixture was stirred under a N₂-atmosphere at 100° C. overnight. The reaction mixture was cooled, 150 ml water added, and extracted with 2 times with 150 ml of DCM. The combined organic layer was dried (MgSO₄), filtered, and evaporated. The residue was purified by HPLC (HPLC method A). The residue was crystallized from DIPE, yielding 0.195 g of intermediate (67).

EXAMPLE A.25 a) Preparation of intermediate (68)

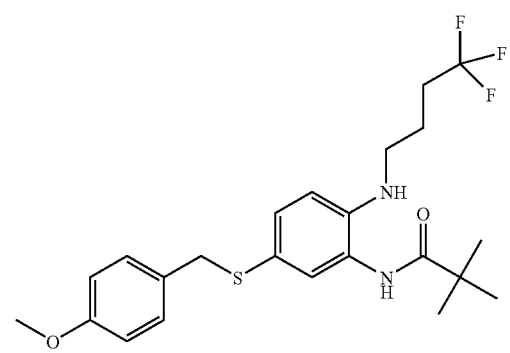

A mixture of intermediate (3) (0.03 mol) and acetic acid (5.2 ml) in DCM (500 ml) was stirred at room temperature under N₂-bubbling. 4,4,4-Trifluorobutanal was added. After 15 minutes NaBH₃(CN) was added and the reaction mixture was stirred for another hour. Water was added and the reaction mixture was extracted. The separated organic layers were collected, dried (MgSO₄), filtered and the filtrate was evaporated. The residue was suspended in DIPE, yielding intermediate (68).

b) Preparation of intermediate (69)

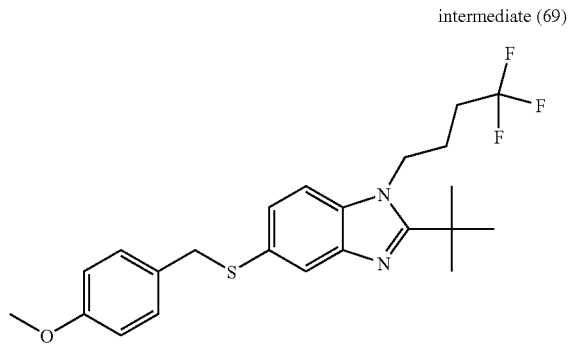 [SMILES: COc1ccc(CSc2ccc3c(c2)nc(C(C)(C)C)n3CCCC(F)(F)F)cc1]

Intermediate (68) (0.04 mol) was dissolved in acetic acid (100 ml). The reaction mixture was stirred and refluxed overnight and the solvent was evaporated. The residue was extracted (DCM/NaHCO₃), dried, filtered and the solvent was evaporated. The concentrate was suspended in DIPE and the precipitate was filtered off and dried, yielding intermediate (69).

c) Preparation of intermediate (70)

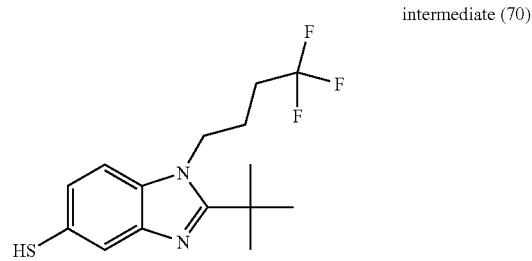 [SMILES: CC(C)(C)c1nc2cc(S)ccc2n1CCCC(F)(F)F]

Reaction was performed in microwave Intermediate (69) was dissolved in TFA. The reaction mixture was stirred for 30 minutes at 100° C. (10% starting material left). The mixture was stirred again for 30 minutes at 100° C. The solvent was evaporated and the residue was extracted (ethyl acetate/NaHCO₃), dried (MgSO₄), filtered and evaporated. The concentrate was used crude, yielding intermediate (70).

d) Preparation of intermediate (71)

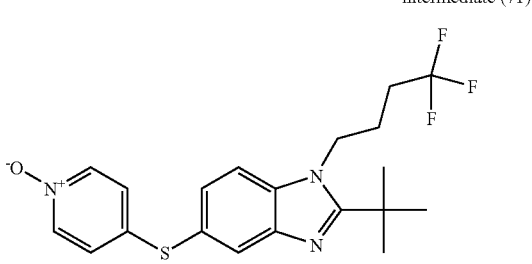

A mixture of 4-chloropyridine, 1-oxide (0.0025 mol), Pd₂(dba)₃ (catalytic quantity), Xantphos (catalytic quantity) and Cs₂CO₃ (0.973 g) in dioxane (5 ml) was degassed by applying alternating N₂ atmosphere and vacuum. Intermediate (70) (0.0023 mol) in dioxane (15 ml) was added under N₂-atmosphere. The reaction mixture was stirred at 100° C. for 2 hours. The mixture was extracted (DCM/H₂O), dried, filtered and evaporated. The residue was used crude, yielding intermediate (71).

EXAMPLE A.26 a) Preparation of

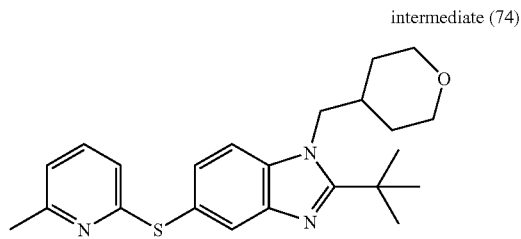 [SMILES: Cc1cccc(Sc2ccc3c(c2)nc(C(C)(C)C)n3CC2CCOCC2)n1]

intermediate (74)

Reaction recipients made inert with N₂. A mixture of intermediate (8) (0.002355 mol) in TFA (14 ml) was heated at reflux overnight. The solvent was evaporated. Degassed NaHCO₃ saturated aqueous solution (50 ml) and degassed toluene (80 ml) were added to the residue. The layers were separated in organic layer OL1 and in aqueous layer AL1. AL1 was 3 times re-extracted with toluene (40 ml) to obtain 3 separated organic layers OL2, OL3 and OL4. OL1, OL2, OL3 and OL4 were combined and was dried (Na₂SO₄), filtered and the solvent was evaporated (vacuum, 1 hour) to obtain residue A. The reaction recipients were made inert with N₂. Cs₂CO₃ (0.00471 mol; dried in vacuo) was added to a solution of 2-chloro-6-methylpyridine(0.003062 mol) dissolved in DMSO (14 ml) to obtain mixture A. Then residue A in DMSO (14 ml) was added to the mixture A. The reaction mixture was degassed for 15 minutes and then refluxed for 150 minutes. Ethyl acetate was added to the residue. This mixture was washed 4 times with water (125 ml) and 1 time with NaCl (100 ml). The separated organic layer was dried (Na₂SO₄), filtered and the solvent was evaporated. The residue was purified by column chromatography over silica gel (eluent: ethyl acetate/hexane 50/50 and 60/40). The product fractions were collected and the solvent was evaporated, yielding 0.097 g of intermediate (74).

b) Preparation of

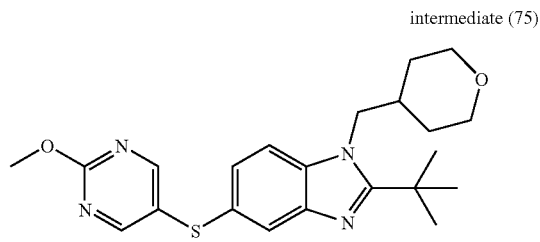 [SMILES: COc1ncc(Sc2ccc3c(c2)nc(C(C)(C)C)n3CC2CCOCC2)cn1]

intermediate (75)

Reaction recipients made inert with N₂. A mixture of intermediate (8) (0.002355 mol) in TFA (14 ml) was stirred overnight at reflux. The solvent was evaporated. The residue was taken up in degassed toluene (80 ml) and in degassed NaHCO₃ saturated aqueous solution (50 ml). The layers were separated in organic layer OL1 and in aqueous layer AL1. AL1 was 3 times re-extracted with toluene (40 ml) to obtain 3 separated organic layers OL2, OL3 and OL4. OL1, OL2, OL3 and OL4 were combined and was dried (Na₂SO₄), filtered and the solvent was evaporated (vacuum, 1 hour) to obtain residue A.

Reaction recipients made inert with N₂. Cs₂CO₃ (0.002037 mol; dried in vacuo) was added to a suspension of 5-bromo-2-methoxypyrimidine (0.003062 mol) in degassed dioxane (14 ml) to obtain mixture A. Then residue A in degassed dioxane (14 ml) was added to the mixture A. Finally Pd₂(dba)₃ (0.036 g), Xantphos (0.079 g) and then potassium fluoride (0.000479 mol) were added and the reaction mixture was degassed for 15 minutes. The reaction mixture was stirred at reflux for 19 hours. The solvent was evaporated. Chloroform was added to the residue. The mixture was washed 2 times with water and then 1 time with NaCl saturated aqueous solution. The separated organic layer was dried (Na₂SO₄), filtered and the solvent was evaporated. The residue was purified by column chromatography over silica gel (eluent: ethyl acetate/hexane 50/50 and 60/40). The product fractions were collected and the solvent was evaporated, yielding 0.255 g of intermediate (75).

EXAMPLE A.27 a) Preparation of

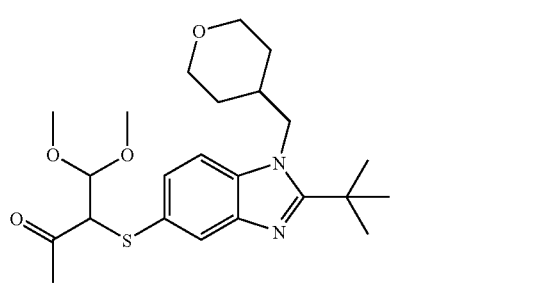

intermediate (79)

Reaction under dry conditions and inert N₂ atmosphere. A mixture of intermediate (8) (1.5 g, 0.003553 mol) in TFA (20 ml) was refluxed overnight. The reaction mixture was evaporated and an extraction procedure was done with NaHCO₃ (degassed saturated solution) and toluene (4×, degassed). The separated organic layer was dried (Na₂SO₄), filtered and the solvent was evaporated, yielding residue (1). The residue (1) was divided in 2 parts and each part was further treated in a different way.

Reaction A:
The first part of residue (1) was reacted with 3-bromo-4,4-dimethoxy-2-butanone (0.450 g) in DMF (8 ml; dry) at 0° C. Sodium hydride (60%) (0.051 g) was added. The mixture was reacted for 30 minutes at 0° C. and then the mixture was warmed up to room temperature.

Reaction B: The second part of residue (1) was dissolved in DMF (3 ml; dry). A suspension of sodium hydride (60%) (0.051 g) in DMF (2 ml; dry) was added at to the solution at 0° C. The mixture was reacted for 30 minutes at 0° C. and subsequently a solution of 3-bromo-4,4-dimethoxy-2-butanone (0.450 g) in DMF (3 ml; dry) was added. The reaction mixture was reacted for 15 minutes at 0° C. and was then warmed up to room temperature.

Both reaction mixtures A and B were extracted with ethyl acetate, NaHCO₃ (saturated solution) and water. The separated organic layer was dried (Na₂SO₄), filtered and the solvent was evaporated, yield 0.76 g crude product from reaction A and 0.74 g crude product from reaction B. Both crude products from reaction A and reaction B were combined and were purified by column chromatography over silica gel (eluent: ethyl acetate/hexane first 1/1, then 7/3). The desired fractions were collected and the solvent was evaporated, yielding intermediate (79).

b) Preparation of

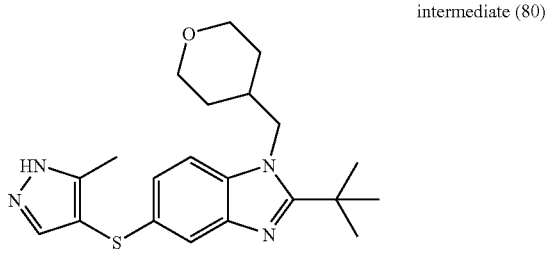 [SMILES: Cc1[nH]ncc1Sc1ccc2c(c1)nc(C(C)(C)C)n2CC1CCOCC1]

intermediate (80)

Hydrazine dihydrochloride (0.181 g, 0.001728 mol) was added to a solution of intermediate (79) (0.075 g, 0.000173 mol) and ethanol (4.5 ml) in a sealed tube and the reaction mixture was heated at 70-80° C. Subsequently, the mixture was evaporated and an extraction was done with chloroform, NaHCO$_3$ (saturated solution) and water. The separated organic layer was dried (MgSO$_4$), filtered and the solvent was evaporated, yielding 0.075 g of the crude product. The crude was purified by preparative HPLC, yielding 0.057 g of intermediate (80).

EXAMPLE A.28

Preparation of

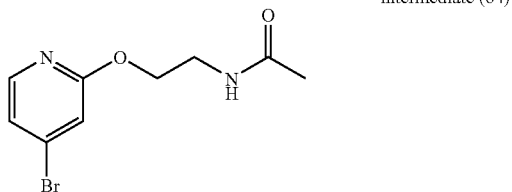

intermediate (84)

A mixture of N-(2-hydroxyethyl)acetamide (1g), dioxane (10 ml) and sodium hydride (60%)(0.46 g.) was stirred for 30 minutes at 60° C. The reaction mixture was cooled. 4-Bromo-2-fluoropyridine (1g) was added, and the reaction mixture was stirred for 90 minutes at 110° C. The reaction mixture was poured into 100 ml aq. sat. NH$_4$Cl. The resulting precipitate was isolated by filtration, washed with water and dried in vacuo, yielding 1.16 g of intermediate (84).

EXAMPLE A.29 a) Preparation of

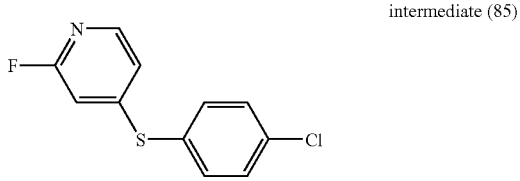 [SMILES: Fc1cc(Sc2ccc(Cl)cc2)ccn1]

intermediate (85)

A mixture of 4-bromo-2-fluoropyridine (1.1 equiv.), Pd$_2$(dba)$_3$ (1.7 g), Xantphos (2.2 g) and Cs$_2$CO$_3$ (33g) in dioxane (q.s.) was degassed. A mixture of 4-chlorobenzenethiol (0.062 mol) in dioxane (q.s.) was added. The reaction mixture was stirred overnight at 100° C. under N$_2$ atmosphere. The mixture was filtered and the filtrate's solvent was evaporated. The residue was partitioned between DCM and water. The organic layer was separated, dried, filtered and the solvent evaporated. The residue was purified by flash column chromatography over silica gel (eluent: hexane/DCM 60/40). The product fractions were collected and the solvent was evaporated, yielding intermediate (85).

b) Preparation of

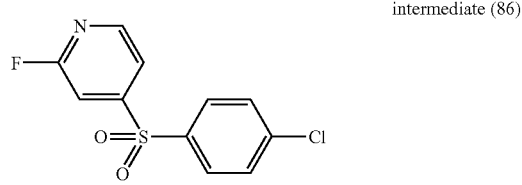 [SMILES: O=S(=O)(c1ccc(Cl)cc1)c1ccnc(F)c1]

intermediate (86)

3-Chlorobenzenecarboperoxoic acid (20g) was added to a mixture of intermediate (85) (0.042 mol) in chloroform. The reaction mixture was stirred for 30 minutes at room temperature. This mixture was partitioned between DCM and an aqueous NaOH solution (2×). The organic layer was separated, then filtered through Extrelut. The filtrate's solvent was evaporated. The residue was stirred in DIPE, filtered off and dried, yielding intermediate (86).

c) Preparation of

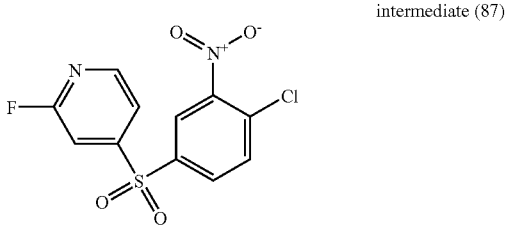 [SMILES: O=[N+]([O-])c1cc(S(=O)(=O)c2ccnc(F)c2)ccc1Cl]

intermediate (87)

A mixture of intermediate (86) (0.011 mol) in sulphuric acid (conc.) (35 ml) was stirred and cooled to 0° C. A mixture of sulphuric acid (conc.) and nitric acid (conc.) (1/1) (5.6 ml) was added dropwise at 0° C. The resultant reaction mixture was stirred for 3 hours at room temperature, then poured out into ice-water. This mixture was extracted with DCM. The separated organic layer was dried (MgSO$_4$), filtered and the solvent evaporated. The residue was suspended in DIPE, filtered off and dried (vacuum, 40° C.), yielding 1.7 g of intermediate (87).

d) Preparation of

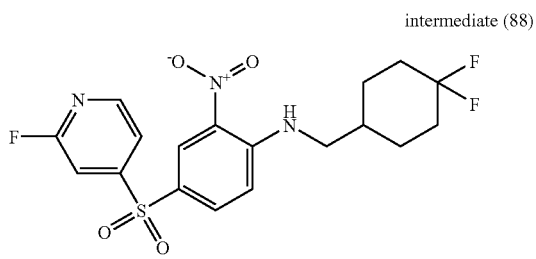

intermediate (88)

4,4-Difluoro-cyclohexanemethanamine, trifluoroacetate (crude, 2 equiv.) in some DMSO was added to a mixture of intermediate (87) (0.0025 mol, 0.800 g) and N-ethyl-N-(1-methylethyl)-2-propanamine (0.834 ml) in DMSO (50 ml). The mixture was stirred for 24 hours at 50° C. Water was added. This mixture was extracted with ethyl acetate. The separated organic layer was dried, filtered, and the solvent was evaporated. The residue was purified by reversed-phase HPLC (gradient elution with (NH$_4$OAc 0.5% in water/CH$_3$CN 90/10)/CH$_3$OH/CH$_3$CN). The pure fractions were collected. The organic solvent was evaporated. The aqueous concentrate was extracted. The separated organic layer was dried, filtered and the solvent evaporated, yielding 0.129 g of intermediate (88).

e) Preparation of

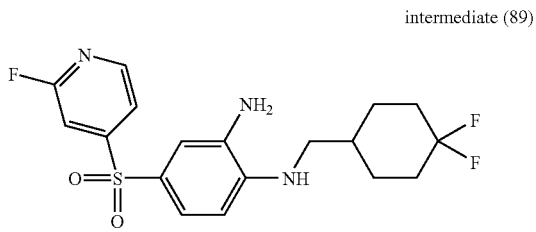 [SMILES: Nc1cc(S(=O)(=O)c2ccnc(F)c2)ccc1NCC1CCC(F)(F)CC1]

intermediate (89)

A mixture of intermediate (88) (0.13 g, 0.0003 mol) in methanol (50 ml) was hydrogenated with a mixture of platinum on activated carbon (5%) and vanadium pentoxide (0.5%) (0.1 g) as a catalyst catalyst in the presence of a thiophene solution (0.1 ml). After uptake of hydrogen (3 equivalents), the catalyst was filtered off and the filtrate was evaporated, yielding intermediate (89).

f) Preparation of

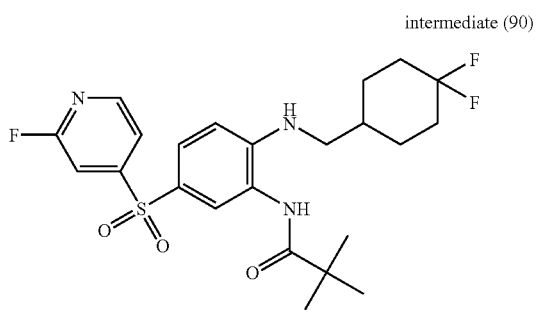 [SMILES: CC(C)(C)C(=O)Nc1cc(S(=O)(=O)c2ccnc(F)c2)ccc1NCC1CCC(F)(F)CC1]

intermediate (90)

Intermediate (89) (0.00024 mol, crude) was dissolved in a mixture of DCM (5 ml) and triethylamine (0.040 ml). 2,2-Dimethylpropanoyl chloride (0.035 ml) was added and the mixture was stirred during 30 minutes at room temperature. This mixture was extracted with DCM. The separated organic layer was washed with water, dried, filtered and the solvent evaporated, yielding intermediate (90).

g) Preparation of

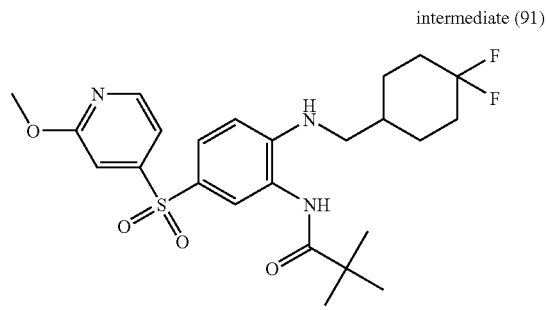 [SMILES: COc1cc(S(=O)(=O)c2ccc(NCC3CCC(F)(F)CC3)c(NC(=O)C(C)(C)C)c2)ccn1]

intermediate (91)

A mixture of intermediate (90) (0.00024 mol, crude) in methanol (3 ml) was treated with sodium hydroxide (50%) (7 drops). The reaction mixture was heated in the microwave oven for 20 minutes at 70° C. The solvent was evaporated, yielding intermediate (91).

EXAMPLE A.30 a-1) Preparation of

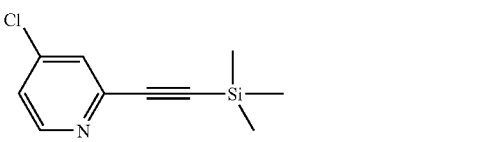

intermediate (93)

2-Bromo-4-chloropyridine (0.0025 mol, 0.5 g), dichloro-bis(triphenylphosphine)-palladium (0.055 g, 0.03 equiv.) and copper iodide (0.015 g, 0.03 equiv.) were combined under N$_2$ flow. Triethylamine (6 ml) and ethynyltrimethylsilane (0.407 ml, 1.1 equiv.) were added at 40° C. The mixture was stirred overnight at 40° C. The reaction was quenched by adding water. The mixture was partitioned between DCM and water. The organic layer was separated, dried (MgSO$_4$), filtered and the solvent was evaporated, yielding intermediate (93).

a-2) Preparation of

intermediate (94)

Intermediate (93) (0.0025 mol) was added to a mixture of potassium hydroxide (0.005 mol, 0.280 g) and methanol (4.25 ml) in DCM (2.25 ml). The reaction mixture was stirred during 2 hours at room temperature. The reaction was quenched with water and subsequently extracted with DCM. The separated organic layer was dried (MgSO$_4$), filtered and the solvent evaporated, yielding intermediate (94).

b) Preparation of

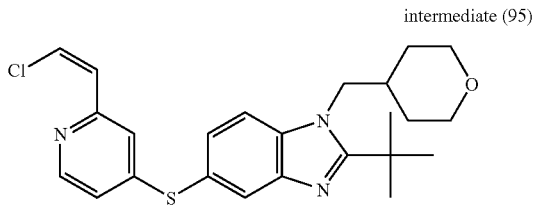 [SMILES: CC(C)(C)c1nc2cc(Sc3ccnc(/C=C\Cl)c3)ccc2n1CC1CCOCC1]

intermediate (95)

A mixture of intermediate (94) (0.0025 mol, crude), Pd$_2$(dba)$_3$ (0.063 g, 0.03 equiv.), Xantphos (0.079 g, 0.06 equiv.) and Cs$_2$CO$_3$ (1.2 g, 1.5 equiv.) in 1,4-dioxane (20 ml) was degassed. Intermediate (9) (0.0023 mol) was added and the mixture was stirred overnight at 100° C. The mixture was cooled and filtered. The filtrate was evaporated. The residue was dissolved in DCM and this mixture was extracted with water. The separated organic layer was dried, filtered, and the solvent was evaporated, yielding intermediate (95).

EXAMPLE A.31 a) Preparation of

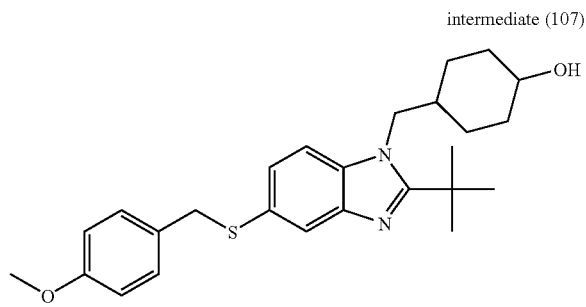 [SMILES: COc1ccc(CSc2ccc3c(c2)nc(C(C)(C)C)n3CC2CCC(O)CC2)cc1]

intermediate (107)

A mixture of intermediate (106) (0.02 mol), NaBH$_4$ (0.28 g) and methanol (100 ml) was stirred at room temperature for 1 hour. The solvent was evaporated. The residue was taken up in DCM and washed with water. The organic layer was dried (MgSO$_4$), filtered and evaporated, yielding 0.6 g of intermediate (107).

b) Preparation of

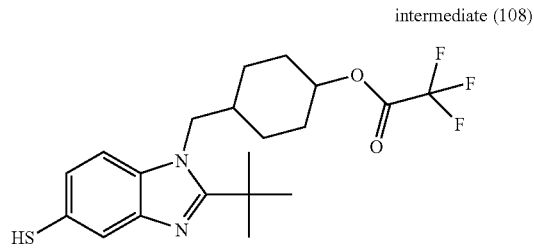 [SMILES: CC(C)(C)c1nc2cc(S)ccc2n1CC1CCC(OC(=O)C(F)(F)F)CC1]

intermediate (108)

Intermediate (107) (0.0013 mol) and TFA (10 ml) were stirred in the microwave at 100° C. for 25 minutes. The reaction mixture was cooled. The solvent was evaporated. The residue was taken up in ethyl acetate and then washed with water/NaHCO$_3$ solution. The organic layer was dried (MgSO$_4$), filtered and evaporated. The crude residue was used in the next step, yielding 0.6 g of intermediate (108).

c) Preparation of

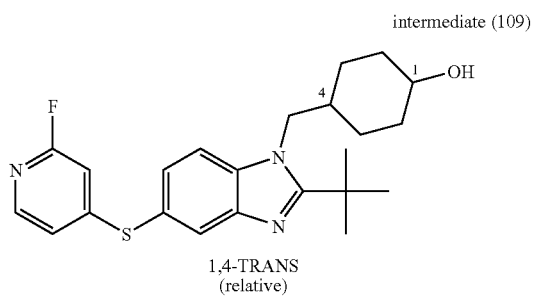 [SMILES: CC(C)(C)c1nc2cc(Sc3ccnc(F)c3)ccc2n1CC1CCC(O)CC1]

intermediate (109)

1,4-TRANS
(relative)

N$_2$ atmosphere. A mixture of intermediate (108) (0.007 mol), 4-bromo-2-fluoropyridine (0.01 mol), Xantphos (0.15 g) and Pd$_2$(dba)$_3$ (0.2 g) in dioxane (50 ml) was degassed. Cs$_2$CO$_3$ (3.3 g) was added and the reaction mixture was degassed again. The reaction mixture was stirred at 90° C. for 1 hour. The reaction mixture was filtered over dicalite. The filtrate was concentrated. The residue was taken up in DCM and washed with water. The organic layer was dried (MgSO$_4$), filtered and evaporated. The residue was purified on the combiflash system (normal phase silica gel) using DCM /CH$_3$OH (100% to 96%/4%) as eluent. The product fractions were collected and evaporated, yielding a residue (1.8 g, mixture of CIS/TRANS 13/80). A part of this residue (0.35 g) of was purified by HPLC (HPLC method C) to separate the CIS/TRANS isomers. The desired product fractions (only the TRANS isomer was used in the next reaction step) were collected and evaporated until complete dryness, yielding 0.14 g of intermediate (109) (1,4-trans isomer (pure)).

EXAMPLE A.32 a) Preparation of

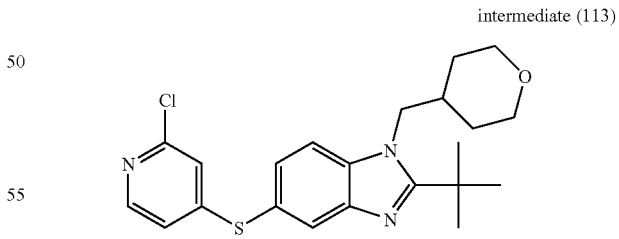

intermediate (113)

N$_2$ atmosphere. A mixture of intermediate (9) (0.014 mol), 4-bromo-2-chloropyridine (0.015 mol), Xantphos (0.42 g) and Pd$_2$(dba)$_3$ (0.6 g) in dioxane (100 ml) was degassed. Cs$_2$CO$_3$ was added and the reaction mixture was degassed again. The reaction mixture was stirred at 80-90° C. for 2 hours. The reaction mixture was cooled and filtered over dicalite. The filtrate was evaporated. The residue was crystallized from DIPE and a little 2-propanol. The solid was filtered off, washed and dried, yielding 3.5 g of intermediate (113).

b) Preparation of

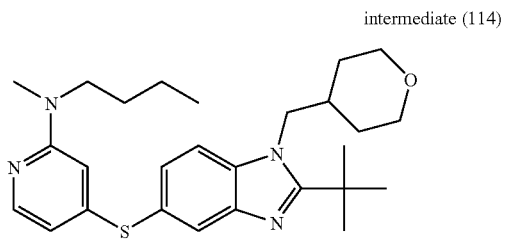 [SMILES: CCCCN(C)c1cc(Sc2ccc3c(c2)nc(C(C)(C)C)n3CC2CCOCC2)ccn1]

intermediate (114)

A mixture of intermediate (113) (0.0005 mol) and N-methyl-1-butanamine (10 ml) were stirred in the microwave for 12 hours at 150° C. The excess of N-methyl-1-butanamine was removed by evaporation. The residue was purified by column chromatography using DCM/MeOH:NH$_3$ (100% to 98%/2%) as eluent. The product fractions were collected and evaporated. The residue was used as such in the next reaction, yielding 0.125 g of intermediate (114).

EXAMPLE A.33 a) Preparation of

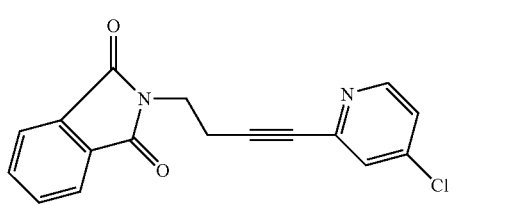

intermediate (115)

Reaction under N$_2$ flow. Et$_3$N (2.5 ml) and then 2-(3-butyn-1-yl)-1H-Isoindole-1,3(2H)-dione (0.0011 mol) were added at 40° C. to a mixture of 2-bromo-4-chloropyridine (0.001 mol), dichlorobis(triphenylphosphine)-palladium (0.022 g) and copper iodide (0.006 g) and stirred for 10 hours at 40° C. The solvent was evaporated. The residue was partitioned between DCM and water. The mixture was filtered over Isolute and the filtrate's solvent was evaporated. The residue was purified by column chromatography (eluent: DCM). The desired product fractions were collected and the solvent was evaporated. The residue was suspended in DIPE and the precipitate was filtered off, yielding 0.200 g of intermediate (115).

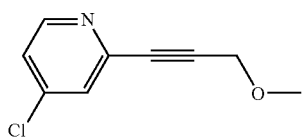

intermediate (128)

Intermediate (128) was prepared in a similar procedure as intermediate (115) starting from 2,4-dichloropyridine and 3-methoxy-1-propyne.

b) Preparation of

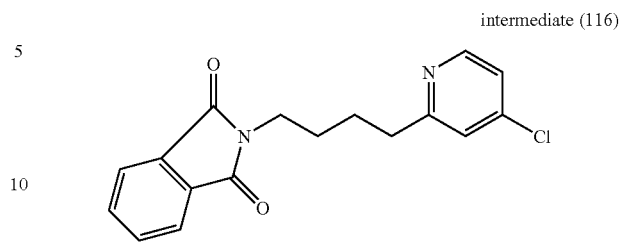

intermediate (116)

A mixture of intermediate (115) (0.0026 mol) in methanol (50 ml) was hydrogenated with a catalyst platinum on activated carbon (5%) and a thiophene (4%) in DIPE solution in the presence triethylamine. After uptake of hydrogen (2 equiv.) the catalyst was filtered off and the solvent was evaporated, yielding 0.5 g of intermediate (116).

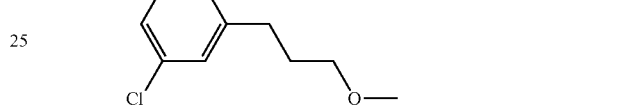

intermediate (129)

Intermediate (129) was prepared in a similar procedure as intermediate (116) starting from intermediate (128). No triethylamine was used in the procedure for intermediate (129).

EXAMPLE A.34 a) Preparation of

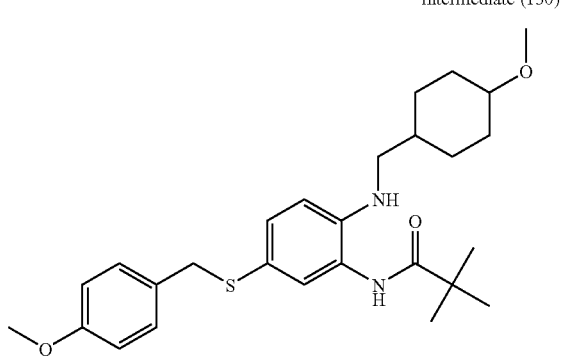

intermediate (130)

This reaction was performed twice.

A mixture of 4-methoxycyclohexanecarboxaldehyde (0.0063 mol) and intermediate (3) (0.0042 mol) was dissolved in ethanol with 1 equiv. hydrogen. After uptake of hydrogen, the reaction mixture was evaporated.

The second time, the reaction was performed with less intermediate (3) (1.23 g). The reaction mixture was extracted (DCM/water). The collected organic layers were dried, filtered and evaporated. Both residues were put together and purified by HPLC (HPLC method A). The desired fractions were collected and the solvent was evaporated, yielding intermediate (30).

b) Preparation of

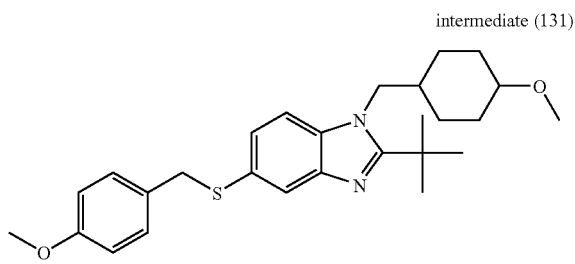
intermediate (131)

A solution of intermediate (130) (0.042 mol) in acetic acid (q.s.) and 1 drop of hydrochloric acid was heated in microwave at 150° C. for 40 minutes. Still some starting material left. Residue was heated again for 25 minutes at 150° C. The solvent was evaporated and residue was extracted (DCM/water). The organic layers were collected, dried (MgSO$_4$), filtered and evaporated. The crude residue was used as such in the next reaction, yielding intermediate (131).

c) Preparation of

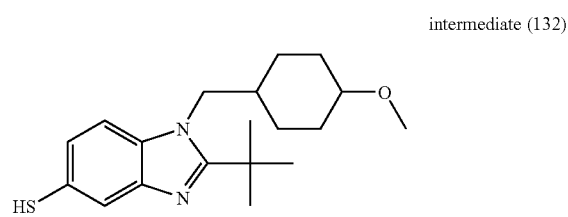 [SMILES: COC1CCC(Cn2c(C(C)(C)C)nc3cc(S)ccc32)CC1]
intermediate (132)

Intermediate (31) (0.0042 mol) was dissolved in TFA (15 ml). The reaction mixture was stirred in microwave at 100° C. for 30 minutes. The reaction mixture was evaporated. The residue was extracted twice (ethyl acetate/NaHCO$_3$). The collected organic layers were dried (MgSO$_4$), filtered and evaporated. The crude residue was used as such in the next reaction, yielding intermediate (132).

d) Preparation

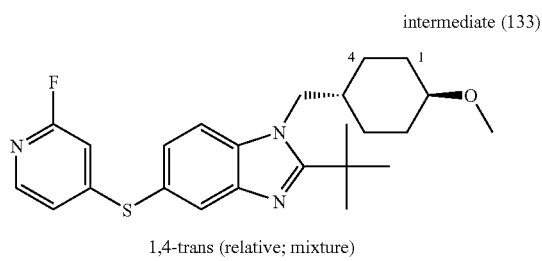 [SMILES: CO[C@H]1CC[C@H](Cn2c(C(C)(C)C)nc3cc(Sc4ccnc(F)c4)ccc32)CC1]
intermediate (133)
1,4-trans (relative; mixture)

and

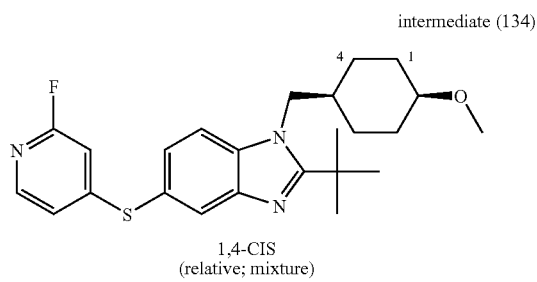 [SMILES: CO[C@H]1CC[C@@H](Cn2c(C(C)(C)C)nc3cc(Sc4ccnc(F)c4)ccc32)CC1]
intermediate (134)
1,4-CIS (relative; mixture)

A mixture of 4-bromo-2-fluoropyridine (0.635 g), Pd$_2$(dba)$_3$ (catalytic quantity), Xantphos (catalytic quantity) and Cs$_2$CO$_3$ (1.5 g) in 1,4-dioxane (5 ml) was degassed by applying alternating N$_2$ atmosphere and vacuum. Intermediate (132) in 1,4-dioxane (15 ml) was added under N$_2$-atmosphere. The reaction mixture was stirred at 100° C. for 2 hours. The reaction mixture was filtrated. After extraction (DCM/water), the collected organic layers were dried (MgSO$_4$), filtered and the filtrate was evaporated. The residue was purified by HPLC (HPLC method A). Two product fraction groups were collected and their solvents were evaporated, yielding intermediate (133) (trans; relative; mixture) and intermediate (134) (cis; relative; mixture).

EXAMPLE A.35

Preparation of

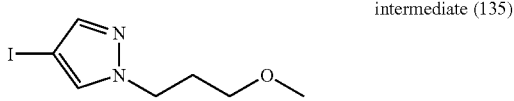
intermediate (135)

Reaction under an inert Ar atmosphere. Sodium hydride (60%) (1.81 g, 1.1 equiv.) was suspended in DMF (60 ml) and the suspension was cooled to 0° C. A solution of 4-iodo-1H-pyrazole (8 g, 0.04124 mol) in DMF (20 ml) was slowly added to the cooled suspension and the reaction mixture was stirred for 30 minutes at 0° C. and then at room temperature for 30 minutes. The mixture was cooled again to 0° C., and potassium iodide (6.8 g, 1 equiv.) was added, followed by the dropwise addition of 1-bromo-3-methoxypropane (9.47 g). The white suspension was stirred for 30 minutes at 0° C. and then at room temperature for 3 hours. The mixture was cooled again to 0° C. and was then quenched with water. The mixture was diluted with ethyl acetate and the organic layer was separated. The organic layer was washed with water and brine, dried (Na$_2$SO$_4$), filtered and the solvent was evaporated in vacuo (pale yellow oil). This oily residue was purified by column chromatography over silica gel (eluent: hexane/ethyl acetate 3/1). The desired fractions were collected and the solvent was evaporated, yielding 9.064 g of intermediate (135).

EXAMPLE A.36 a) Preparation of

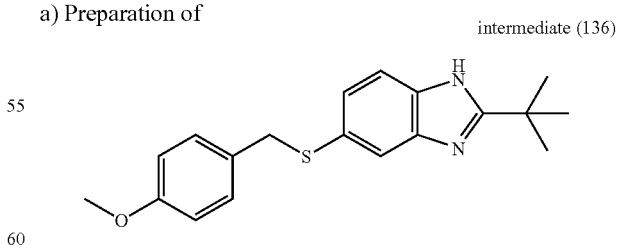
intermediate (136)

A mixture of intermediate (3) (0.05 mol) in acetic acid (400 ml) was stirred and refluxed for 3 hours. The reaction mixture was cooled and then the solvent was evaporated. The residue was extracted in DCM/water. The separated organic layer was dried (MgSO$_4$), filtered and the solvent was evaporated, yielding 6.5 g of intermediate (136).

b) Preparation of

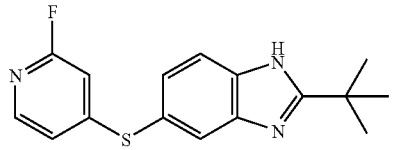
intermediate (137)

Reaction under inert Ar atmosphere.

Intermediate (136) (1 g, 0.00306 mol) was dissolved in TFA (15 ml). The solution was stirred overnight at 100° C. The mixture was cooled and the deep black mixture was concentrated in vacuo. The residue was taken up in ethyl acetate. The organic layer was washed with NaHCO$_3$ (saturated), water and brine, dried (Na$_2$SO$_4$), filtered and the solvent was evaporated (green residue). This green solid was dissolved in dioxane (15 ml) under an inert atmosphere of Ar. 4-Bromo-2-fluoropyridine (0.00306 mol), Cs$_2$CO$_3$ (1.5 g, 1.5 equiv.), Xantphos (0.09 g) and Pd$_2$(dba)$_3$ (0.08 g) were added. The reaction was degassed for 15 minutes and was then heated for 30 minutes at 80° C. The cooled mixture was concentrated in vacuo and the resulting thick brown oil was taken up in chloroform. The organic layer was washed with NaHCO$_3$ (saturated), water and brine, dried (Na$_2$SO$_4$), filtered and the solvent was evaporated to yield a brown solid. This solid was purified by column chromatography over silica gel (eluent: hexane/ethyl acetate 1/1). The desired fractions were collected and the solvent was evaporated, yielding 0.642 g of intermediate (137).

c) Preparation of

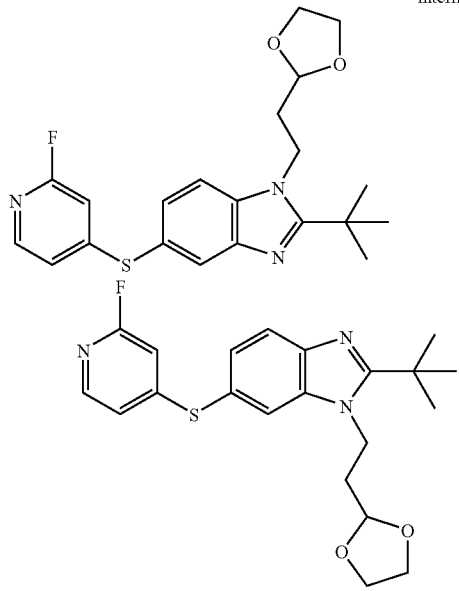
intermediate (138)

= mixture of isomers

Reaction under inert Ar atmosphere.

Intermediate (137) (0.645 g, 0.00214 mol) was dissolved in DMF. 2-(2-Bromoethyl)-1,3-dioxolane (0.002354 mol) was added and subsequently potassium iodide (0.002354 mol) was added. The brown mixture was cooled to 0° C. and sodium hydride (60%) (0.129 g, 1.5 equiv.) was added dropwise. The brown reaction mixture was stirred for 30 minutes at 0° C., and then overnight at room temperature. The mixture was quenched with water and the crude product was extracted with ethyl acetate. The separated organic layer was washed with water and brine, dried (Na$_2$SO$_4$), filtered and the solvent was evaporated, to yield a pale green solid. This solid was taken up in ethyl acetate, and hexane was added. The precipitate (starting material) was filtered off and washed with hexane. The filtrate was concentrated in vacuo. The residue was worked up again, and a second amount of precipitate was filtered off (starting material). The filtrate was evaporated and the residue was purified by column chromatography over silica gel (eluent: hexane/ethyl acetate 1/1). The desired fractions were collected and the solvent was evaporated, yielding 0.302 g of intermediate (138) (mixture of isomers).

EXAMPLE A.37 a) Preparation of

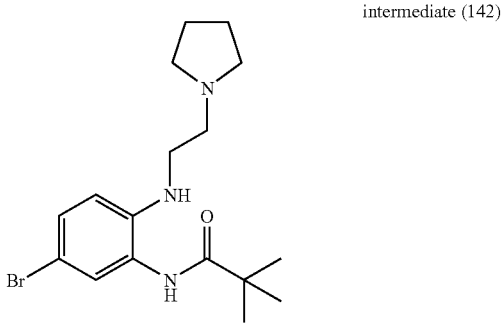 [SMILES: CC(C)(C)C(=O)Nc1cc(Br)ccc1NCCN1CCCC1]
intermediate (142)

A mixture of 4-bromo-N$^1$-[2-(1-pyrrolidinyl)ethyl]-1,2-benzenediamine (0.0350 mol) in DCM (200 ml) was cooled to 0° C. 2,2-Dimethylpropanoyl chloride (0.0350 mol) and then triethylamine (5.8 ml) were added to the reaction mixture and stirred at room temperature for 3 hours. The reaction mixture was washed with water. The separated organic layer was dried (MgSO$_4$), filtered and the solvent was evaporated. The residue was suspended in DIPE, the precipitate was filtered off and dried (vacuo, 40° C.), yielding 8g of intermediate (142).

b) Preparation of

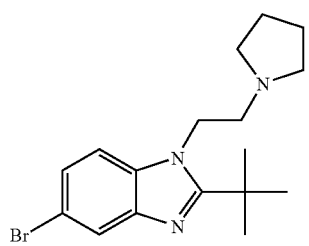
intermediate (143)

A mixture of intermediate (142) (0.0059 mol) in acetic acid (30 ml) was heated for 20 minutes in a microwave at 150° C. The reaction mixture was cooled and the solvent was evaporated. The residue was partitioned between ethyl acetate and water. This mixture was neutralized with an aqueous NaHCO$_3$ solution. The separated organic layer was dried (MgSO$_4$), filtered and the solvent was evaporated, yielding 1.5 g of intermediate (143).

c) Preparation of

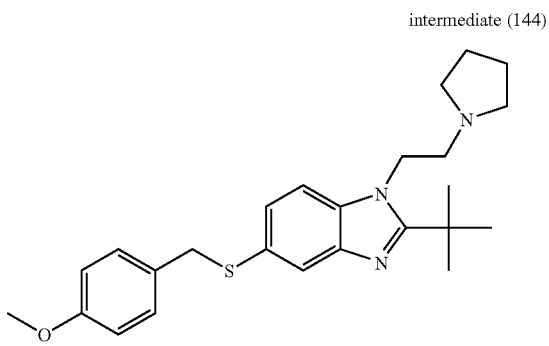 [SMILES: COc1ccc(CSc2ccc3c(c2)nc(C(C)(C)C)n3CCN2CCCC2)cc1]

intermediate (144)

A mixture of intermediate (143) (0.0005 mol), 4-methoxybenzenemethanethiol (0.001 mol), Pd$_2$(dba)$_3$ (0.040 g) and Xantphos (0.040 g) in dioxane (10ml) was degassed. N-ethyl-N-(1-methylethyl)-2-propanamine (0.001 mol) was added and the reaction mixture was degassed again. The reaction mixture was stirred at 100° C. for 20 hours. The reaction mixture was cooled and the solvent was evaporated. The residue was taken up in DCM and water. The separated organic layer was dried (MgSO$_4$), filtered and the solvent was evaporated. The residue was purified by column chromatography (eluent: DCM/methanol 99/1). The desired product fractions were collected and the solvent was evaporated, yielding 1.2 g of intermediate (144).

d) Preparation of

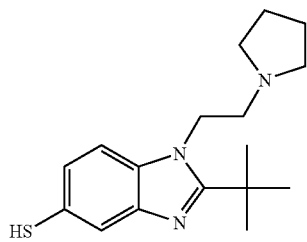

intermediate (145)

A mixture of intermediate (144) (0.0028 mol) in TFA (15 ml) was heated for 20 minutes in a microwave at 120° C. The solvent was evaporated. The residue was partitioned between ethyl acetate and water. This mixture was neutralized with an aqueous NaHCO$_3$ solution. The separated organic layer was dried (MgSO$_4$), filtered and the solvent was evaporated, yielding intermediate (145).

e) Preparation of

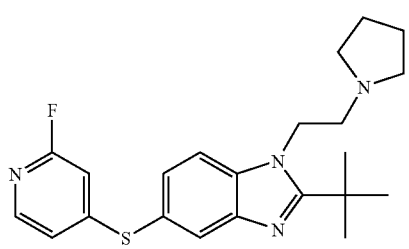

intermediate (146)

A mixture of 4-bromo-2-fluoropyridine(0.0028 mol) and cesium carbonate (1.7 g) in dioxane (10 ml) was degassed. Intermediate (145) (theoretical maximum, crude) in dioxane (10 ml) was degassed and added to the reaction mixture. Then Pd$_2$(dba)$_3$ (0.110g) and Xantphos (0.150g) were added to the reaction mixture and the reaction mixture was degassed. The reaction mixture was stirred at 100° C. for 1 hour. The reaction mixture was cooled and the solvent was evaporated. The residue was taken up in ethyl acetate and water. The separated organic layer was dried (MgSO$_4$), filtered and the solvent was evaporated. The residue was purified by column chromatography (eluent: DCM/methanol 99/1). The desired product fractions were collected and the solvent was evaporated, yielding 0.450 g of residue. 0.100 g of residue was purified by high performance liquid chromatography (standard gradient elution with NH$_4$HCO$_3$ buffer). The desired product fractions were collected and the solvent was evaporated. The residue was suspended in DIPE, the precipitate was filtered off and dried (vacuo, 40° C.), yielding 0.029 g of intermediate (146).

B. Synthesis of the Final Compounds

EXAMPLE B.1

Preparation of

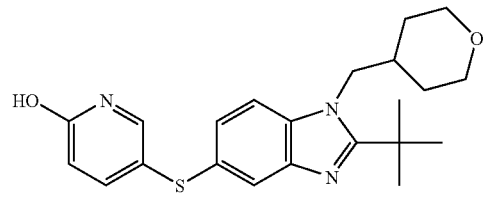

intermediate (23)

and

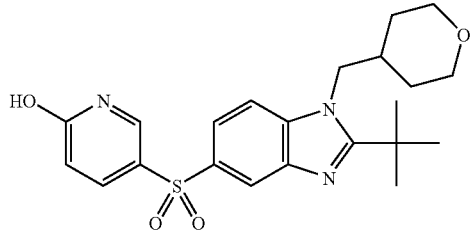

compound (1)

Cs$_2$CO$_3$ (1g) was added to a mixture of 5-bromo-2(1H)-pyridinone (0.870 g) and dioxane (6 ml). The resulting mixture was degassed by alternating vacuum and nitrogen atmosphere (3 cycles). Then a mixture of intermediate (9) (0.00157 mol) in dioxane (4 ml) was added, followed by Xantphos (0.056 g) and Pd$_2$(dba)$_3$ (0.044 g). The resulting reaction mixture was degassed again by alternating vacuum and nitrogen atmosphere (3 cycles). The reaction mixture was shaken overnight in a closed vessel at 100° C. The mixture was then concentrated under a stream of nitrogen at 65° C. The residue was partitioned between DCM and water and filtered over an Isolute HM-N™ filter to remove the aqueous phase. The organic layer was concentrated under a stream of nitrogen. The residue was purified by reversed phase high-performance liquid chromatography. The product fractions were collected and the solvent was evaporated, yielding intermediate (23). A part of intermediate (23) (0.296 g) was dissolved in chloroform (15 ml) and mCPBA (0.405 g; 2.2 equiv.) was added. This mixture was shaken at room temperature overnight. The organic layer was washed with NaOH (1 N) and the product was in the water layer. Acetic acid was added to the water layer and an extraction was performed with DCM. The organic layer was filtered over an Isolute HM-N™ filter and the solvent was evaporated. The residue was purified by reversed phase high-performance liquid chromatograpy. The desired fractions were collected and the solvent was evaporated, yielding compound (1) (mp. 251° C.).

EXAMPLE B.2

Preparation of intermediate (24)

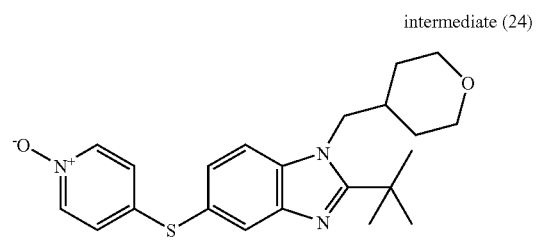

and compound (2)

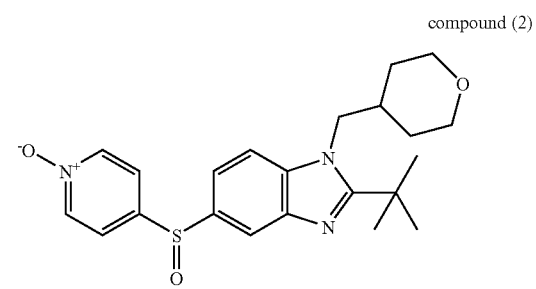

and compound (3)

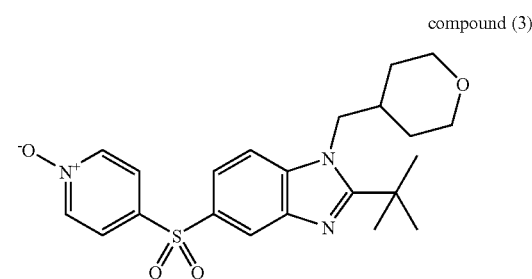

Cs$_2$CO$_3$ (1g) was added to a mixture of 4-chloropyridine-N-oxide (0.650 g) in dioxane (6 ml). Then a mixture of intermediate (9) (0.00156 mol) in dioxane (4 ml) was added. The resulting reaction mixture was shaken overnight at 80° C. The mixture was cooled and was then concentrated under a stream of nitrogen. The residue was partitioned between DCM and water and filtered over an Isolute HM-N™ filter to remove the aqueous phase. The residue was purified by reversed phase high-performance liquid chromatography. The product fractions were collected and the solvent was evaporated, yielding intermediate (24) (mp.: 186-187° C.). A part of intermediate (24) (0.370 g) was dissolved in chloroform (15 ml) and mCPBA (0.430 g; max. 2 equiv.) was added. This mixture was shaken at room temperature overnight. The organic layer was washed with NaOH (1 N), with water and the filtrate was filtered over an Isolute HM-N™ filter and concentrated under a stream of nitrogen. The residue was purified by reversed phase HPLC. Two different product fractions were collected and the solvent was evaporated, yielding 0.038 g compound (2) and 0.280 g of compound (3) (mp. 203° C.).

The heterocyclic reagent 4-chloropyridine-N-oxide can be replaced by other heterocycles such as e.g. 3,6-dichloropyridazine 1-(6-chloro-3-pyridinyl)ethanone, 6-chloro-3-pyridinecarboxamide for the preparation of other compounds of the invention.

EXAMPLE B.3

Preparation of compound (4)

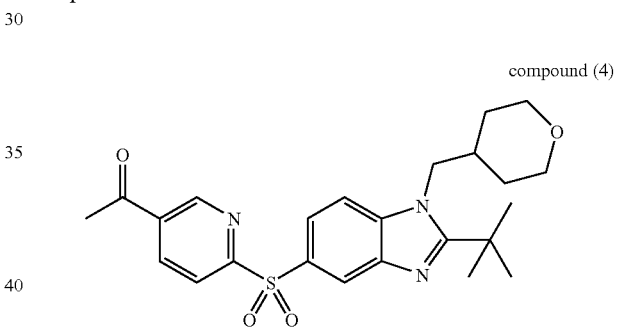

Cs$_2$CO$_3$ (0.0075 mol) was added to a mixture of 5-acetyl-2-bromopyridine (0.0065 mol) in dioxane (10 ml). The mixture was degassed with nitrogen. Intermediate (9) (0.005 mol) dissolved in dioxane (10 ml) was added to the reaction mixture which was degassed again with nitrogen. Xantphos (0.115 g) and then Pd$_2$(dba)$_3$ (0.090 g) were added to the reaction mixture and degassed again with nitrogen. The reaction mixture was stirred overnight at 100° C. Water (150 ml) was added. This mixture was extracted twice with DCM (100 ml). The combined organic layers were dried, filtered and the solvent was evaporated. The residue was dissolved in chloroform (4g) and then mCPBA (100 ml) was added. The reaction mixture was stirred overnight at room temperature. The reaction mixture was washed first twice with NaOH aqueous solution (1N, 100 ml), and then washed with water (100 ml). The separated organic layer was dried, filtered and the solvent was evaporated. The residue was purified by column chromatography over silica gel (eluent: CH$_2$Cl$_2$/(CH$_3$OH/NH$_3$) from 100/0 to 97/3). The product fractions were collected and the solvent was evaporated, yielding compound (4).

EXAMPLE B.4

Preparation of compound (6)

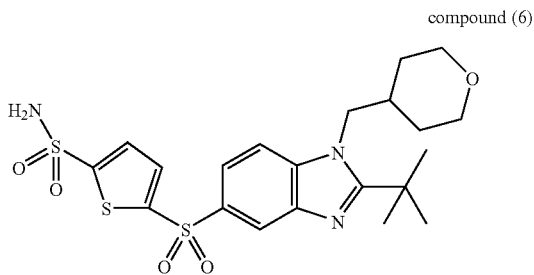 [SMILES: CC(C)(C)c1nc2cc(S(=O)(=O)c3ccc(S(N)(=O)=O)s3)ccc2n1CC1CCOCC1]

A mixture of intermediate (25) (0.002 mol) and mCPBA (0.005 mol) in chloroform (50 ml) was stirred at room temperature for 30 minutes. Then water was added. The separated organic layer was dried, filtered and the solvent was evaporated. The residue was purified by reversed phase chromatography. The desired fractions were collected and the solvent was evaporated, yielding 0.30 g of compound (6).

EXAMPLE B.5

Preparation of compound (19)

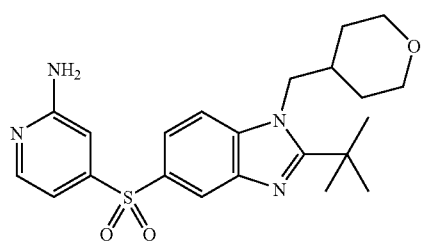

A mixture of compound (18) (0.00021 mol) and $NH_3$ in ethanol (5 ml) was stirred for two days at 120° C. The reaction mixture was extracted with DCM. The organic layer was removed, evaporated and the residue was purified by column chromatography over silica gel (eluent: $CH_2Cl_2/CH_3OH$ gradient from 100/0 to 96/4). The product fractions were collected and the solvent was evaporated, yielding 0.051 g of compound (19).

EXAMPLE B.6

Preparation of compound (26)

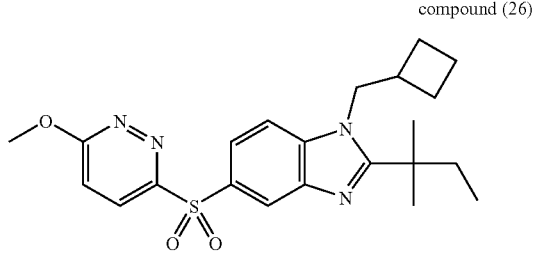 [SMILES: CCC(C)(C)c1nc2cc(S(=O)(=O)c3ccc(OC)nn3)ccc2n1CC1CCC1]

3-Chloro-6-methoxypyridazine (0.006 mol) was dissolved in 1,4-dioxane (10 ml). $Cs_2CO_3$ (2.1 g) was added and the mixture was degassed. A degassed solution of intermediate (19) (0.003 mol) in 1,4-dioxane (10 ml) was added. $Pd_2(dba)_3$ (0.080 g) was added and the mixture was degassed. Xantphos (0.095 g) was added and the mixture was degassed. The reaction mixture was stirred for 20 hours at 100° C., then cooled and the solvent was evaporated. The residue was partitioned between ethylacetate and water. The organic layer was separated, dried, filtered and the solvent was evaporated. The residue was stirred in chloroform (30 ml). This mixture was treated with mCPBA (2.1 g). The reaction mixture was stirred for one hour at room temperature, then it was washed with 1 N NaOH (2×). The organic layer was separated, dried, filtered and the solvent was evaporated. The residue was purified by column chromatography over silica gel (eluent: $CH_2Cl_2/CH_3OH$ 99/1). The product fractions were collected and the solvent was evaporated. The residue was purified by reversed-phase HPLC (gradient elution with $NH_4HCO_3$ buffer (0.25% in water)/$CH_3OH/CH_3CN$). The product fractions were collected and the solvent was evaporated. Methanol was added and evaporated again. The residue was dissolved in diethyl ether and converted into the hydrochloric acid salt (1:1) with HCl/diethyl ether. The resulting precipitate was filtered off and dried, yielding 0.034 g of compound (26).

EXAMPLE B.7

Preparation of

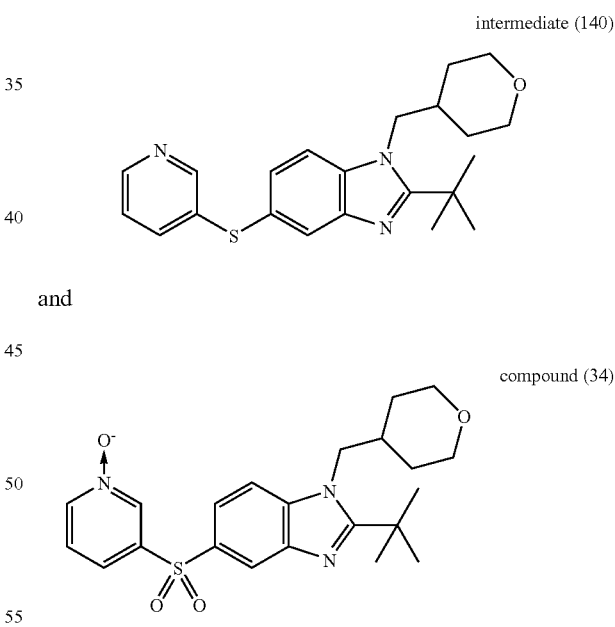

intermediate (140)

and compound (34)

$Cs_2CO_3$ (1g) was added to a mixture of 3-iodopyridine (1g) and dioxane (6 ml). The resulting mixture was degassed by alternating vacuum and $N_2$ atmosphere (3 cycles). Then a mixture of intermediate (9) (max. 0.00157 mol) in dioxane (4 ml) was added, followed by Xantphos (0.056 g) and $Pd_2$(dba)$_3$ (0.044 g). The resulting reaction mixture was degassed again by alternating vacuum and $N_2$ atmosphere (3 cycles). The reaction mixture was shaken overnight in a closed vessel at 100° C. The mixture was concentrated under a stream of $N_2$ at 65° C. The residue was partitioned between $CH_2Cl_2$ and $H_2O$ and filtered over an ISOLUTE HM-N filter to remove the aqueous phase. The organic layer was concentrated under a stream of N$_2$. The residue was purified by reversed phase high-performance liquid chromatography. The product fractions were collected and the solvent was evaporated, yielding 0.240 g of intermediate (140). A part of intermediate (140) (0.215 g) was dissolved in chloroform (15 ml) and mCPBA (2.5 equiv.) was added. This mixture was shaken at room temperature overnight. The organic layer was washed 2× with NaOH (1 N, 5 ml), with H$_2$O (5 ml) and the organic layer was filtered over an ISOLUTE HM-N filter. The filtrate was concentrated under a stream of N$_2$. The residue was purified by reversed-phase HPLC. The desired product fraction was collected and the solvent was evaporated, yielding 0.028 g of compound (34).

EXAMPLE B.8 a) Preparation of compound (46)

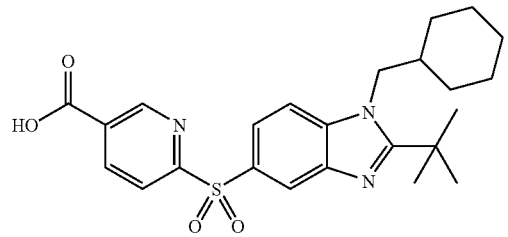

A mixture of compound (35) (0.0021 mol) and a solution of lithium hydroxide in water (1N) (10 ml) in THF (40 ml) was stirred at room temperature overnight. The reaction mixture was neutralized to pH=7 with 1N HCl aqueous solution. The solvent was evaporated. The residue was purified by reversed-phase HPLC (gradient elution with NH$_4$HCO$_3$ buffer (0.25% in water)/CH$_3$OH/CH$_3$CN). The product fractions were collected and worked-up, yielding 0.7 g of compound (46).

b) Preparation of compound (37)

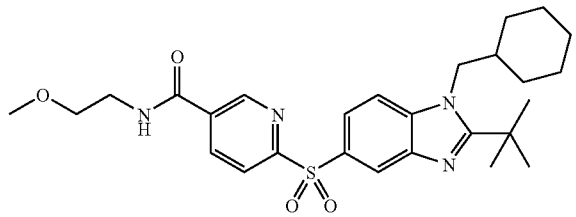

Compound (46) (0.00044 mol) was added to a mixture of triethylamine (0.00066 mol) in chloroform (10 ml). 2-Methoxy-ethanamine (0.0006 mol) was added and was shaken overnight at room temperature. DCM (100 ml) was added. This mixture was washed 2 times with water (100 ml). The separated organic layer was dried (MgSO$_4$), filtered and the solvent was evaporated. The residue was purified by reversed-phase HPLC (gradient elution with NH$_4$HCO$_3$ buffer (0.25% in water)/CH$_3$OH/CH$_3$CN). The product fractions were collected and worked-up. The residue was triturated under acetonitril. The precipitate was filtered off, yielding 0.105 g compound (37) (mp. 206° C. to 207° C.).

The following compound was prepared in a similar way using pyrrolidine instead of 2-methoxy-ethanamine as reagent compound (38)

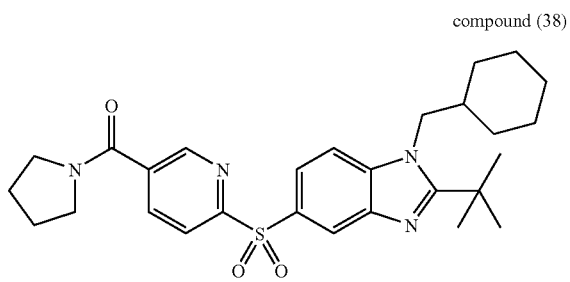 [SMILES: CC(C)(C)c1nc2cc(S(=O)(=O)c3ccc(C(=O)N4CCCC4)cn3)ccc2n1CC1CCCCC1]

EXAMPLE B.9

Preparation of compound (41)

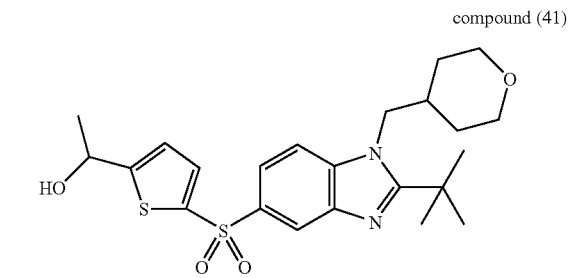 [SMILES: CC(O)c1ccc(S(=O)(=O)c2ccc3c(c2)nc(C(C)(C)C)n3CC2CCOCC2)s1]

NaBH$_4$ (0.003 mol) was added to a mixture of compound (40) (0.001 mol) in a mixture of methanol/ethanol(50/50) (20 ml), stirred at room temperature under N$_2$ atmosphere. The reaction mixture was stirred overnight at room temperature. The reaction mixture was concentrated. DCM (100 ml) was added. Water (50 ml) was added. The organic layer was separated, dried (MgSO$_4$), filtered and the solvent was evaporated. The residue was crystallized from DIPE/2-propanol. The precipitate was filtered off, washed and dried, yielding 0.290 g of compound (41).

EXAMPLE B.10 a) Preparation of compound (42)

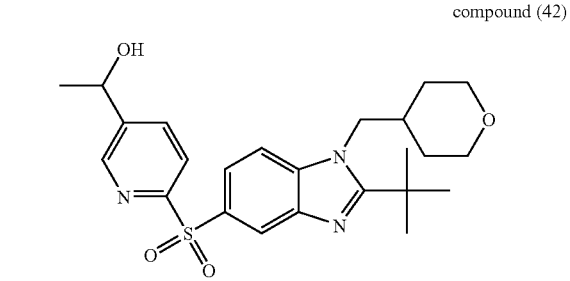 [SMILES: CC(O)c1ccc(S(=O)(=O)c2ccc3c(c2)nc(C(C)(C)C)n3CC2CCOCC2)nc1]

NaBH$_4$ (0.015 mol) was added to a mixture of compound (4) (0.0011 mol) in ethanol (30 ml) and stirred at room temperature. DCM (30 ml) was added and stirred for 2 hours at room temperature. The reaction mixture was quenched with HCl 1N aqueous solution (10 ml). Water (100 ml), NH$_4$OH aqueous solution (20 ml) and DCM (100 ml) were added to the reaction mixture. The mixture was separated into aqueous layer and organic layer. The aqueous layer was re-extracted with DCM (100 ml). The organic layers were combined and washed with brine. The separated organic layer was dried (MgSO₄), filtered and the solvent was evaporated. The residue was purified by column chromatography over silica gel (eluent: DCM/(CH₃OH/NH₃) from 100/0 to 94/6). The product fractions were collected and the solvent was evaporated, yielding 0.36 g of product. This product (0.36 g) was triturated under DIPE/CH₃CN. The precipitate was filtered off, yielding compound (42) (mp. 177° C. to 179° C.).

compound (49)

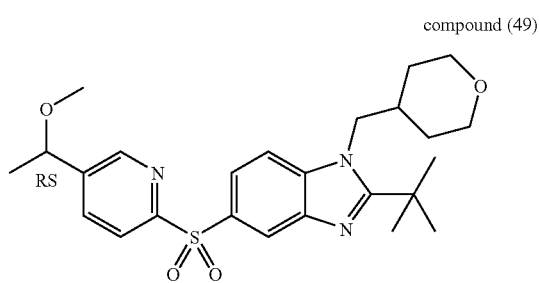

b) Preparation of

Sodium hydride (60%) (0.00125 mol) was added to a mixture of compound (42) (0.000656 mol) in THF (15 ml) and was stirred for 20 minutes at room temperature. Iodomethane (0.0014 mol) was added and stirred at room temperature overnight. Sodium hydride (60%) (0.00125 mol) was added again and stirred for 20 minutes at room temperature. Then iodomethane (0.0014 mol) was added again and stirred over the weekend at 40° C. Water (100 ml) and DCM (100 ml) were added. After extraction, the separated organic layer was dried (MgSO₄), filtered and the solvent was evaporated. The residue was purified by reversed-phase HPLC (gradient elution with NH₄HCO₃ buffer (0.25% in water)/CH₃OH/CH₃CN). The product fractions were collected and the solvent was evaporated. The residue was re-crystallized from DIPE/few drops of CH₃CN and the precipitate was filtered off, yielding 0.110 g of compound (49) (mp. 140° C.).

EXAMPLE B.11

Preparation of intermediate (141)

and compound (43)

Cs₂CO₃ (0.015 mol) was added to a mixture of 5-bromo-3-pyridinecarbonitrile (0.013 mol) in dioxane (20 ml). The mixture was degassed with N₂. Intermediate (9) (0.01 mol) in dioxane (20 ml) was added to the reaction mixture and degassed again with N₂. Xantphos (0.230 g) and then Pd₂(dba)₃ (0.180 g) were added to the reaction mixture and degassed again with N₂. The reaction mixture was stirred overnight at 100° C. Water (150 ml) was added. This mixture was extracted 2 times with DCM (100 ml). The combined organic layers were dried (MgSO₄), filtered and the solvent was evaporated. The residue was purified by combiflash column chromatography over silica gel (eluent: DCM/(CH₃OH/NH₃) from 100/0 to 98/2). The product fractions were collected and the solvent was evaporated, yielding 2g of intermediate (141). Intermediate (141) (2g) was dissolved in chloroform (3g) and then 3-chlorobenzene-carboperoxoic acid (50 ml) was added. The reaction mixture was stirred for 2 hours at room temperature. The reaction mixture was washed first 2 times with NaOH 1N aqueous solution (200 ml), and then washed with brine (200 ml). The separated organic layer was dried (MgSO₄), filtered and the solvent was evaporated. The residue was purified by combiflash column chromatography over silica gel (eluent: DCM/(CH₃OH/NH₃) from 100/0 to 98/2). The product fractions were collected and the solvent was evaporated. The residue was re-crystallized from 2-propanol/CH₃CN and the precipitate was filtered off, yielding 0.9 g of compound (43) (mp. 240° C.).

EXAMPLE B.12

Preparation of compound (44)

Compound (43) (0.0006 mol) in sulfuric acid (4 ml) was stirred at 30° C.-40° C. for 5 hours. The reaction mixture was poured out on ice (100 ml). This mixture was extracted 4 times with DCM/CH₃OH (100 ml). The combined organic layers were dried (MgSO₄), filtered and the solvent was evaporated. The residue was re-crystallized from DCM and the precipitate was filtered off, yielding 0.170 g of compound (44) (mp. 259° C.).

EXAMPLE B.13

Preparation of

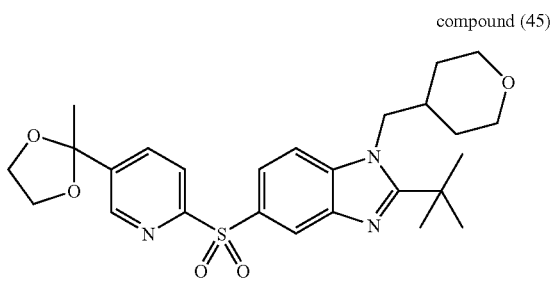 [SMILES: CC(C)(C)c1nc2cc(S(=O)(=O)c3ccc(C4(C)OCCO4)cn3)ccc2n1CC1CCOCC1]

compound (45)

A mixture of compound (4) (0.0032 mol), 1,2-ethanediol (1 ml) and 4-methylbenzene-sulfonic acid (0.6 g) in toluene (70 ml) was stirred at reflux with a water separator. The reaction mixture washed with NaHCO$_3$ saturated aqueous solution. The separated organic layer was dried (MgSO$_4$), filtered and the solvent was evaporated. The residue was purified by reversed-phase HPLC (gradient elution with NH$_4$HCO$_3$ buffer (0.25% in water)/CH$_3$OH/CH$_3$CN). The product fractions were collected and the solvent was evaporated. The residue was re-crystallized from DIPE/CH$_3$CN and the precipitate was filtered off, yielding 0.606 g of compound (45) (mp. 191° C.).

EXAMPLE B.14

Preparation of compound (47)

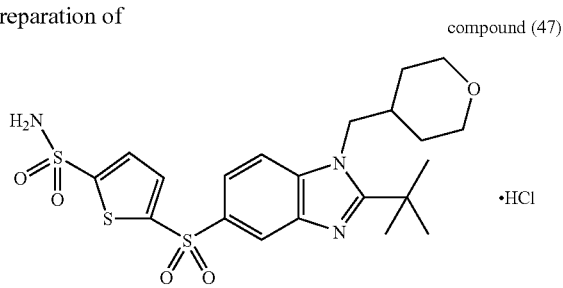

·HCl

A mixture of compound (6) (0.15 g, 0.0003 mol) and 2-propanol (10 ml) was heated.

A mixture of 2-propanol and HCl (6N) (1 ml) was added. Then the mixture was cooled. The precipitate was filtered off, washed and dried, yielding 0.060 g of compound (47.

EXAMPLE B.15a

Preparation of compound (170)

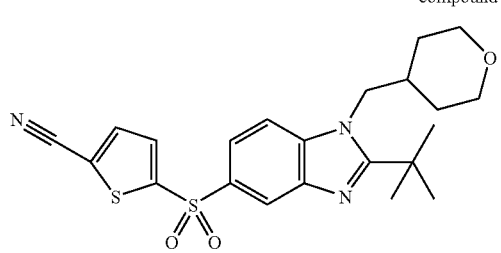

A mixture of intermediate (33) (0.013 mol) and 3-chlorobenzenecarboperoxoic acid (0.030 mol) in chloroform (150 ml) was stirred at room temperature for 30 minutes. Then water was added. The separated organic layer was dried (MgSO$_4$), filtered and the solvent was evaporated. The residue was purified by column chromatography over silica gel (eluent: DCM/CH$_3$OH from 100/0 to 98.5/1.5). The product fractions were collected and the solvent was evaporated. The residue was solidified in DIPE, then filtered off, washed and dried, y ielding 3.3 g of compound (170).

EXAMPLE B.15b

Preparation of compound (171)

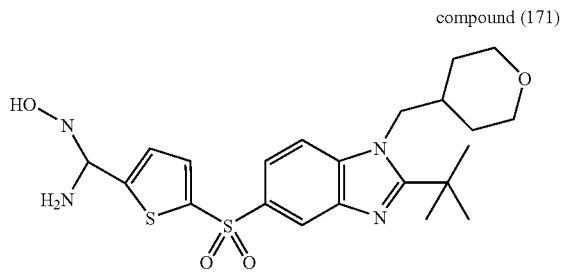 [SMILES: CC(C)(C)c1nc2cc(S(=O)(=O)c3ccc(C(N)NO)s3)ccc2n1CC1CCOCC1]

A mixture of compound (170) (0.0045 mol), hydroxylamine (0.009 mol) and NaHCO$_3$ (0.009 mol) in 2-propanol (40 ml) was stirred for 5 hours at 60° C., then cooled and the solvent was evaporated. The residue was taken up into DCM. The organic solution was washed with water, dried (MgSO$_4$), filtered and the solvent was evaporated, yielding 1.36 g of compound (171).

EXAMPLE B.15c

Preparation of compound (48)

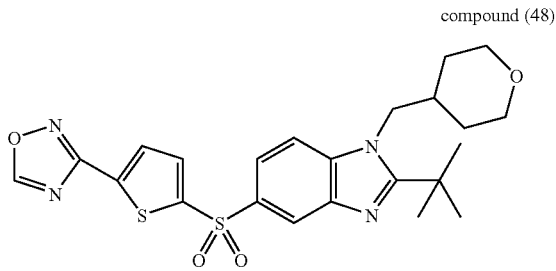 [SMILES: CC(C)(C)c1nc2cc(S(=O)(=O)c3ccc(-c4ncon4)s3)ccc2n1CC1CCOCC1]

A mixture of compound (171) (0.0011 mol) and trifluoro [1,1'-oxybis[ethane]]boron (0.200 ml) in trimethoxymethane (2 ml) was stirred for 2 hours at 80° C. The reaction mixture was cooled and the solvent was evaporated. The residue was taken up into DCM and the organic solution was washed with water, then dried (MgSO$_4$), filtered and the solvent was evaporated. The residue was crystallized from DIPE with a small amount of 2-propanol. The precipitate was filtered off, washed and dried, yielding 0.325 g of compound (48).

EXAMPLE B.16

Preparation of

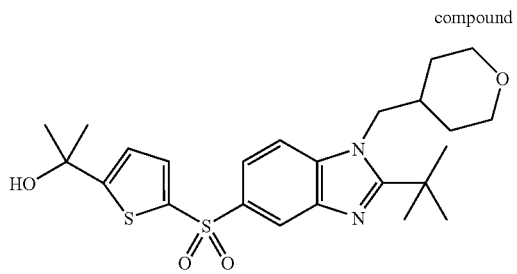
compound (53)

A mixture of compound (40) (0.0011 mol) in diethyl ether (10 ml) and THF (5 ml) was stirred at room temperature under $N_2$ atmosphere. A solution of bromomethyl-magnesium in diethyl ether (3M) (0.0030 mol) was added dropwise. The reaction mixture was stirred overnight. Water was added carefully. More diethyl ether was added. The organic layer was separated, dried ($MgSO_4$), filtered and the solvent was evaporated. The residue was purified by reversed-phase HPLC (gradient elution with $NH_4HCO_3$ buffer (0.25% in water)/$CH_3OH/CH_3CN$). The product fractions were collected and the solvent was evaporated. Methanol was added and co-evaporated, yielding 0.445 g of compound (53).

EXAMPLE B.17

Preparation of

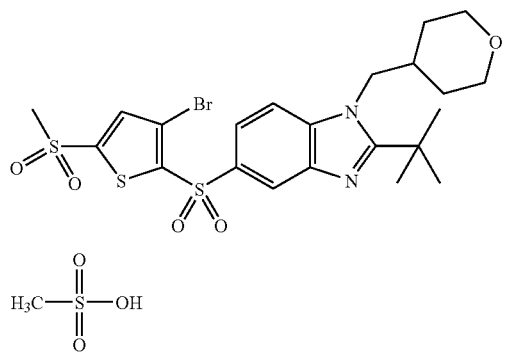
compound (64)

Compound (62) (0.00021 mol) in 2-propanol (5 ml) was stirred at room temperature. Then methanesulfonyl chloride (0.00031 mol) was added. The reaction mixture was warmed up and then cooled. The precipitate was filtered off, washed and dried, yielding 0.077 g of compound (64).

EXAMPLE B.18

Preparation of

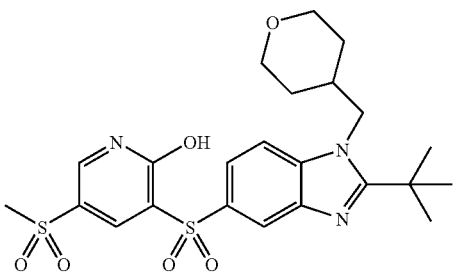
compound (77)

and

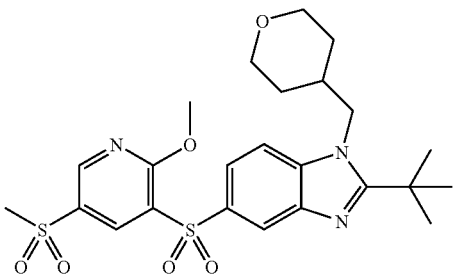
compound (78)

A mixture of compound (69) (0.00025 mol) and a solution of sodium methylate in methanol(30%) (0.5 ml) in methanol (10 ml) was stirred overnight at room temperature. The solvent was evaporated. The residue was purified by reversed-phase HPLC. Two product fraction groups were collected and worked-up, yielding 0.015 g of compound (77) and 0.022 g of compound (78).

EXAMPLE B.19

Preparation of

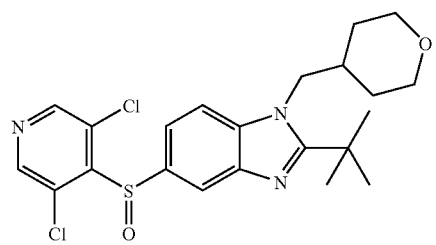
compound (85)

and compound (84)

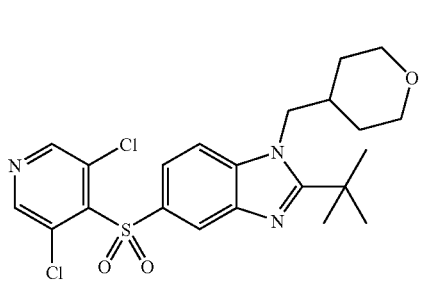

A mixture of intermediate (44) (0.00133 mol) and 3-chlorobenzene-carboperoxoic acid (0.0027 mol) in chloroform (15 ml) was shaken overnight at room temperature. The mixture was washed with 1 N NaOH (2×15 ml), once with water (15 ml). The organic phase was filtered through an Isolute HM-N filter, and the filtrate's solvent was evaporated under a stream of $N_2$. The residue was purified by reversed-phase HPLC. Two product fractions were collected and their solvent was evaporated. Each fraction was crystallized from DIPE/2-propanol, filtered off and dried, yielding 0.155 g of compound (85) and 0.161 g of compound (84).

EXAMPLE B.20

Preparation of compound (86)

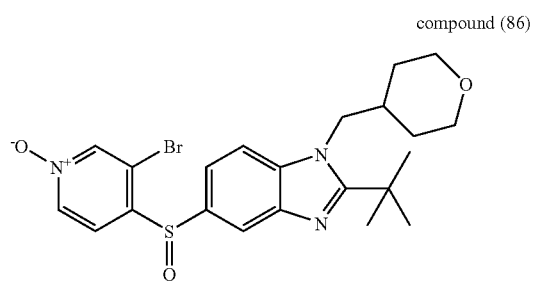

and compound (87)

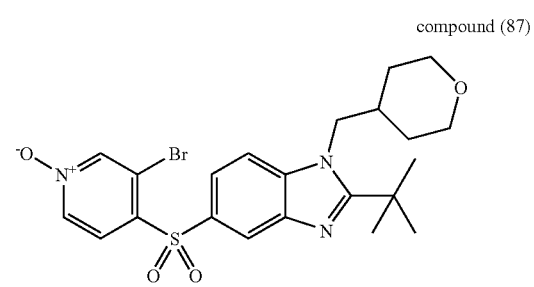

and compound (88)

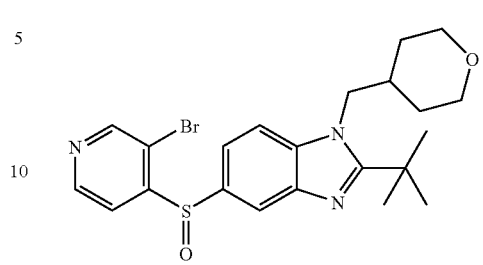

3-Chlorobenzenecarboperoxoic acid (0.007 mol) was added portionwise to intermediate (45) (0.00348 mol) in chloroform (20 ml). The reaction mixture was shaken overnight at room temperature. The organic mixture was washed with 1 N NaOH (2×20 ml), once with water (20 ml), then filtered through an Isolute HM-N filter, and the filtrate's solvent was evaporated under a stream of $N_2$. The residue was purified by reversed-phase HPLC. Different product fractions were collected and their solvent was evaporated. Each residue was crystallized from DIPE/2-propanol. Each precipitate was filtered off and dried, yielding 0.242 g of compound (86); 0.213 g of compound (87) and 0.1 g of compound (88).

EXAMPLE B.21

Preparation of compound (89)

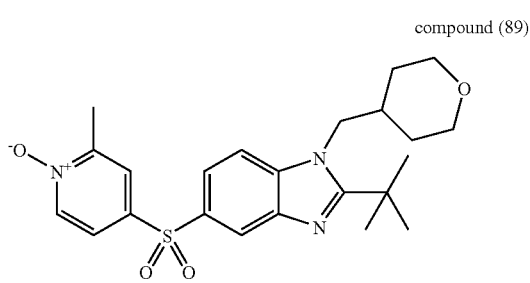

A mixture of intermediate (46) (0.0043 mol) and 3-chlorobenzene-carboperoxoic acid (0.005 mol) in chloroform (80 ml) was shaken for one hour at room temperature. More 3-chlorobenzenecarboperoxoic acid (0.005 mol) was added and the reaction mixture was shaken overnight at room temperature. The mixture was washed with 1 N NaOH (2×75 ml), once with water (75 ml). The organic phase was dried ($MgSO_4$), filtered and the solvent was evaporated. The residue was purified by column chromatography over silica gel (eluent: DCM/($CH_3OH/NH_3$) 97/3). The product fractions was collected and the solvent was evaporated. The residue (1.35 g) was purified further by reversed-phase HPLC. The desired fraction groups were collected and the solvent was evaporated. The residue of the desired product was crystallized from 2-propanol/DIPE, yielding 0.646 g of compound (89).

EXAMPLE B.22

Preparation of

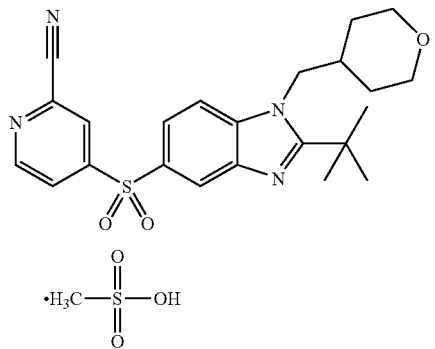

compound (93)

A mixture of intermediate (30) (0.77 g, 0.0019 mol), mCPBA (70%) (1.17 g, 0.0047 mol) and chloroform (40 ml) was stirred at room temperature for 1 hour. Chloroform (100 ml) was added and the mixture was washed with a NaOH solution (1 N; 2×100 ml). The organic layer was dried (MgSO₄), filtered and the solvent was evaporated. The residue was purified by column chromatography over silica gel (eluent: DCM/CH₃OH(NH₃) from 100/0 till 97/3. The desired fractions were collected and the solvent was evaporated. The residue was dissolved in 2-propanol (approx. 50 ml) and methylsulfonic acid (0.12 g was added). The methylsulfonate salt crystallized from this solution. The product was filtered off, washed with 2-propanol/DIPE and dried (in vacuo), yielding 0.63 g of compound (93).

EXAMPLE B.23 a) Preparation of

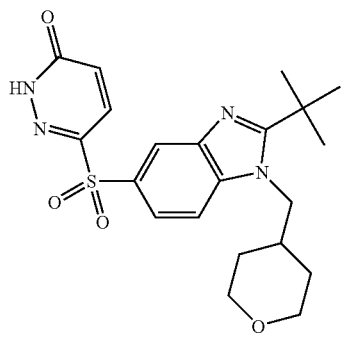

compound (94)

A mixture of compound (11) (0.0036 mol, 1.6 g) in hydrochloric acid was stirred and refluxed for 1 hour. The reaction mixture was cooled and DCM was added. The organic layer was separated, dried, filtered and the solvent evaporated, yielding 1.108 g of compound (94).

b) Preparation of

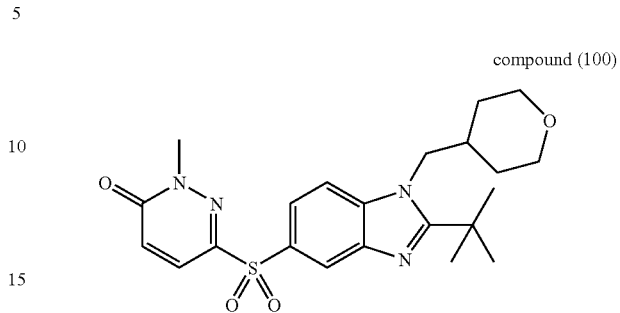

compound (100)

A mixture of compound (94) (0.0005 mol, 0.200 g, 1 equiv.) and 1,1-dimethoxy-N,N-dimethylmethanamine (0.100 ml, 1.5 equiv.) in DMF (1 ml) was stirred and refluxed until reaction was complete. Ice was added. Residue 1 precipitated from the mixture. The rest of the mixture was extracted with DCM. Water was added. The organic layer was separated, dried, filtered, and the solvent was evaporated, yielding residue 2. Residue 1 and 2 were combined and the mixture was triturated under 2-propanol. The precipitate was filtered off and dried in vacuo, yielding 0.125 g of compound (100).

EXAMPLE B.24

Preparation of

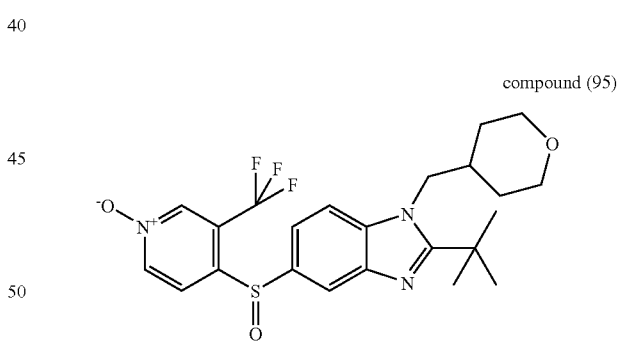

compound (95)

A mixture of intermediate (54) (0.00122 mol) and 3-chlorobenzenecarboperoxoic acid (0.0027 mol) in chloroform (15 ml) was shaken for 3 hours at room temperature. More 3-chlorobenzenecarboperoxoic acid (0.32 g) was added and the reaction mixture was shaken overnight at room temperature. The mixture was washed with 1 N NaOH (2×15 ml), once with water (15 ml). Then the organic phase was filtered through an Isolute HM-N filter, and the filtrate's solvent was evaporated under a stream of N₂. The residue was purified by reversed-phase HPLC. The product fraction was collected and worked-up, yielding 0.100 g of compound (95).

EXAMPLE B.25

Preparation of

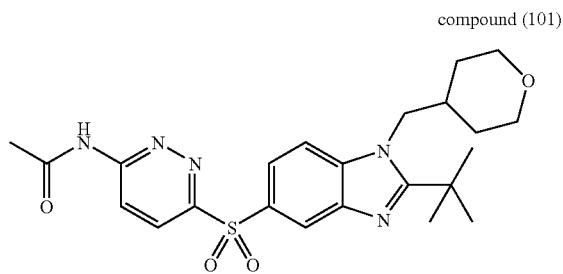 [SMILES: CC(=O)Nc1ccc(S(=O)(=O)c2ccc3c(c2)nc(C(C)(C)C)n3CC2CCOCC2)nn1]

compound (101)

A mixture of intermediate (56) (0.00121 mol) and 3-chlorobenzenecarboperoxoic acid (0.00242 mol) in chloroform (18 ml) was shaken for 2 hours at room temperature. The mixture was washed with 1 N NaOH (2×15 ml), once with water (15 ml), then filtered through an Isolute HM-N filter, and the filtrate's solvent was evaporated under a stream of $N_2$. The residue was purified by Combiflash flash column chromatography over silica gel (eluent: DCM/(CH$_3$OH/NH$_3$) from 100/0 to 96/4). The desired product fraction was collected and the solvent was evaporated, yielding 0.110 g of compound (101).

EXAMPLE B.26

Preparation of

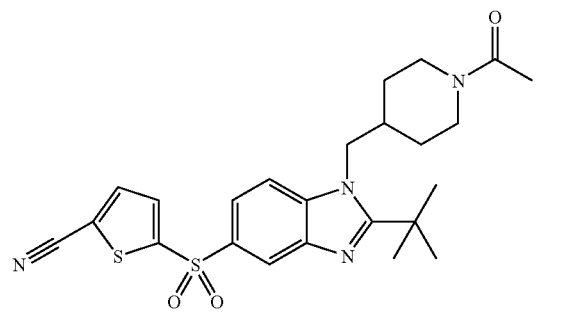

compound (159)

3-Chlorobenzenecarboperoxoic acid (1 g) was added in 2 portions to a solution of intermediate (63) (0.001 mol) in chloroform (40 ml) at room temperature. The reaction mixture was stirred at room temperature for 30 minutes. The reaction mixture was washed with water/NaOH. The organic layer was dried (MgSO$_4$), filtered and evaporated. The residue was purified over a filter with silica gel using DCM/CH$_3$OH (7N NH$_3$) from 100/0 to 96/4 as eluent. The product fractions were collected and evaporated. The product was crystallized from DIPE and 2-propanol. The solid was filtered off, washed and dried, yielding 0.24 g of compound (159).

EXAMPLE B.27

Preparation of

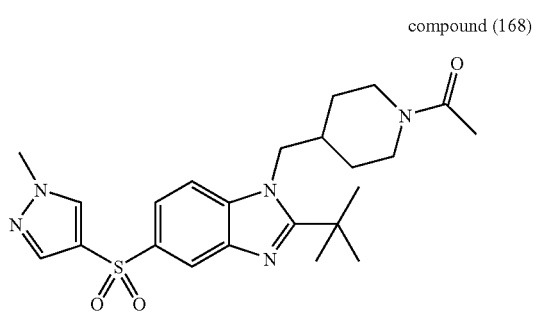 [SMILES: CC(=O)N1CCC(Cn2c(C(C)(C)C)nc3cc(S(=O)(=O)c4cnn(C)c4)ccc32)CC1]

compound (168)

3-Chlorobenzenecarboperoxoic acid (0.2 g) was added in 2 portions to a solution of intermediate (64) (0.003 mol) in chloroform (20 ml) at room temperature. The reaction mixture was stirred at room temperature for 30 minutes. The reaction mixture was washed with water/NaOH. The organic layer was dried (MgSO$_4$), filtered and evaporated. The residue was purified over a column with silica gel using DCM/CH$_3$OH (7N NH$_3$) from 100/0 to 98/2 as eluent. The product fractions were collected and evaporated. The residue was crystallized from 2-propanol and some DIPE. The solid was filtered off, washed and dried, yielding 0.058 g of compound (168).

EXAMPLE B.28

Preparation of

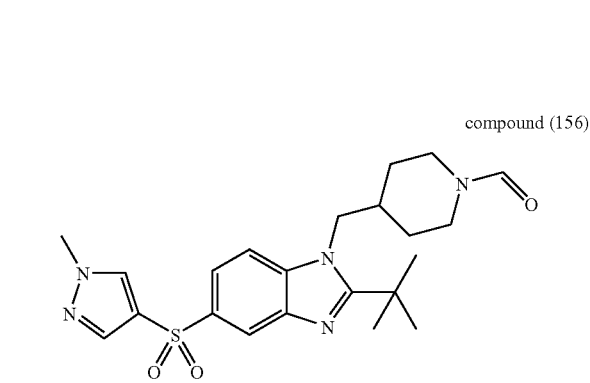 [SMILES: Cn1cc(S(=O)(=O)c2ccc3c(c2)nc(C(C)(C)C)n3CC2CCN(C=O)CC2)cn1]

compound (156)

A mixture of intermediate (67) (0.0007 mol), 3-chlorobenzenecarboperoxoic acid (36 g) and chloroform (20 ml) was shaken at room temperature for 20 minutes. The reaction mixture was washed with 2×15 ml 1N aq. NaOH, 1×15 ml water, and filtered over an isolute HM-N filter. The solvent was removed under a stream of $N_2$ at 50° C., and the residue crystallized from DIPE, yielding 0.2 g of compound (156).

EXAMPLE B.29

Preparation of compound (163)

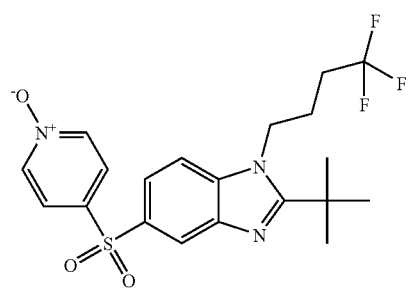

Intermediate (71) (0.0023 mol) was dissolved in chloroform (40 ml) at room temperature. 3-Chlorobenzenecarboperoxoic acid (0.567 g) was added slowly (exothermic reaction) and the mixture was stirred for 30 minutes. The reaction mixture was extracted twice with saturated NaHCO$_3$ and once with 1N NaOH. The organic layers were washed with water and dried (MgSO$_4$). The residue was purified by HPLC (HPLC method A). The desired fractions were collected and the solvent was evaporated, yielding compound (163).

EXAMPLE B.30 a) Preparation of compound (116)

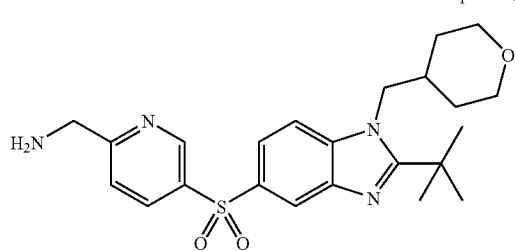

A mixture of compound (51) (0.0003 mol), Raney nickel (0.02 g) and NH$_3$ in methanol (50 ml) was catalytic hydrogenated under hydrogen atmosphere at 14° C. After uptake H$_2$ (2 equivalents) the reaction mixture was filtered over dicalite, and concentrated. (During evaporation the reaction mixture turns dark green,). The residue was purified by reversed phase HPLC (gradient elution with NH$_4$HCO$_3$ buffer (0.25% in water)/CH$_3$OH/CH$_3$CN), yielding 115 mg of compound (116).

b) Preparation of compound (117)

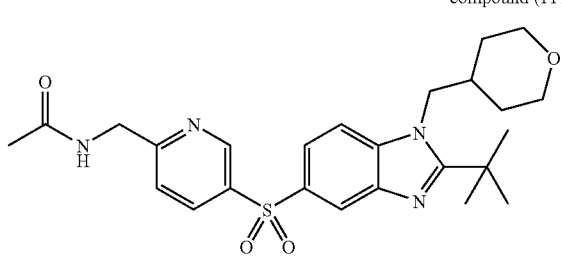

A mixture of compound (116) (0.0002 mol), acetic acid 1,1'-anhydride (0.0003 mol) and DCM (10 ml) was shaken at room temperature for 2 hours. The organic layer was washed with 2×15 ml sat. aq. NaHCO$_3$ solution and 1× with 15 ml water. The mixture was filtered over an isolute HM-N filter. The filtrate was dried under stream of nitrogen at 60° C. The residue was crystallized from DIPE/2-propanol, yielding 71 mg of compound (117).

EXAMPLE B.31

Preparation of compound (137)

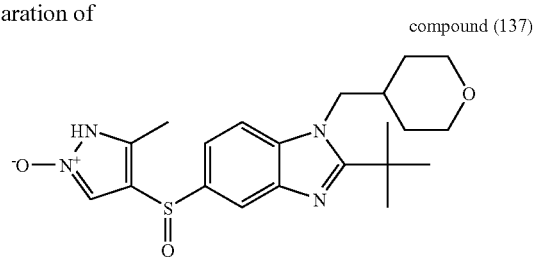

and compound (118)

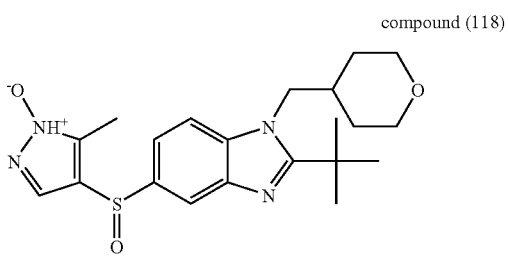

A solution of intermediate (80) (0.07 g, 0.000182 mol) in chloroform (ethanol free) (3 ml) was cooled to 0° C. mCPBA (70%) (0.135 g, 0.000546 mol) was added. The mixture was stirred for 30 minutes at 0° C. and then for 2 hours at room temperature. An extra amount of mCPBA (70%) (3 equiv.) was added and the mixture was stirred again for 90 minutes. Then the mixture was diluted with chloroform and an extraction procedure was done with NaOH (1 N); water and NaCl. After the extraction, two products (A and B) were obtained. Product A: The separated organic layer was evaporated, yielding 0.040 g of crude residue A. The crude was purified by column chromatography over silica gel. The desired fractions were collected and the solvent was evaporated, yielding 0.028 g of compound (137).
Product B: The aqueous layer (NaOH) obtained after the extraction was also evaporated. The residue was triturated with chloroform in an ultra-sonic bath for 15 minutes, filtered and concentrated, yielding 0.040 g of compound (118).

EXAMPLE B.32

Preparation of compound (122)

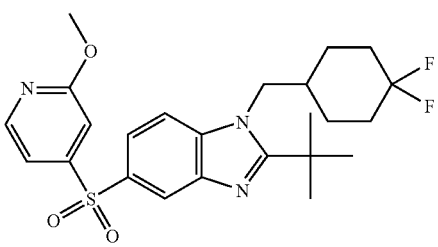

A mixture of intermediate (91) (0.00024 mol, crude) in acetic acid (3 ml) was heated for 20 minutes at 150° C. in a microwave oven. Hydrochloric acid (2 drops) was added and the reaction mixture was heated for 2 hours at 150° C. (microwave oven). Upon cooling, the solvent was evaporated. The residue was partitioned between DCM and an aqueous NaHCO₃ solution. The organic layer was separated, dried, filtered and the solvent evaporated. The residue was separated and purified by reversed-phase HPLC (gradient elution with (NH₄OAc 0.5% in water/CH₃CN 90/10)/CH₃OH/CH₃CN). The desired product fraction was collected and worked-up, yielding 0.006 g of compound (122).

EXAMPLE B.33 a) Preparation of compound (123)

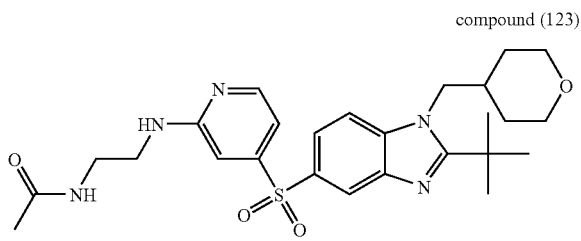 [SMILES: CC(=O)NCCNc1cc(S(=O)(=O)c2ccc3c(c2)nc(C(C)(C)C)n3CC2CCOCC2)ccn1]

A reaction mixture of compound (25) (0.0007 mol) and N-(2-aminoethyl)acetamide (0.0022 mol) in dioxane (15 ml) was stirred at 110° C. for 20 hours. The reaction mixture was cooled and the solvent was evaporated. The residue was taken up in DCM and water. The separated organic layer was dried (MgSO₄), filtered and the solvent was evaporated. The residue was purified by column chromatography (eluent: DCM/CH₃OH from 100/0 to 98/2). The product fractions were collected and the solvent was evaporated. The residue was suspended in DIPE/ drop CH₃CN. The precipitate was filtered off and dried (vacuo, 50° C.), yielding 0.100 g of compound (123).

Compound (126) can be prepared in a similar way as compound (123) starting from compound (25) and using 3-methoxy-1-propanamine instead of N-(2-aminoethyl)-acetamide compound (126)

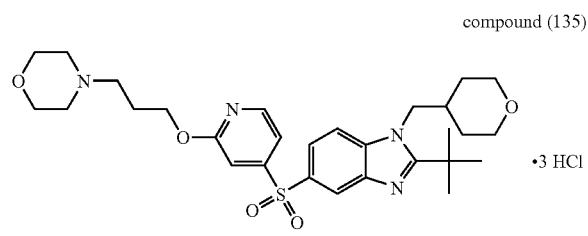 [SMILES: CC(C)(C)c1nc2cc(S(=O)(=O)c3ccnc(OCCCN4CCOCC4)c3)ccc2n1CC1CCOCC1 ; "·3 HCl"]

b) Preparation of compound (135)

·3 HCl

Reaction under N₂. Sodium hydride (60%) (0.001 mol) was added to compound (25) (0.0007 mol) in THF (5 ml) and stirred for 15 minutes at 40° C. Then 4-morpholine-propanol (0.001 mol) in THF (5 ml) was added. The reaction mixture was stirred at 50° C. for 20 hours. The reaction mixture was cooled and the solvent was evaporated. The residue was taken up in DCM/water. The organic layer was separated, dried (MgSO₄), filtered and the filtrate's solvent was evaporated. The residue was purified by reversed-phase HPLC (gradient elution with NH₄HCO₃ buffer (0.25% in water)/CH₃OH/CH₃CN). The product fractions were collected and the solvent was evaporated. This residue was stirred at 0° C. in ethyl acetate and HCl in 2-propanol. The precipitate was filtered off and dried (vacuo, 60° C.), yielding 0.044 g of compound (135).

c) Preparation of compound (152)

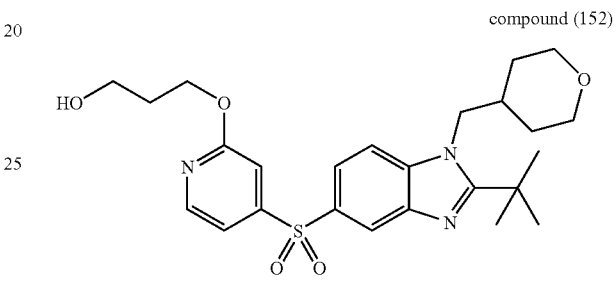

A mixture of compound (25) (0.0016 mol), 1,3-propanediol (0.005 mol), 2-methyl-2-propanol, potassium salt in THF (1M) (2 ml) and dioxane (10 ml) was stirred at 80° C. for 2 hours. The reaction mixture was cooled. Water (100 ml) was added and the mixture was extracted with 5×80 ml DCM. The organic layer was dried (MgSO₄), and concentrated, yielding 0.7 g of residue. The residue was purified by reversed-phase HPLC (HPLC method B) and worked-up (crystallized from DIPE), yielding 0.170 g of compound (152).

d) Preparation of compound (130)

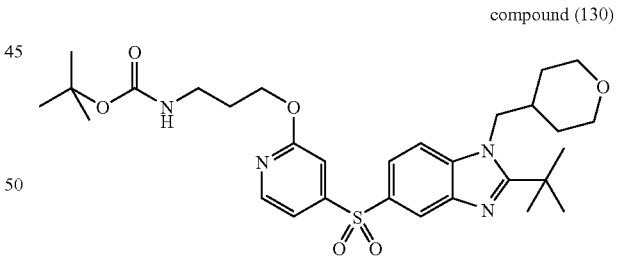

A mixture of (3-hydroxypropyl)carbamic acid, 1,1-dimethylethyl ester (0.0033.mol) and sodium hydride in mineral oil (60%) (0.0033 mol) in dioxane (10 ml) was stirred at 60° C. for 30 minutes. Compound (25) (0.00162 mol) was added and the reaction mixture was stirred overnight at 100° C. The reaction mixture was cooled. Water (100 ml) was added. This mixture was extracted with DCM (2×100 ml). The separated organic layer was dried (MgSO₄), filtered and the solvent was evaporated. The residue was purified by reversed-phase HPLC (gradient elution with NH₄HCO₃ buffer (0.25% in water)/CH₃OH/CH₃CN). The product fractions were collected and the solvent was evaporated, yielding 0.225 g of compound (130).

Other final compounds can be prepared in a similar way as compound (130) by replacing (3-hydroxypropyl)carbamic acid, 1,1-dimethylethyl ester with 3-(dimethylamino)-1-propanol, 3-methoxy-1-propanol, or 2-methoxyethanol.

e) Preparation of compound (131)

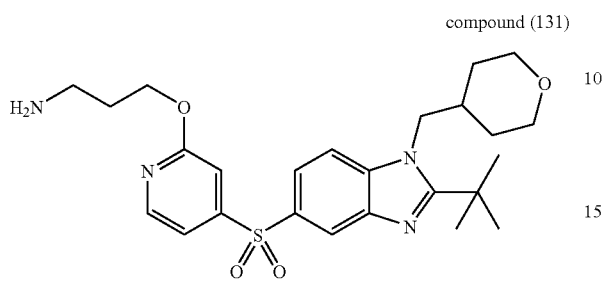

A mixture of compound (130) (0.00036 mol) and TFA (5 ml) in DCM (5 ml) was stirred at room temperature for 20 minutes. The solvents were removed under a stream of $N_2$. The residue was dissolved in DCM (12 ml), and washed with 1 N aq. NaOH (10 ml) and water (10 ml). The organic phase was filtered over an Isolute HM-N filter and the solvent was evaporated under a stream of $N_2$, yielding 0.176g of compound (131).

f) Preparation of compound (132)

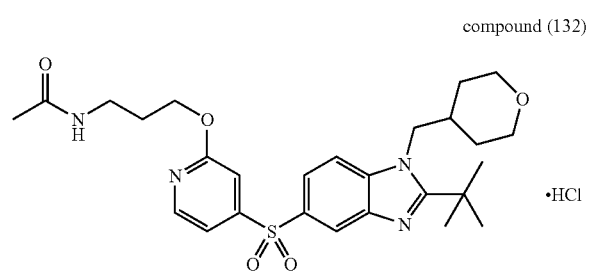 [SMILES: CC(=O)NCCCOc1cc(S(=O)(=O)c2ccc3c(c2)nc(C(C)(C)C)n3CC2CCOCC2)ccn1 ; Cl]

·HCl

A mixture of compound (131) (0.003 mol), acetic acid 1,1'-anhydride (0.067 g) and DCM (10 ml) was shaken at room temperature for 3 hours. The reaction mixture was washed with 2×10 ml 1N aq. NaOH, 1×10 ml water, and filtered over an isolute HM-N filter. The filtrate was concentrated under a stream of $N_2$ and crystallized as HCl salt in diethyl ether, yielding 14g of compound (132).

EXAMPLE B.34

Preparation of compound (124)

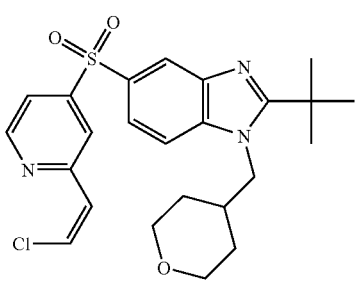

and compound (125)

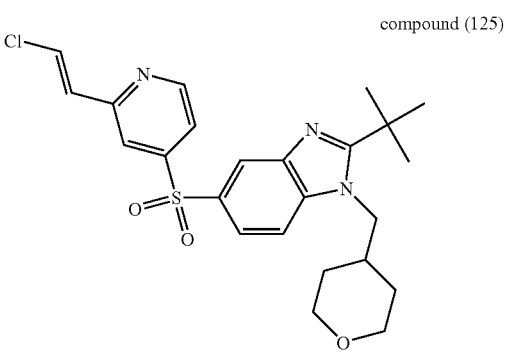 [SMILES: CC(C)(C)c1nc2cc(S(=O)(=O)c3ccnc(/C=C/Cl)c3)ccc2n1CC1CCOCC1]

Intermediate (95) (0.233 g, 0.000528 mol) was dissolved in chloroform. 3-Choro-benzenecarboperoxoic acid (0.260 g, 2 equiv.) was added. The mixture was partitioned between DCM and an aqueous $NaHCO_3$ solution. The organic layer was separated, dried, filtered and the solvent evaporated. The residue (crude, 0.0005 mol) was dissolved in acetic acid (15 ml). Fe powder (0.215 g) was added. The reaction mixture was stirred for 2 hours at room temperature. The solvent was evaporated. The residue was partitioned between DCM and an aqueous $NaHCO_3$ solution. The organic layer was separated, dried, filtered and the solvent evaporated. The residue was separated and purified by HPLC. Two product fraction groups were collected and worked-up, yielding 0.080 g of compound (124) and 0.030 g of compound (125).

EXAMPLE B.35 a) Preparation of compound (146)

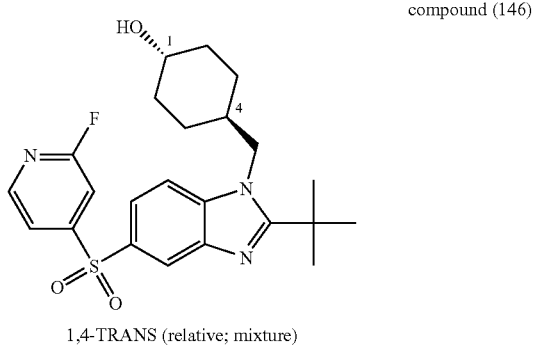 [SMILES: CC(C)(C)c1nc2cc(S(=O)(=O)c3ccnc(F)c3)ccc2n1C[C@H]1CC[C@H](O)CC1]

1,4-TRANS (relative; mixture)

3-Chorobenzenecarboperoxoic acid (0.001 mol) was added in 2 portions to a solution of intermediate (109) (0.003 mol) in chloroform (20 ml) at room temperature. The reaction mixture was stirred at room temperature for 30 minutes. The reaction mixture was washed with water/NaOH. The organic layer was dried ($MgSO_4$), filtered and evaporated. The residue was purified over a filter with silica gel using DCM/ $CH_3OH$ (7N $NH_3$) from 100/0 to 99/1 as eluent. The product fractions were collected and evaporated. The product was solidified from DIPE. The solid was filtered off, washed and dried, yielding 0.12 g of compound (146) (1,4-TRANS; relative; mixture).

b) Preparation of

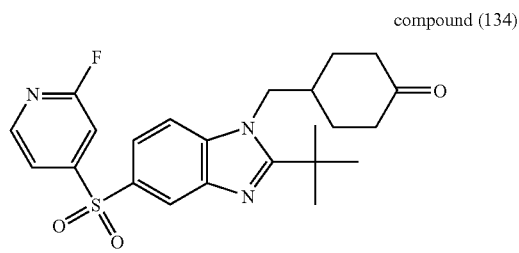 [SMILES: CC(C)(C)c1nc2cc(S(=O)(=O)c3ccnc(F)c3)ccc2n1CC1CCC(=O)CC1]

compound (134)

To a mixture of 4 Å molecular sieves (0.2 g) in DCM (dry) (3 ml) and Pyridine, trioxochlorochromate (VI) under $N_2$ atm., was added compound (146) (0.0002 mol) in DCM(1 ml). The reaction mixture was stirred at room temperature for 2 hours. The reaction mixture was poured over a filter with dicalite. The filtrate was concentrated. The residue was used crude, yielding compound (134).

c) Preparation of

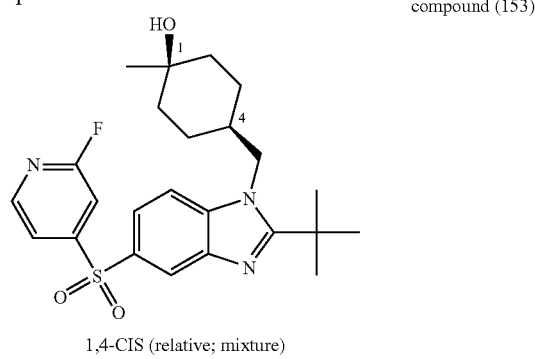 [SMILES: CC(C)(C)c1nc2cc(S(=O)(=O)c3ccnc(F)c3)ccc2n1C[C@H]1CC[C@@](C)(O)CC1]

compound (153)

1,4-CIS (relative; mixture)

Bromomethylmagnesium in diethyl ether (3.0 M) (0.2 ml) was added to diethyl ether (3 ml). The reaction mixture was cooled to −60° C. Compound (134) (0.0002 mol) in THF (1 ml) was added and the reaction mixture was allowed to reach room temperature. The solvent was evaporated, and the residue was taken into DCM/water. The organic layer was separated, filtered over an Isolute filter and the filtrate's solvent was evaporated. The residue was purified by reversed-phase HPLC purification (gradient elution with $NH_4HCO_3$ buffer (0.25% in water)/$CH_3OH/CH_3CN$). The product fractions were collected and the solvent was evaporated. $CH_3OH$ was added and then evaporated. The residue was dried under vacuum at 50° C., yielding 8 mg of compound (153) (1,4-CIS; relative; mixture).

EXAMPLE B.36

Preparation of

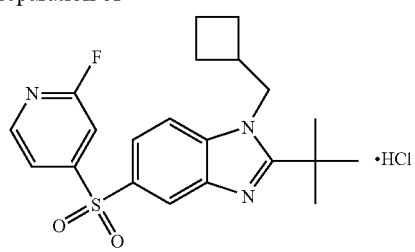

compound (136)

3-Chorobenzenecarboperoxoic acid (0.003 mol) was added in 2 portions to a solution of intermediate (112) (0.009 mol) in chloroform (15 ml) at room temperature. The reaction mixture was stirred at room temperature for 30 minutes. The reaction mixture was washed with water/NaOH. The organic layer was dried (MgSO4), filtered and evaporated. The residue was purified by column chromatography using DCM/$CH_3OH:NH_3$ (100% to 98%/2%) as eluent. The product fractions were collected and evaporated. The residue was further purified by reversed-phase HPLC (gradient elution with $NH_4HCO_3$ buffer (0.25% in water)/$CH_3OH/CH_3CN$). The product fractions were collected, evaporated and co-evaporated with $CH_3CN$. The residue was solidified in diethyl ether by adding 1 ml of a HCl/ether solution (1M). The solid was filtered off, washed and dried, yielding 0.15g of compound (136).

EXAMPLE B.37

Preparation of

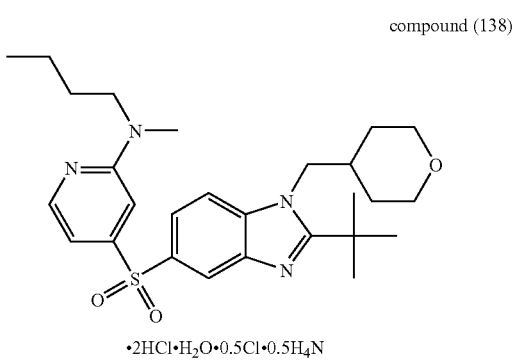 [SMILES: CCCCN(C)c1cc(S(=O)(=O)c2ccc3c(c2)nc(C(C)(C)C)n3CC2CCOCC2)ccn1]

compound (138)

•2HCl•$H_2O$•0.5Cl•0.5$H_4N$

3-Chorobenzenecarboperoxoic acid (0.0009 mol) was added in 2 portions to a solution of intermediate (114) (0.0003 mol) in chloroform (10 ml) at room temperature. The reaction mixture was stirred at room temperature for 30 minutes. The reaction mixture was washed with water/NaOH. The organic layer was dried($MgSO_4$), filtered and evaporated. The residue was taken up in acetic acid (100%) (5 ml) and Fe powder (0.1 g). This mixture was stirred at 60° C. for 1 hour. The residue was purified by column chromatography using DCM/$CH_3OH:NH_3$ (100% to 98%/2%) as eluent. The product fractions were collected and evaporated. The residue was further purified by reversed-phase HPLC (gradient elution with $NH_4HCO_3$ buffer (0.25% in water)/$CH_3OH/CH_3CN$). The product fractions were collected, concentrated and then extracted with DCM. The organic layer was dried ($MgSO_4$), filtered and evaporated. The residue was crystallized from DIPE, 2-propanol and HCl/ether 1M solution (0.5 ml). The solid was filtered off, washed and dried, yielding 0.04 g of compound (1 38).

EXAMPLE B.38 a) Preparation of

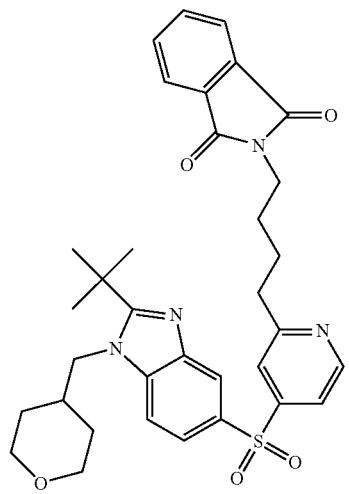

compound (169)

A mixture of intermediate (117) (0.0005 mol) in chloroform (20 ml) was cooled to 0° C. 3-Chorobenzenecarboperoxoic acid (0.210 g) was added and the reaction mixture and stirred for 2 hours. The separated organic layer was washed with NaOH aqueous solution (1M), dried (MgSO$_4$), filtered and the solvent was evaporated. The residue was added to acetic acid (6 ml). Then Fe powder (0.280 g) was added. The mixture was stirred at 60° C. for 90 minutes. The mixture was cooled and the solvent was evaporated. The residue was partitioned between DCM and water. This mixture was alkalized with NaHCO$_3$. The separated organic layer was dried (MgSO$_4$), filtered and the solvent was evaporated, yielding 0.220 g of compound (169).

b) Preparation of

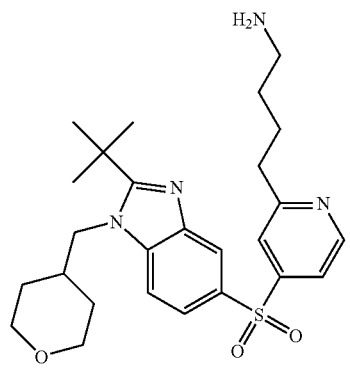

compound (139)

A mixture of compound (169) (0.0003 mol) and hydrazine monohydrate (0.1 ml) in ethanol (4 ml) was stirred and refluxed for 1 hour. The reaction mixture was cooled and the solvent was evaporated. The residue was taken up in DCM and water. The separated organic layer was dried (MgSO$_4$), filtered and the solvent was evaporated. The residue was purified by column chromatography (eluent: DCM/CH$_3$OH 90/10). The desired product fractions were collected and the solvent was evaporated, yielding 0.105 g of compound (139).

c) Preparation of

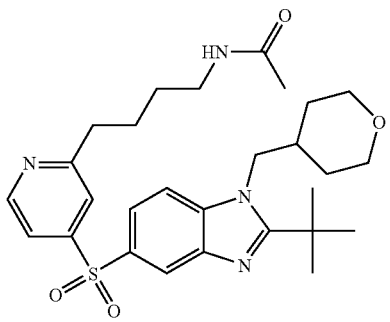

compound (141)

·2H$_2$O·2HCl

Triethylamine (0.06 ml) was added to a mixture of compound (139) (0.0002 mol) in DCM (5 ml) at 0° C. Acetyl chloride (0.0002 mol) was added to the reaction mixture and then stirred for 10 minutes at room temperature. The reaction mixture was washed with water and then filtered over Isolute. The filtrate's solvent was evaporated under a N$_2$ flow. The residue was taken up in ethyl acetate and in a solution of HCl in diethyl ether. The precipitate was filtered and dried, yielding 0.032 g of compound (141).

EXAMPLE B.39 a) Preparation of

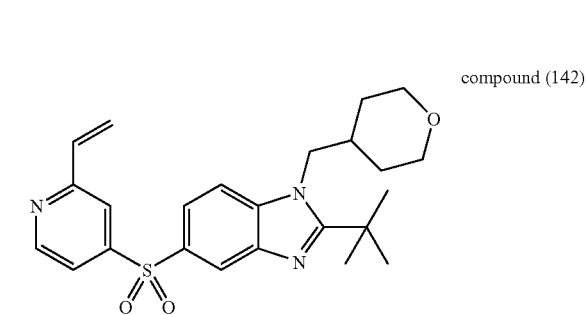 [SMILES: C=Cc1cc(S(=O)(=O)c2ccc3c(c2)nc(C(C)(C)C)n3CC2CCOCC2)ccn1]

compound (142)

Compound (18) (0.0045 mol), tributylethenylstannane (0.0067 mol), tetrakis(triphenyl-phosphine)palladium (0.33 g) and DMF (50 ml) were degassed in a closed vessel. The reaction mixture was shaken at 80° C. for 24 hours. 1,4-Dioxane (100 ml) and potassium fluoride (2g) were added. The reaction mixture was filtered over dicalite. The filtrate was concentrated. The residue was taken up in DCM and washed with water. The organic layer was dried (MgSO$_4$), filtered and evaporated. The residue was purified by reversed phase HPLC (gradient elution with NH$_4$HCO$_3$ buffer (0.25% in water)/CH$_3$OH/CH$_3$CN). The product fractions were collected, evaporated and co-evaporated with methanol until complete dryness, yielding 0.75 g of compound (142).

b) Preparation of

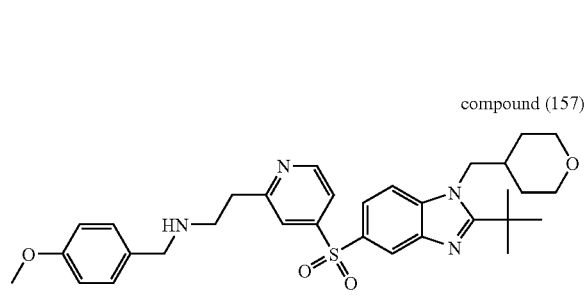 [SMILES: COc1ccc(CNCCc2cc(S(=O)(=O)c3ccc4c(c3)nc(C(C)(C)C)n4CC3CCOCC3)ccn2)cc1]
compound (157)

A mixture of compound (142) (0.0005 mol), 4-methoxybenzenemethanamine (0.014 mol) and N-ethyl-N-(1-methylethyl)-2-propanamine (0.003 mol) in N,N-dimethyl-acetamide (5 ml) was stirred for 3 days at 110° C. After cooling the reaction mixture was taken up in water (20 ml) and ethyl acetate (50 ml). The organic layer was dried (MgSO₄), filtered and evaporated. The residue was shaken overnight with scavenger PS-benzaldehyde (8g) (capacity: 1.2 mmol/g) in DCM (200 ml). The scavenger was removed by filtration. The filtrate was concentrated and purified on silica gel using DCM/CH₃OH (7N NH3) (from 100:0 to 96:4) as eluent. The product fractions were collected and evaporated to dryness. The residue was used as such in the next reaction, yielding 0.21 g of compound (157).

c) Preparation of

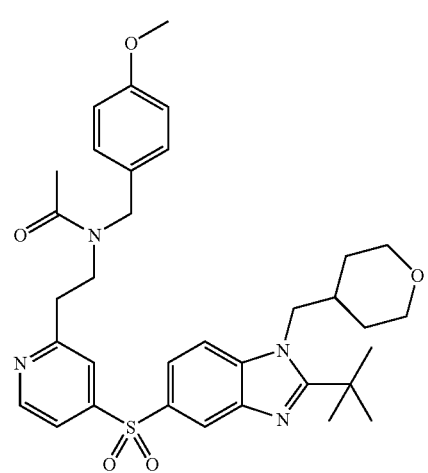
compound (172)

A mixture of compound (157) (0.0003 mol) and N-ethyl-N-(1-methylethyl)-2-propanamine (0.001 mol) in THF (10 ml) at room temperature, was added acetic acid 1,1'-anhydride (0.0005 mol). The reaction mixture was shaken in a closed vessel at 35° C. for 1 hour. The reaction mixture was taken up in 100 ml DCM and then washed with 10 ml water. The organic layer was dried (MgSO₄), filtered and evaporated. The residue was used as such in the next reaction, yielding 0.2 g of compound (172).

d) Preparation of

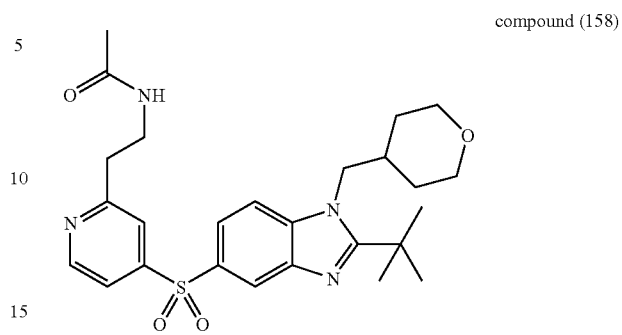
compound (158)

TFA (10 ml) was added compound (172) (0.0003 mol) in DCM (1 ml) at room temperature. The vessel was closed. The reaction mixture was shaken for 1 week at 60° C. The reaction mixture was cooled and the solvent evaporated. The residue was taken up in DCM and washed with water. The organic layer was dried (MgSO₄), filtered and evaporated. The residue was purified on silica gel using DCM/CH₃OH (7N NH₃) (from 100% to 96/4) as eluent. The product fractions were collected and evaporated to dryness. The residue was crystallized from DIPE and some 2-propanol. The solid was filtered off, washed and dried, yielding 0.095 g of compound (158).

EXAMPLE B.40

Preparation of

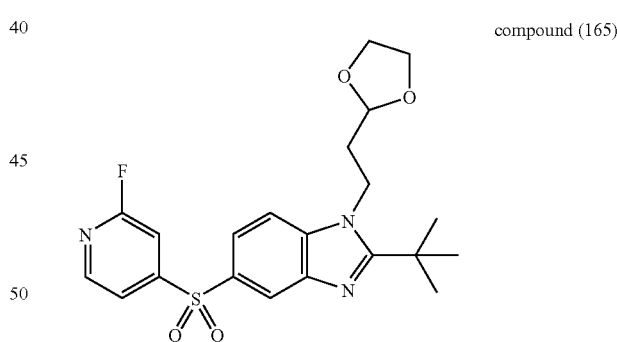
compound (165)

A solution of intermediate (138) (0.3 g, 0.000747 mol) in chloroform (ethanol free) (10 ml) was cooled to 0° C. mCPBA (70%) (0.4 g, 3 equiv.) was added and the mixture was stirred for 30 minutes at 0° C., and then for 3 hours at room temperature. The reaction was quenched with NaOH (1 N) and the crude product was extracted with chloroform. The separated organic layer was washed with water and brine, dried (Na₂SO₄) and the solvent was evaporated to yield 0.286 g of a white foam. The white foam was purified by reversed phase column chromatography. The desired product fraction was collected, worked-up and the solvent was evaporated, yielding 0.097 g of compound (165).

EXAMPLE B.41

Preparation of

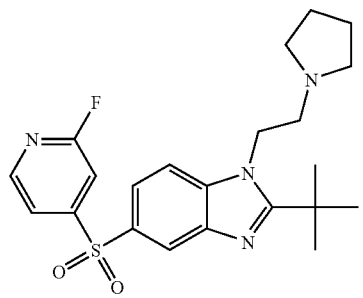

compound (144)

A mixture of 2-tert-butyl-5-(2-fluoro-pyridine-4-sulfonyl)-1-[2-(1-oxy-pyrrolidin-1-yl)-ethyl]-1H-benzoimidazole (0.0003 mol) in THF (150 ml) was hydrogenated with palladium on activated carbon (10%) as a catalyst. After an uptake of hydrogen (3 equiv.) the catalyst was filtered off and the solvent was evaporated. The residue was partitioned between DCM (10 ml) and water (1 ml). This mixture was filtered over Isolute. The filtrate's solvent was evaporated (under $N_2$ flow), yielding 0.135 g of residue. 0.100 g of residue was purified by reversed-phase HPLC (gradient elution with $NH_4HCO_3$ buffer (0.25% in water)/$CH_3OH$/$CH_3CN$). The desired product fractions were collected and the solvent was evaporated. The residue was solidified in DIPE, the precipitate was filtered off and dried (vacuo, 40° C.), yielding 0.025 g of compound (144).

Tables F-1 and F-2 lists the compounds that were prepared by analogy to one of the above Examples.

TABLE F-1

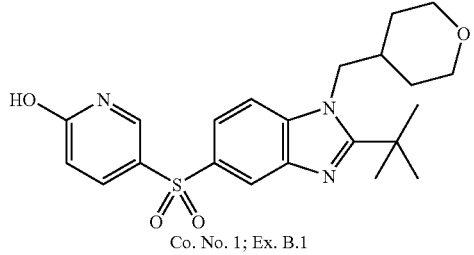

Co. No. 1; Ex. B.1

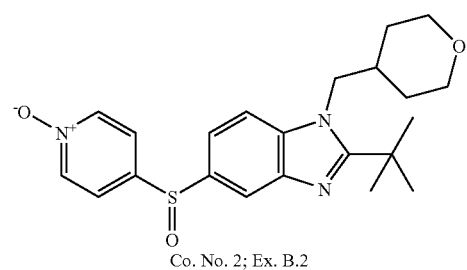

Co. No. 2; Ex. B.2

TABLE F-1-continued

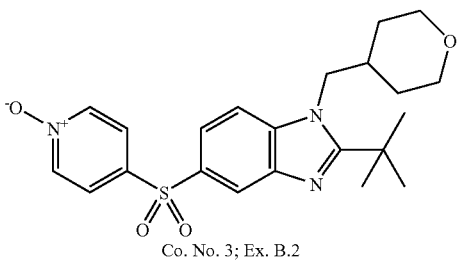

Co. No. 3; Ex. B.2

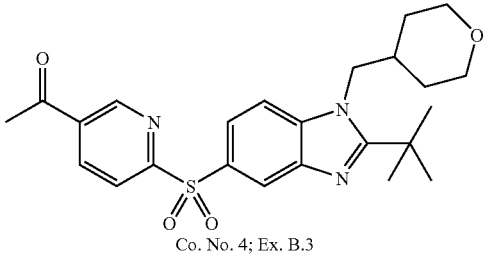

Co. No. 4; Ex. B.3

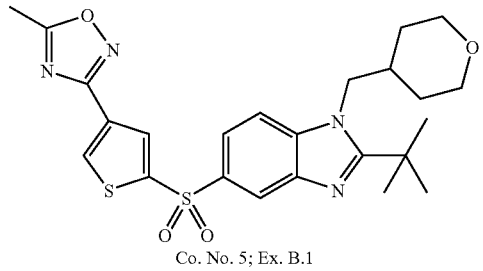

Co. No. 5; Ex. B.1

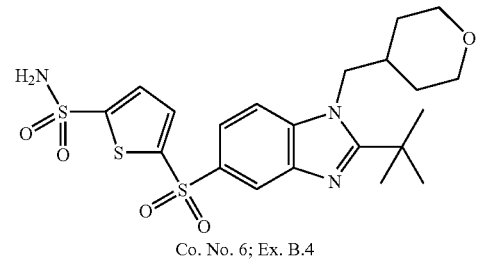

Co. No. 6; Ex. B.4

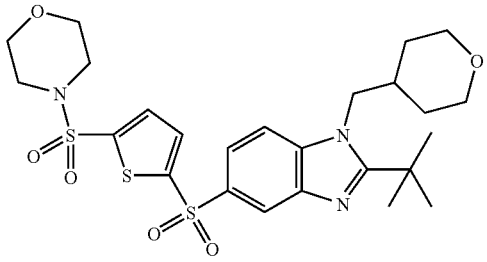 [SMILES: CC(C)(C)c1nc2cc(S(=O)(=O)c3ccc(S(=O)(=O)N4CCOCC4)s3)ccc2n1CC1CCOCC1]

Co. No. 7; Ex. B.4

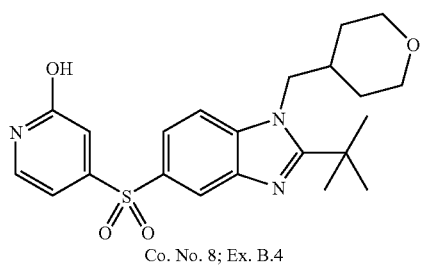

Co. No. 8; Ex. B.4

TABLE F-1-continued
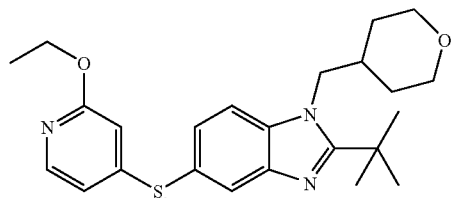
Co. No. 9; Ex. B.4
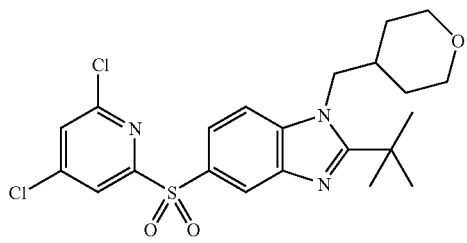 [SMILES: CC(C)(C)c1nc2cc(S(=O)(=O)c3cc(Cl)cc(Cl)n3)ccc2n1CC1CCOCC1]
Co. No. 10; Ex. B.4
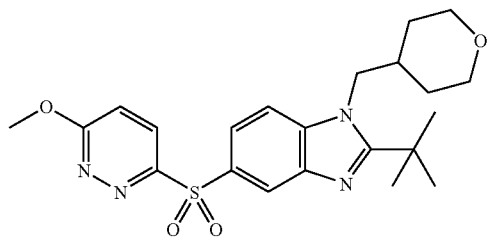 [SMILES: COc1ccc(S(=O)(=O)c2ccc3c(c2)nc(C(C)(C)C)n3CC2CCOCC2)nn1]
Co. No. 11; Ex. B.4
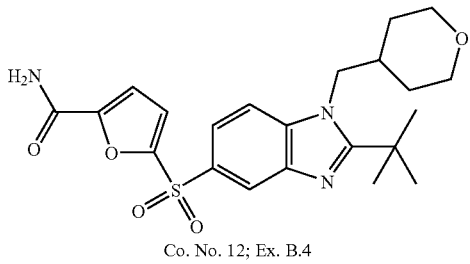
Co. No. 12; Ex. B.4
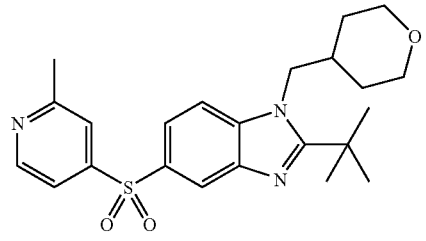 [SMILES: Cc1cc(S(=O)(=O)c2ccc3c(c2)nc(C(C)(C)C)n3CC2CCOCC2)ccn1]
Co. No. 13; Ex. B.4
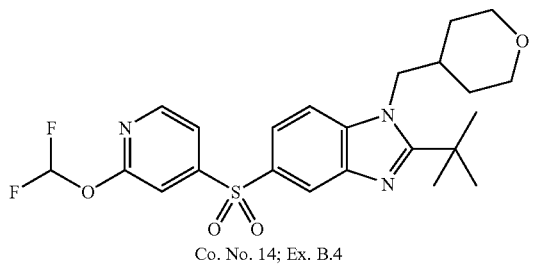
Co. No. 14; Ex. B.4
TABLE F-1-continued
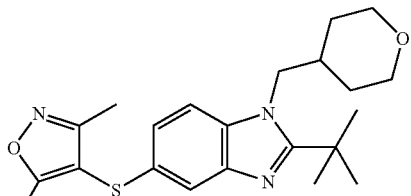
Co. No. 15; Ex. B.4
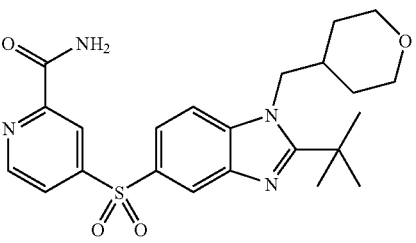 [SMILES: CC(C)(C)c1nc2cc(S(=O)(=O)c3ccnc(C(N)=O)c3)ccc2n1CC1CCOCC1]
Co. No. 16, Ex. B.4
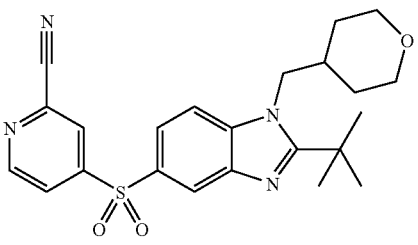 [SMILES: CC(C)(C)c1nc2cc(S(=O)(=O)c3ccnc(C#N)c3)ccc2n1CC1CCOCC1]
Co. No. 17, Ex. B.4
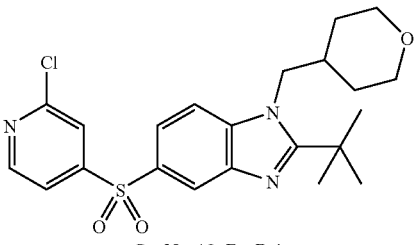
Co. No. 18; Ex. B.4
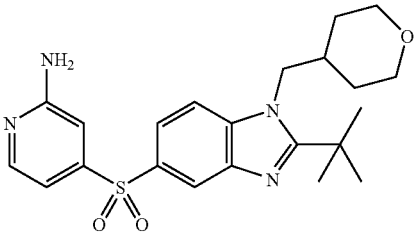 [SMILES: CC(C)(C)c1nc2cc(S(=O)(=O)c3ccnc(N)c3)ccc2n1CC1CCOCC1]
Co. No. 19; Ex. B.5
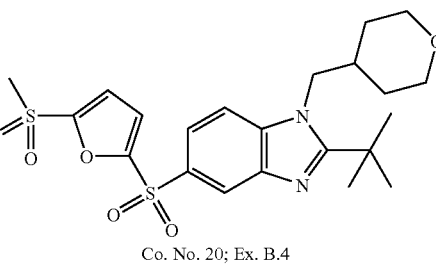
Co. No. 20; Ex. B.4

TABLE F-1-continued
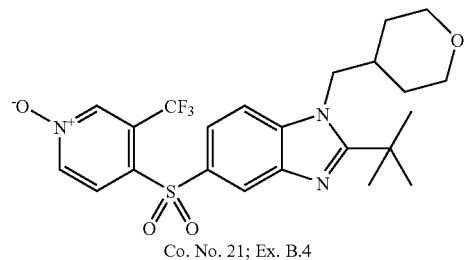
Co. No. 21; Ex. B.4
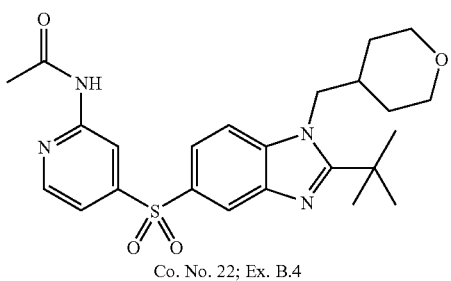
Co. No. 22; Ex. B.4
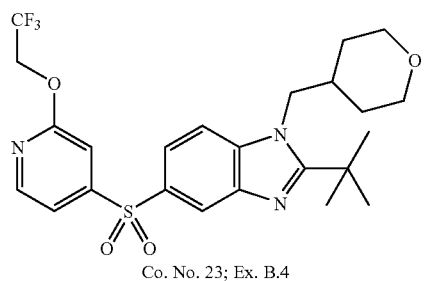
Co. No. 23; Ex. B.4
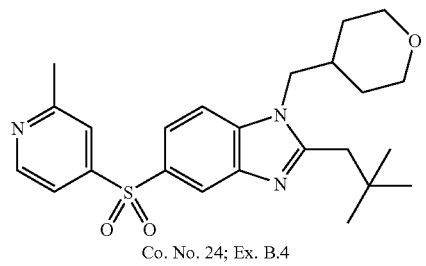
Co. No. 24; Ex. B.4
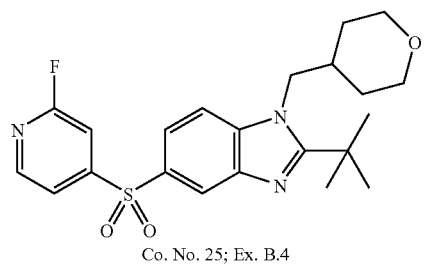
Co. No. 25; Ex. B.4
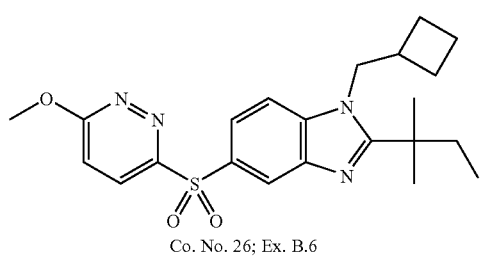
Co. No. 26; Ex. B.6
TABLE F-1-continued
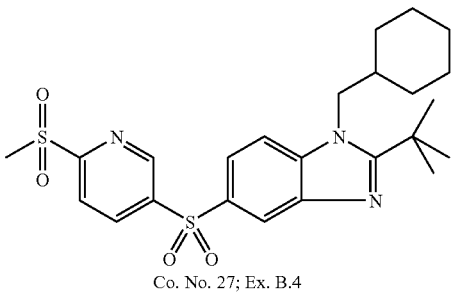
Co. No. 27; Ex. B.4
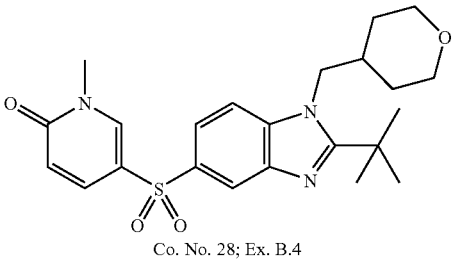
Co. No. 28; Ex. B.4
TABLE F-2
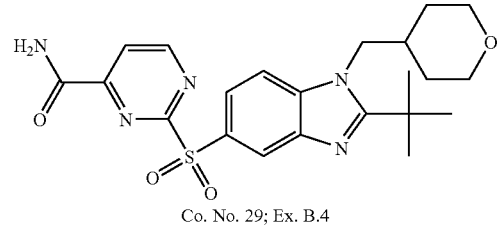
Co. No. 29; Ex. B.4
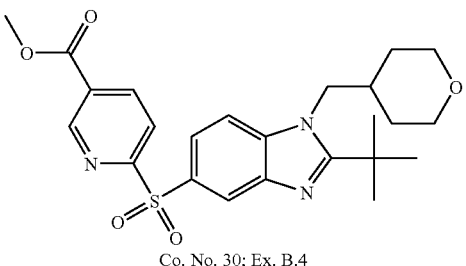
Co. No. 30; Ex. B.4
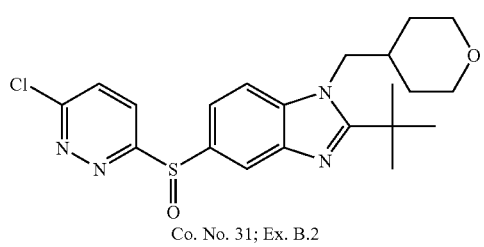
Co. No. 31; Ex. B.2
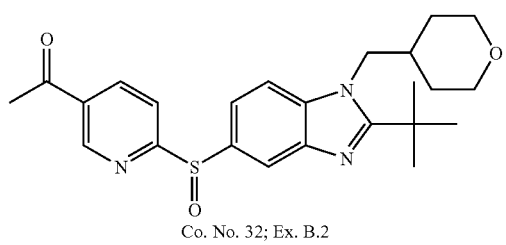
Co. No. 32; Ex. B.2

TABLE F-2-continued
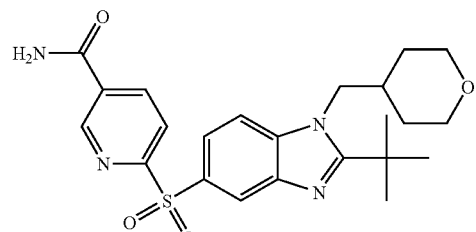
Co. No. 33; Ex. B.2
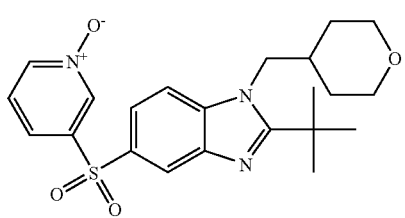 [SMILES: CC(C)(C)c1nc2cc(S(=O)(=O)c3ccc[n+]([O-])c3)ccc2n1CC1CCOCC1]
Co. No. 34; Ex. B.7
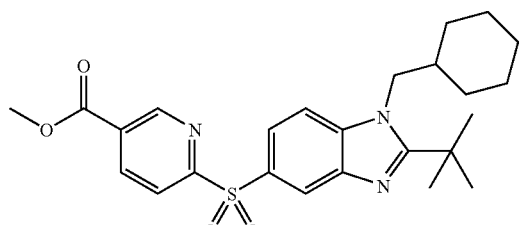
Co. No. 35; Ex. B.4
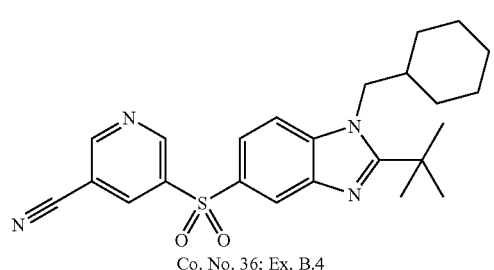
Co. No. 36; Ex. B.4
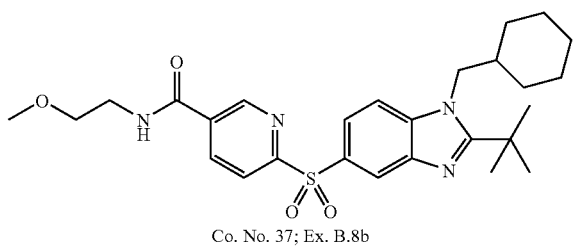
Co. No. 37; Ex. B.8b
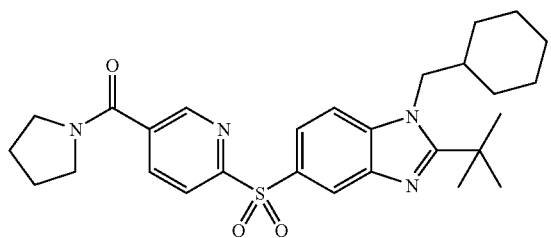 [SMILES: CC(C)(C)c1nc2cc(S(=O)(=O)c3ccc(C(=O)N4CCCC4)cn3)ccc2n1CC1CCCCC1]
Co. No. 38; Ex. B.8b
TABLE F-2-continued
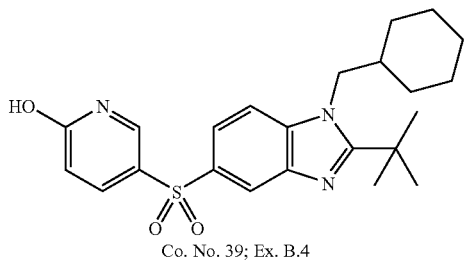
Co. No. 39; Ex. B.4
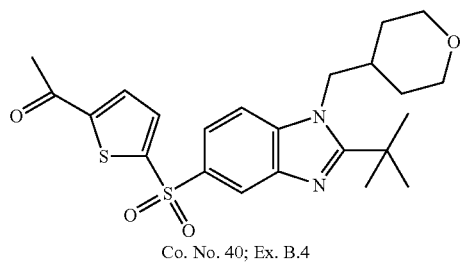
Co. No. 40; Ex. B.4
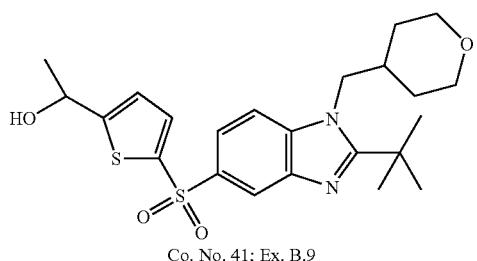
Co. No. 41; Ex. B.9
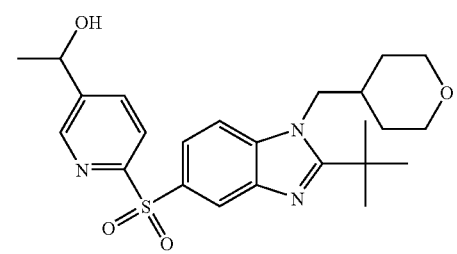 [SMILES: CC(O)c1ccc(S(=O)(=O)c2ccc3c(c2)nc(C(C)(C)C)n3CC2CCOCC2)nc1]
Co. No. 42; Ex. B.10a
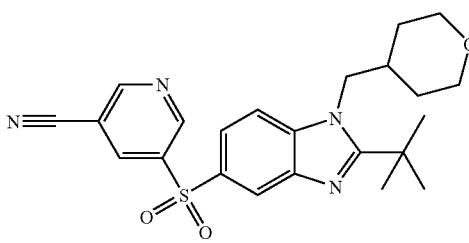
Co. No. 43; Ex. B.11
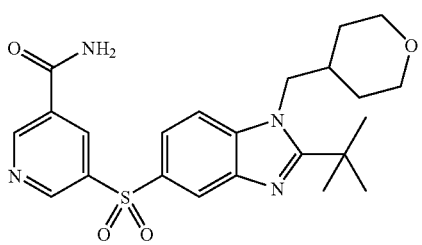 [SMILES: CC(C)(C)c1nc2cc(S(=O)(=O)c3cncc(C(N)=O)c3)ccc2n1CC1CCOCC1]
Co. No. 44; Ex. B.12

TABLE F-2-continued
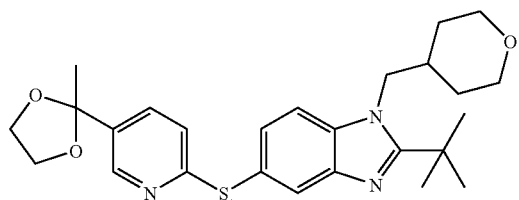
Co. No. 45; Ex. B.13
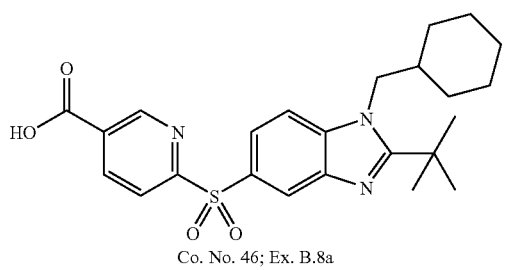
Co. No. 46; Ex. B.8a
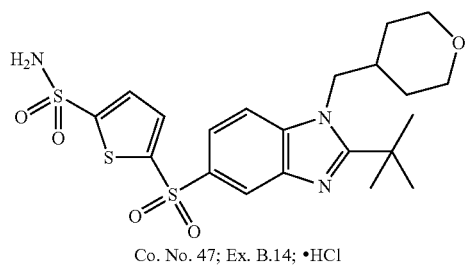
Co. No. 47; Ex. B.14; •HCl
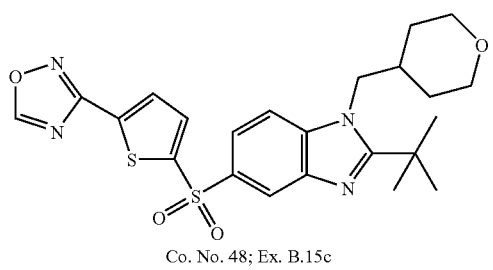
Co. No. 48; Ex. B.15c
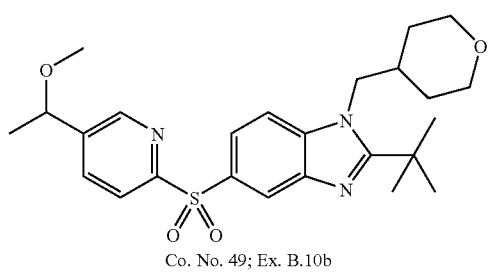
Co. No. 49; Ex. B.10b
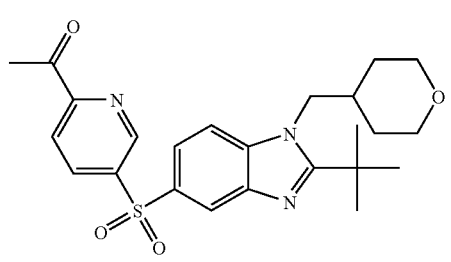 [SMILES: CC(=O)c1ccc(S(=O)(=O)c2ccc3c(c2)nc(C(C)(C)C)n3CC2CCOCC2)cn1]
Co. No. 50; Ex. B.4
TABLE F-2-continued
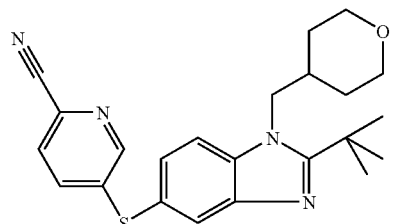
Co. No. 51; Ex. B.4
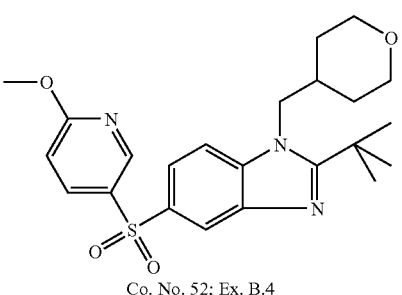
Co. No. 52; Ex. B.4
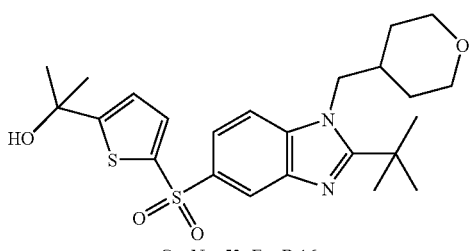
Co. No. 53; Ex. B.16
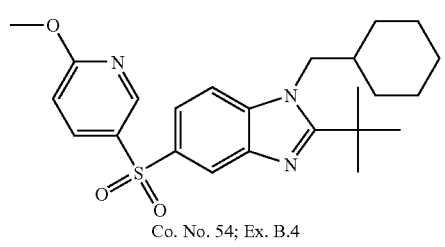
Co. No. 54; Ex. B.4
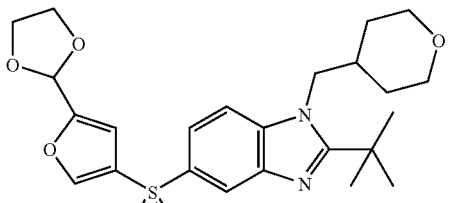
Co. No. 55; Ex. B.4
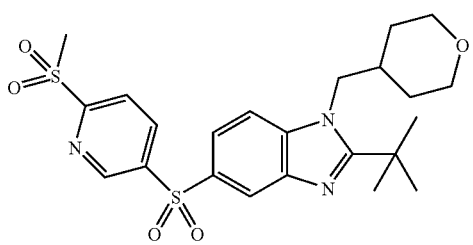 [SMILES: CC(C)(C)c1nc2cc(S(=O)(=O)c3ccc(S(C)(=O)=O)nc3)ccc2n1CC1CCOCC1]
Co. No. 56; Ex. B.4

TABLE F-2-continued
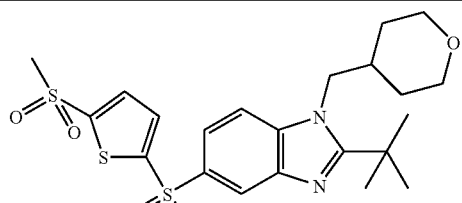
Co. No. 57; Ex. B.4
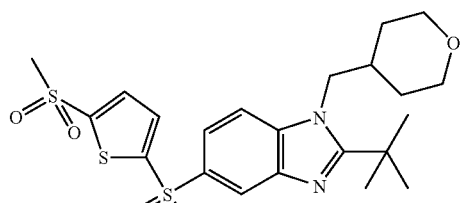
Co. No. 58; Ex. B.14; •HCl
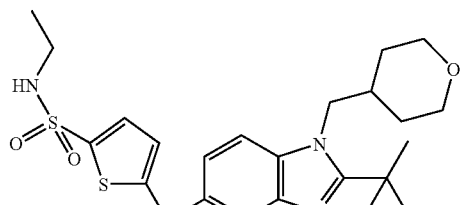
Co. No. 59; Ex. B.4
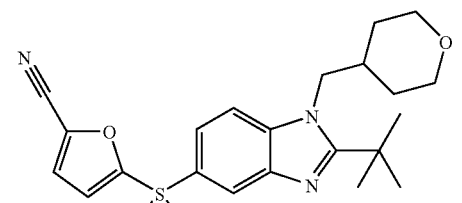
Co. No. 60; Ex. B.4
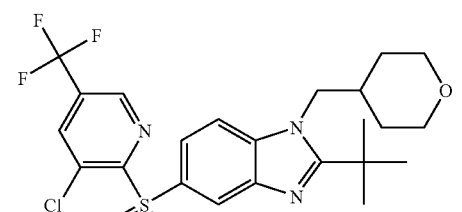
Co. No. 61; Ex. B.3
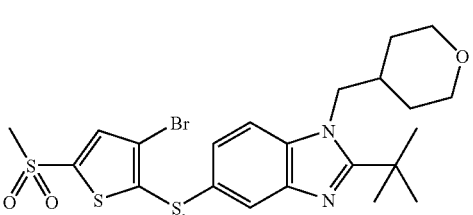
Co. No. 62; Ex. B.4
TABLE F-2-continued
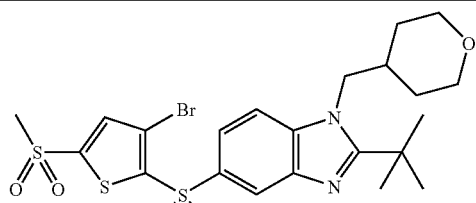
Co. No. 63; Ex. B.14; •HCl
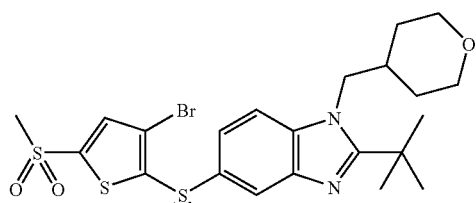
Co. No. 64; Ex. B.17; •CH$_3$SO$_2$OH
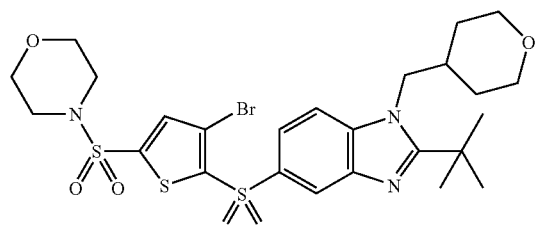
Co. No. 65; Ex. B.4
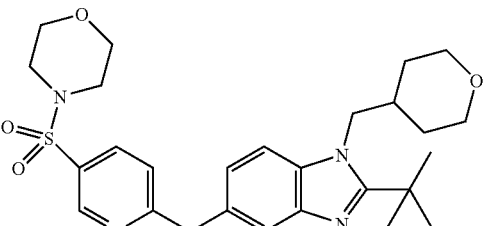
Co. No. 66; Ex. B.4
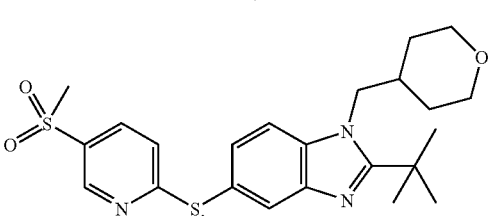
Co. No. 67; Ex. B.4
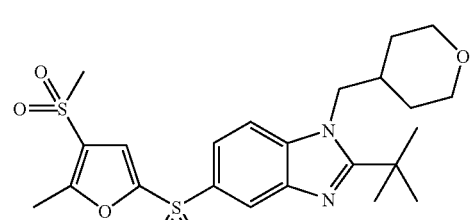
Co. No. 68; Ex. B.4

TABLE F-2-continued
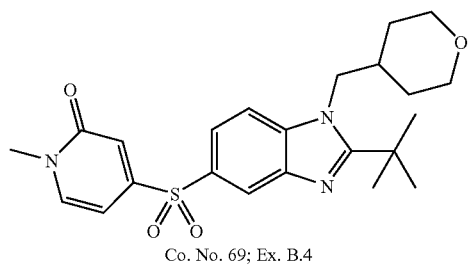
Co. No. 69; Ex. B.4
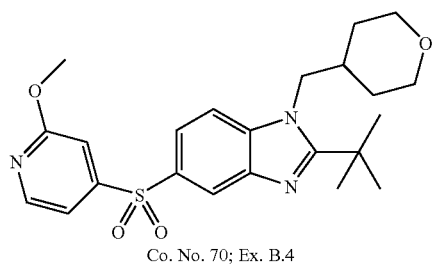
Co. No. 70; Ex. B.4
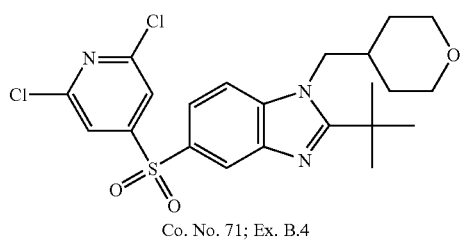
Co. No. 71; Ex. B.4
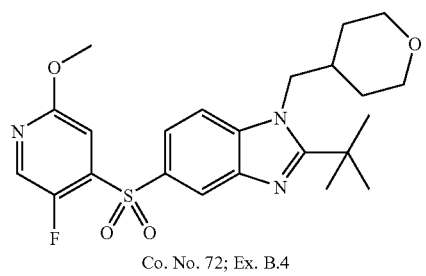
Co. No. 72; Ex. B.4
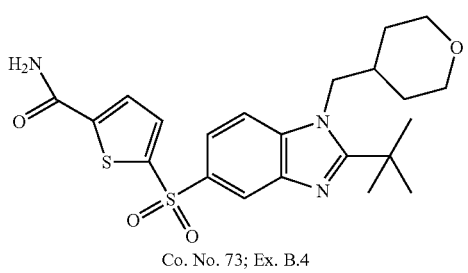
Co. No. 73; Ex. B.4
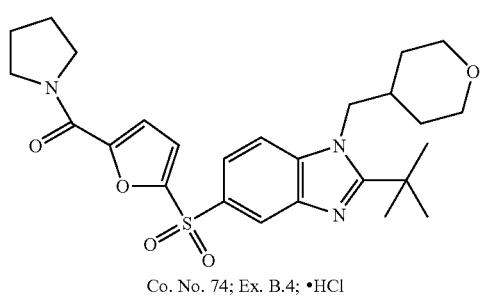
Co. No. 74; Ex. B.4; •HCl
TABLE F-2-continued
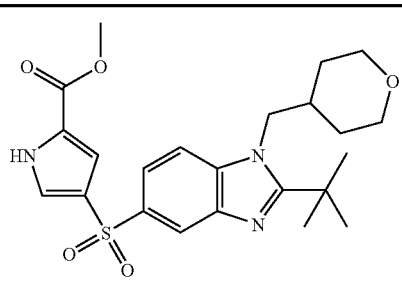
Co. No. 75; Ex. B.4
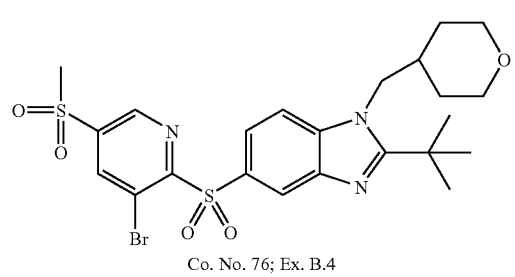
Co. No. 76; Ex. B.4
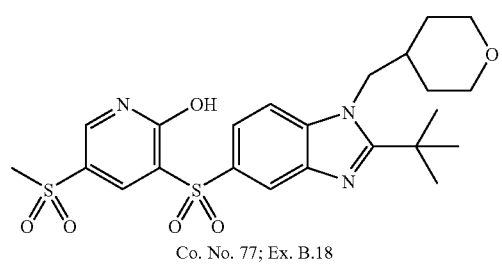
Co. No. 77; Ex. B.18
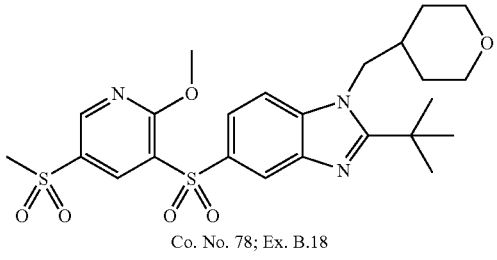
Co. No. 78; Ex. B.18
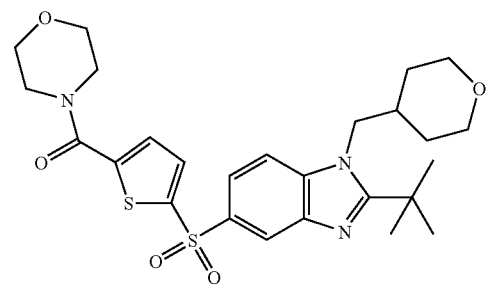 [SMILES: CC(C)(C)c1nc2cc(S(=O)(=O)c3ccc(C(=O)N4CCOCC4)s3)ccc2n1CC1CCOCC1]
Co. No. 79; Ex. B.4

TABLE F-2-continued
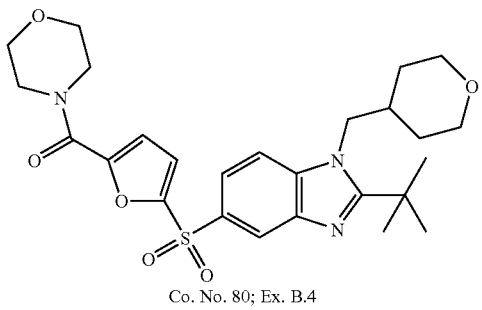
Co. No. 80; Ex. B.4
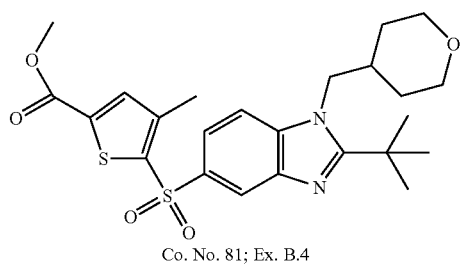
Co. No. 81; Ex. B.4
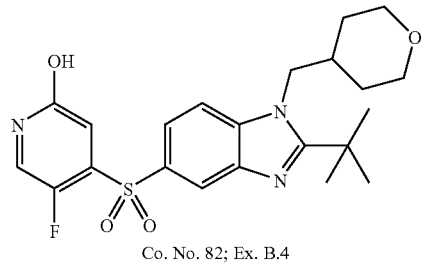
Co. No. 82; Ex. B.4
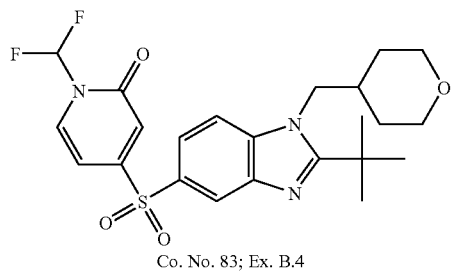
Co. No. 83; Ex. B.4
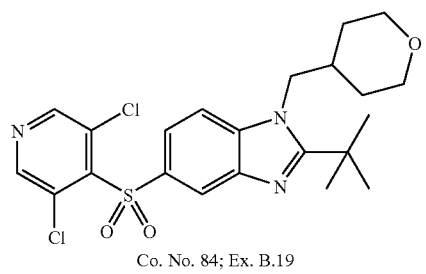
Co. No. 84; Ex. B.19
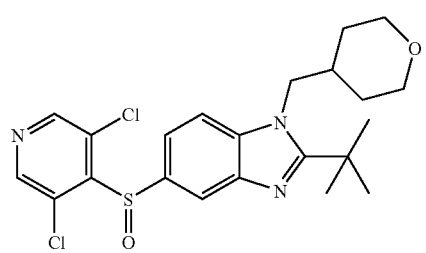 [SMILES: CC(C)(C)c1nc2cc(S(=O)c3c(Cl)cncc3Cl)ccc2n1CC1CCOCC1]
TABLE F-2-continued
Co. No. 85; Ex. B.19
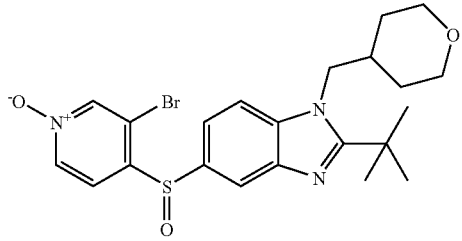
Co. No. 86; Ex. B.20
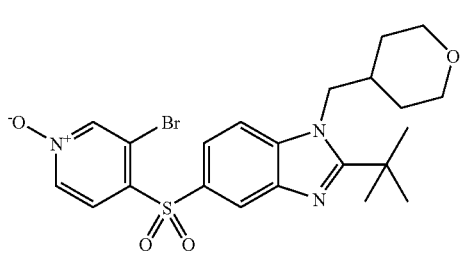
Co. No. 87; Ex. B.20
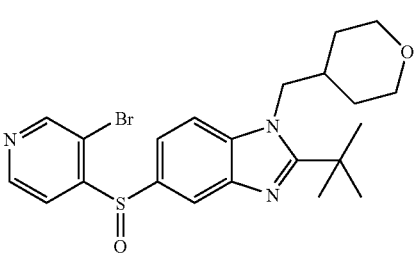 [SMILES: CC(C)(C)c1nc2cc(S(=O)c3ccncc3Br)ccc2n1CC1CCOCC1]
Co. No. 88; Ex. B.20
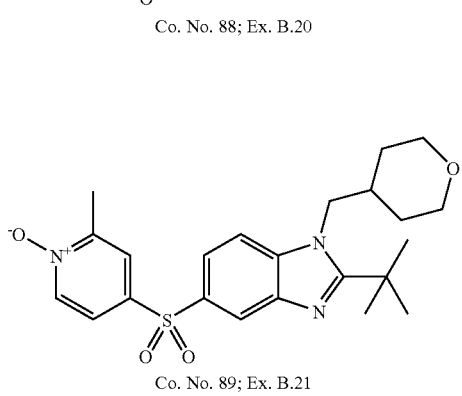
Co. No. 89; Ex. B.21
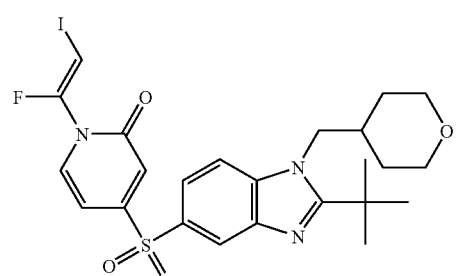
Co. No. 90; Ex. B.4

TABLE F-2-continued
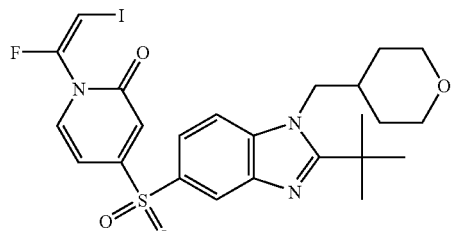
Co. No. 91; Ex. B.4
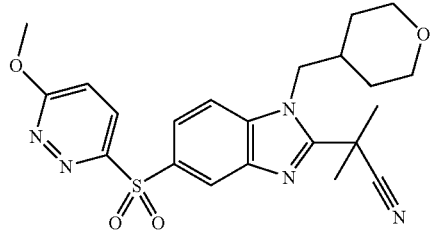 [SMILES: COc1ccc(S(=O)(=O)c2ccc3c(c2)nc(C(C)(C)C#N)n3CC2CCOCC2)nn1]
Co. No. 92; Ex. B.4
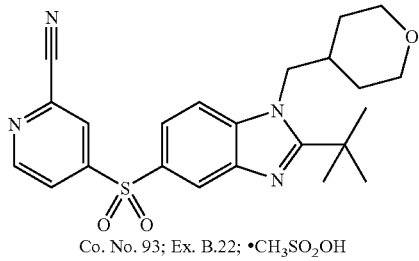
Co. No. 93; Ex. B.22; •CH$_3$SO$_2$OH
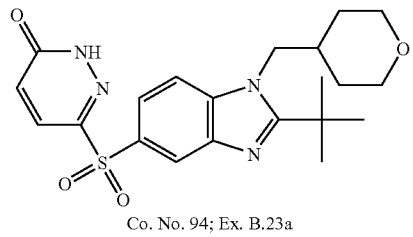
Co. No. 94; Ex. B.23a
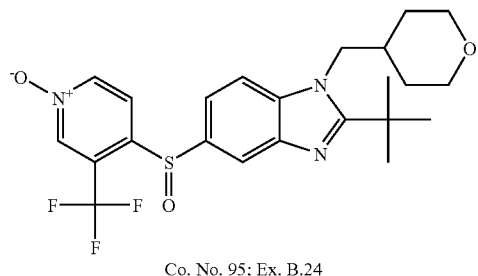
Co. No. 95; Ex. B.24
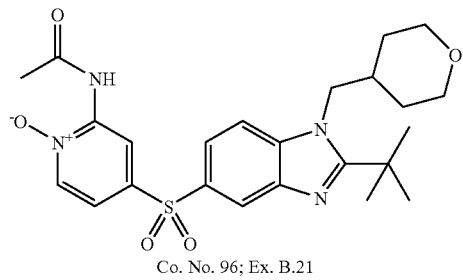
Co. No. 96; Ex. B.21
TABLE F-2-continued
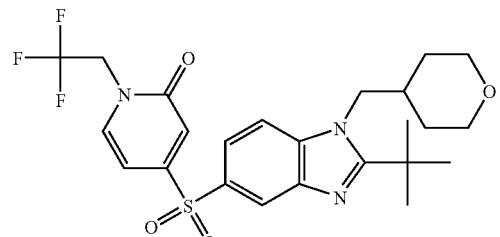
Co. No. 97; Ex. B.4
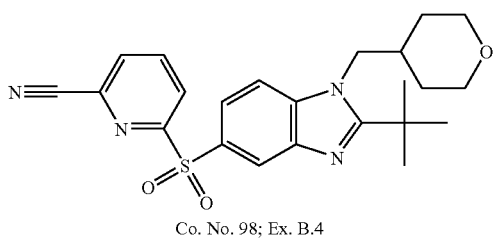
Co. No. 98; Ex. B.4
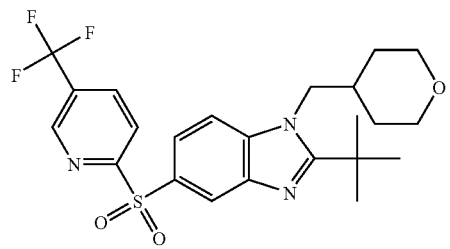 [SMILES: CC(C)(C)c1nc2cc(S(=O)(=O)c3ccc(C(F)(F)F)cn3)ccc2n1CC1CCOCC1]
Co. No. 99; Ex. B.4
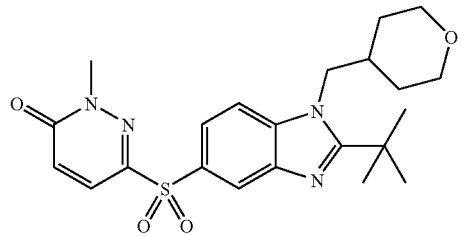 [SMILES: Cn1nc(S(=O)(=O)c2ccc3c(c2)nc(C(C)(C)C)n3CC2CCOCC2)ccc1=O]
Co. No. 100; Ex. B.23b
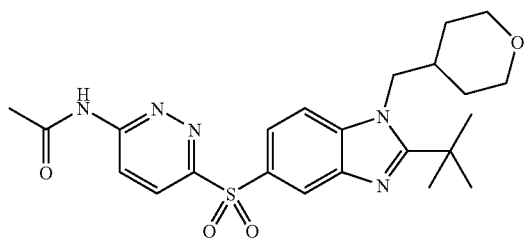 [SMILES: CC(=O)Nc1ccc(S(=O)(=O)c2ccc3c(c2)nc(C(C)(C)C)n3CC2CCOCC2)nn1]
Co. No. 101; Ex. B.25
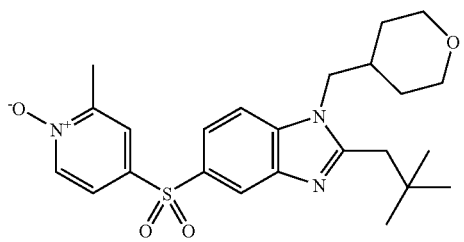
Co. No. 102; Ex. B.21

TABLE F-2-continued
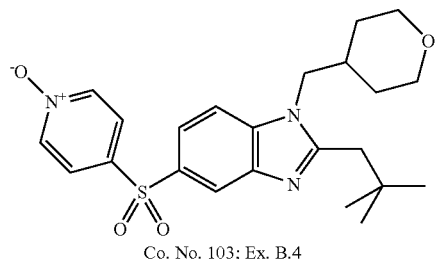
Co. No. 103; Ex. B.4
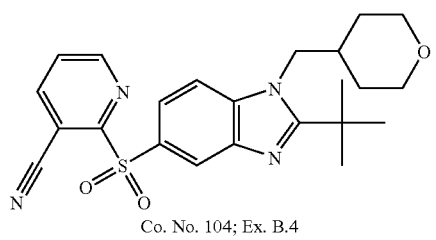
Co. No. 104; Ex. B.4
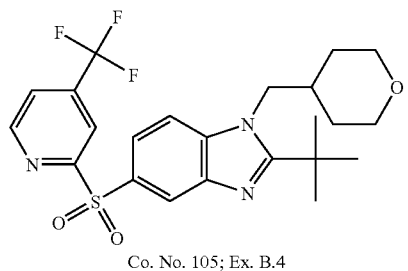
Co. No. 105; Ex. B.4
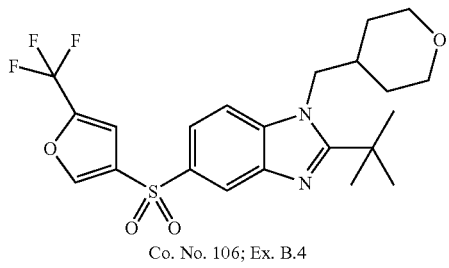
Co. No. 106; Ex. B.4
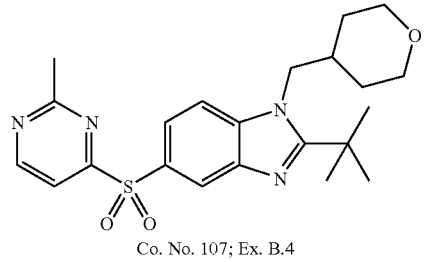
Co. No. 107; Ex. B.4
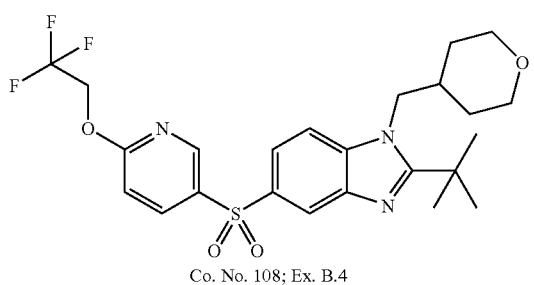
Co. No. 108; Ex. B.4
TABLE F-2-continued
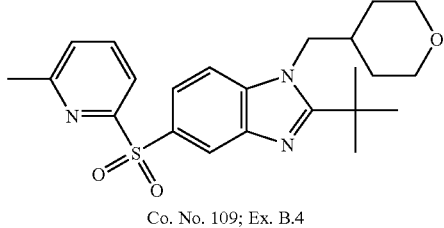
Co. No. 109; Ex. B.4
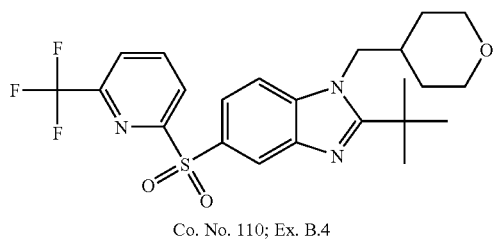
Co. No. 110; Ex. B.4
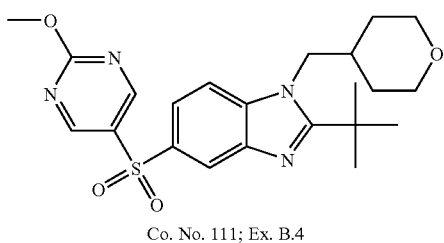
Co. No. 111; Ex. B.4
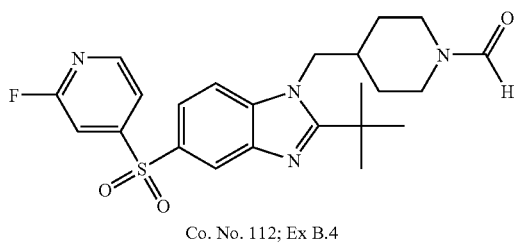
Co. No. 112; Ex B.4
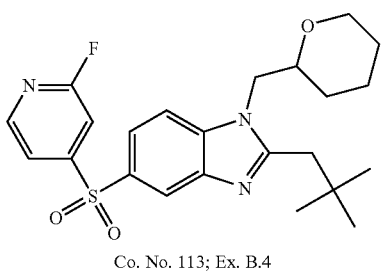
Co. No. 113; Ex. B.4
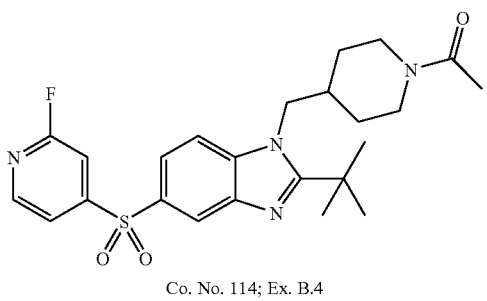
Co. No. 114; Ex. B.4

TABLE F-2-continued
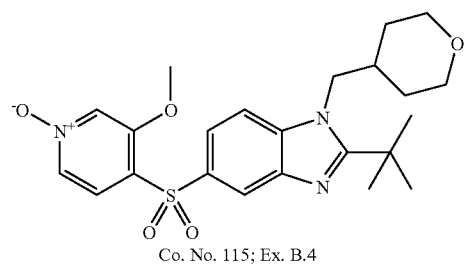
Co. No. 115; Ex. B.4
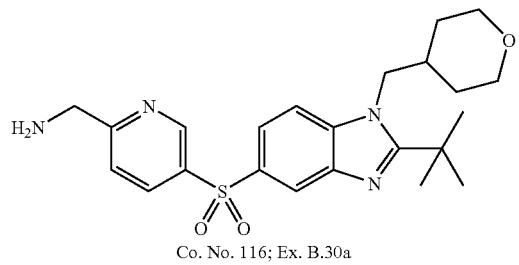
Co. No. 116; Ex. B.30a
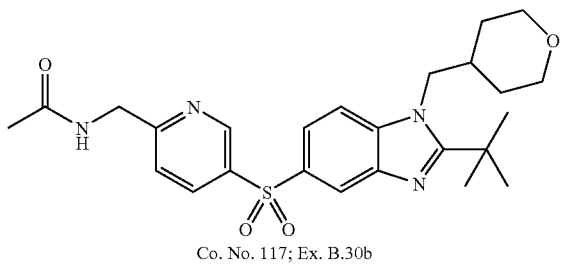
Co. No. 117; Ex. B.30b
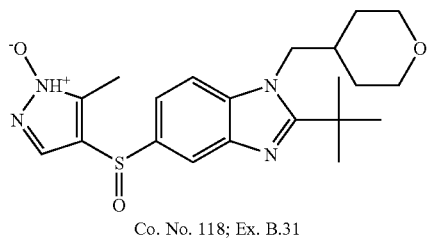
Co. No. 118; Ex. B.31
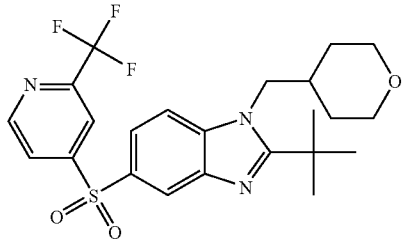 [SMILES: CC(C)(C)c1nc2cc(S(=O)(=O)c3ccnc(C(F)(F)F)c3)ccc2n1CC1CCOCC1]
Co. No. 119; Ex. B.4
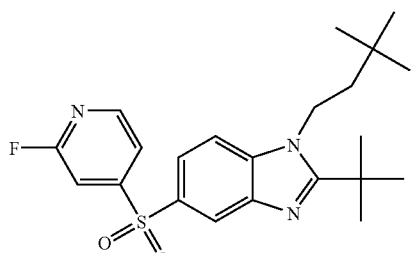
Co. No. 120; Ex. B.4
TABLE F-2-continued
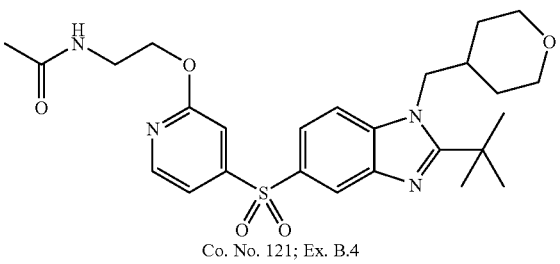
Co. No. 121; Ex. B.4
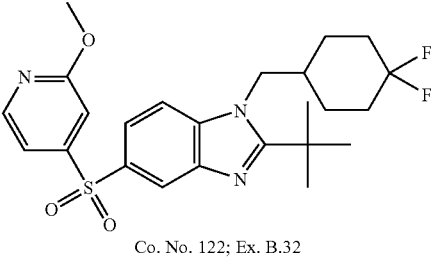
Co. No. 122; Ex. B.32
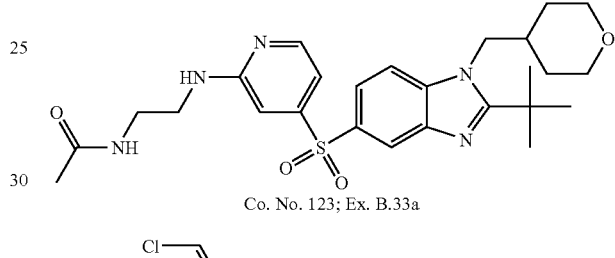
Co. No. 123; Ex. B.33a
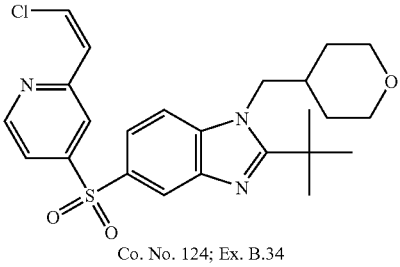
Co. No. 124; Ex. B.34
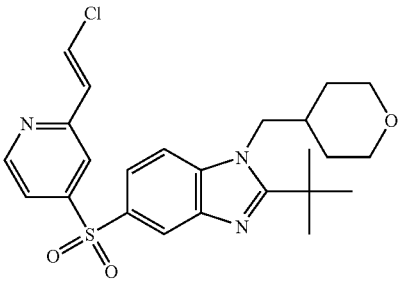 [SMILES: CC(C)(C)c1nc2cc(S(=O)(=O)c3ccnc(/C=C/Cl)c3)ccc2n1CC1CCOCC1]
Co. No. 125, Ex. B.34
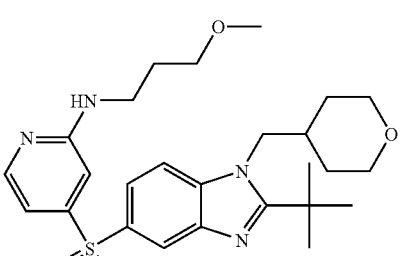
Co. No. 126; Ex. B.33a TABLE F-2-continued
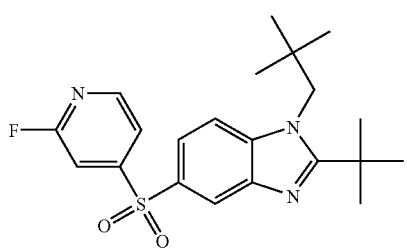 [SMILES: CC(C)(C)Cn1c(C(C)(C)C)nc2cc(S(=O)(=O)c3ccnc(F)c3)ccc21]
Co. No. 127; Ex. B.4
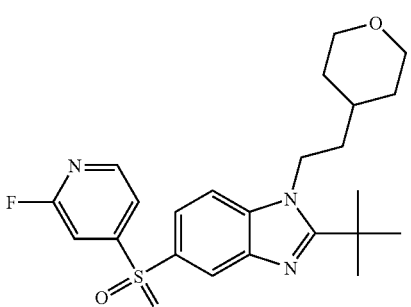
Co. No. 128; Ex. B.4
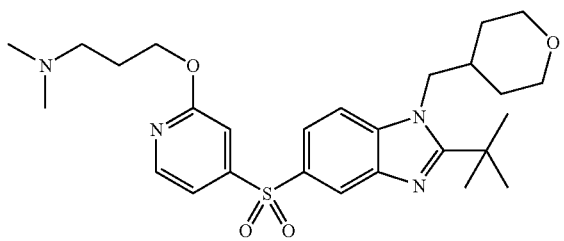 [SMILES: CN(C)CCCOc1cc(S(=O)(=O)c2ccc3c(c2)nc(C(C)(C)C)n3CC2CCOCC2)ccn1]
Co. No. 129; Ex. B.33d
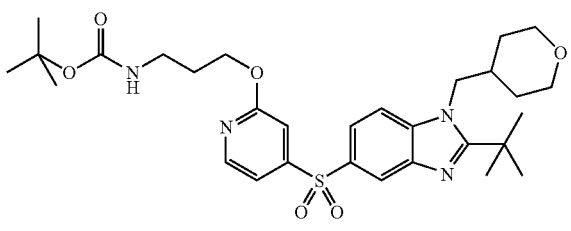 [SMILES: CC(C)(C)OC(=O)NCCCOc1cc(S(=O)(=O)c2ccc3c(c2)nc(C(C)(C)C)n3CC2CCOCC2)ccn1]
Co. No. 130; Ex. B.33d
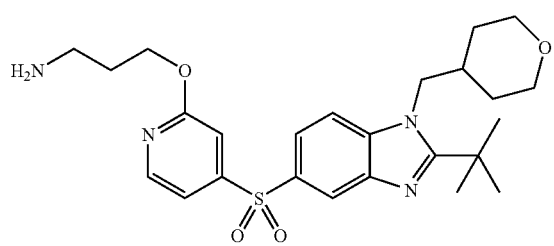 [SMILES: CC(C)(C)c1nc2cc(S(=O)(=O)c3ccnc(OCCCN)c3)ccc2n1CC1CCOCC1]
Co. No. 131; Ex. B.33d
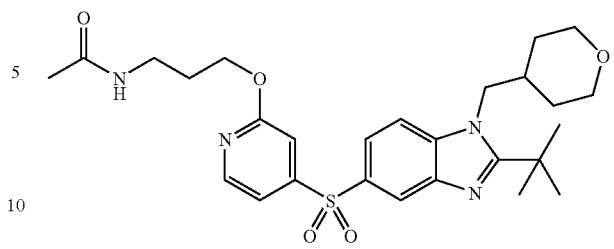
Co. No. 132; Ex. B.33f; •HCl
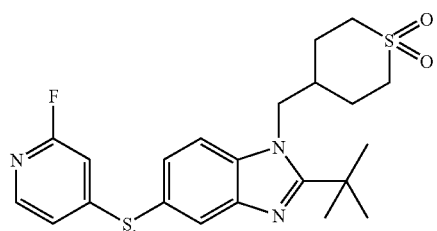
Co. No. 133; Ex. B.4
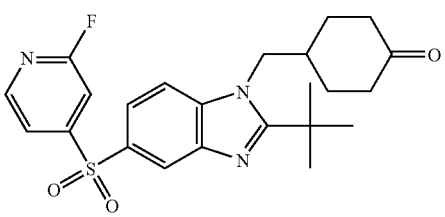 [SMILES: CC(C)(C)c1nc2cc(S(=O)(=O)c3ccnc(F)c3)ccc2n1CC1CCC(=O)CC1]
Co. No. 134; Ex. B.35b
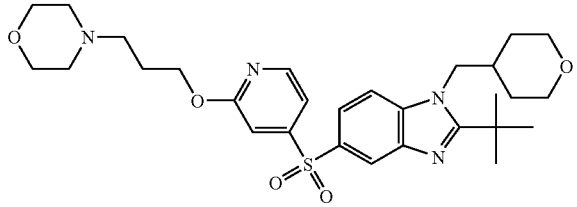 [SMILES: CC(C)(C)c1nc2cc(S(=O)(=O)c3ccnc(OCCCN4CCOCC4)c3)ccc2n1CC1CCOCC1]
Co. No. 135; Ex. B.33b; •3HCl
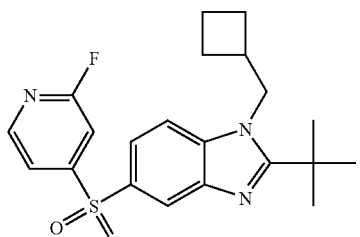
Co. No. 136; Ex. B.36; •HCl•H$_2$O
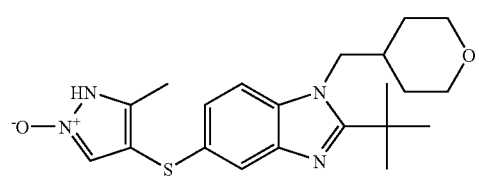
Co. No. 137; Ex. B.31

TABLE F-2-continued
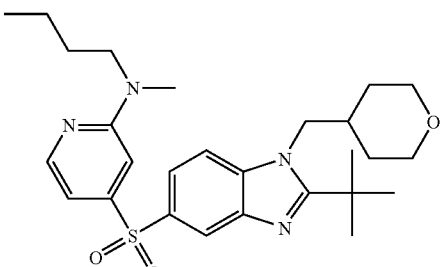
Co. No. 138; Ex. B.37; •2HCl•H₂O•0.5Cl•0.5H₄N
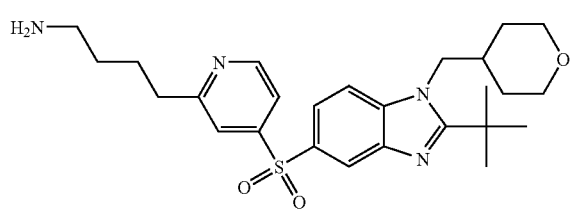 [SMILES: CC(C)(C)c1nc2cc(S(=O)(=O)c3ccnc(CCCCN)c3)ccc2n1CC1CCOCC1]
Co. No. 139, Ex. B.38b
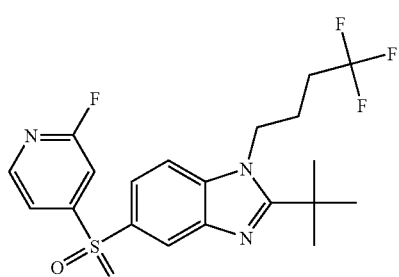
Co. No. 140; Ex. B.4
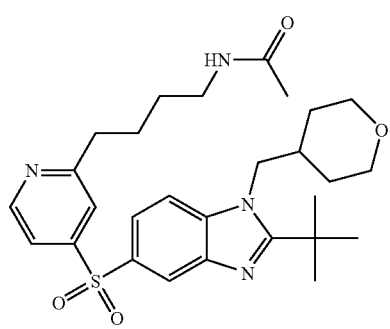 [SMILES: CC(=O)NCCCCc1cc(S(=O)(=O)c2ccc3c(c2)nc(C(C)(C)C)n3CC2CCOCC2)ccn1]
Co. No. 141; Ex. B.38c; 2H₂O•2HCl
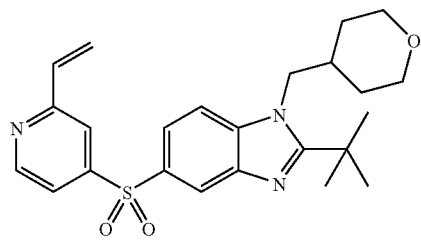 [SMILES: C=Cc1cc(S(=O)(=O)c2ccc3c(c2)nc(C(C)(C)C)n3CC2CCOCC2)ccn1]
Co. No. 142; Ex. B.39a
TABLE F-2-continued
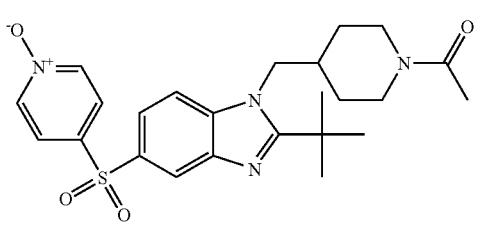
Co. No. 143; Ex. B.21
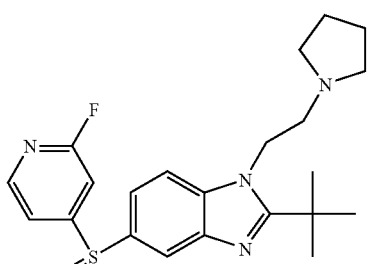
Co. No. 144; Ex. B.41
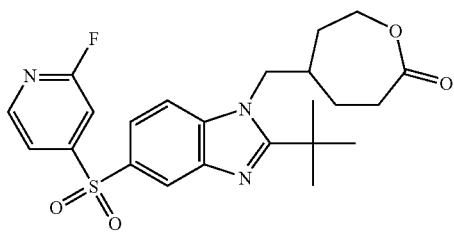 [SMILES: CC(C)(C)c1nc2cc(S(=O)(=O)c3ccnc(F)c3)ccc2n1CC1CCOC(=O)CC1]
Co. No. 145; Ex. B.4
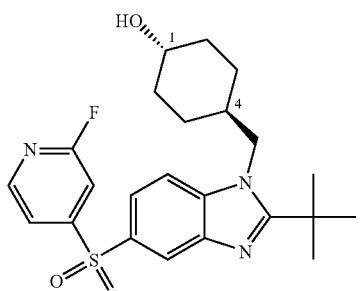
Co. No. 146; Ex. B.35a, 1,4-TRANS
(relative; mixture)
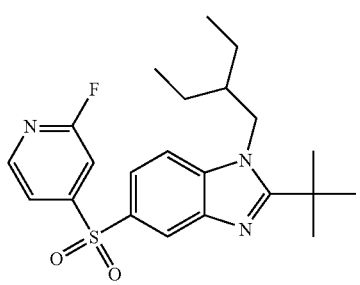 [SMILES: CCC(CC)Cn1c(C(C)(C)C)nc2cc(S(=O)(=O)c3ccnc(F)c3)ccc21]
Co. No. 147; Ex. B.4

TABLE F-2-continued
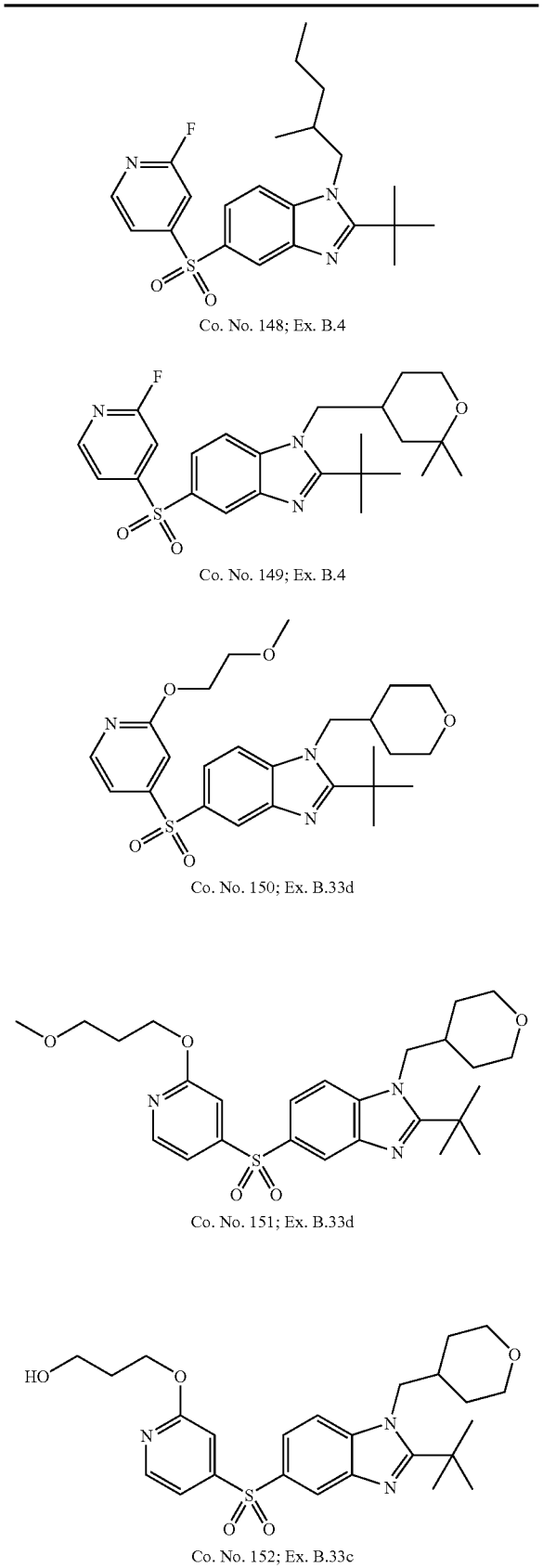
Co. No. 148; Ex. B.4
Co. No. 149; Ex. B.4
Co. No. 150; Ex. B.33d
Co. No. 151; Ex. B.33d
Co. No. 152; Ex. B.33c
TABLE F-2-continued
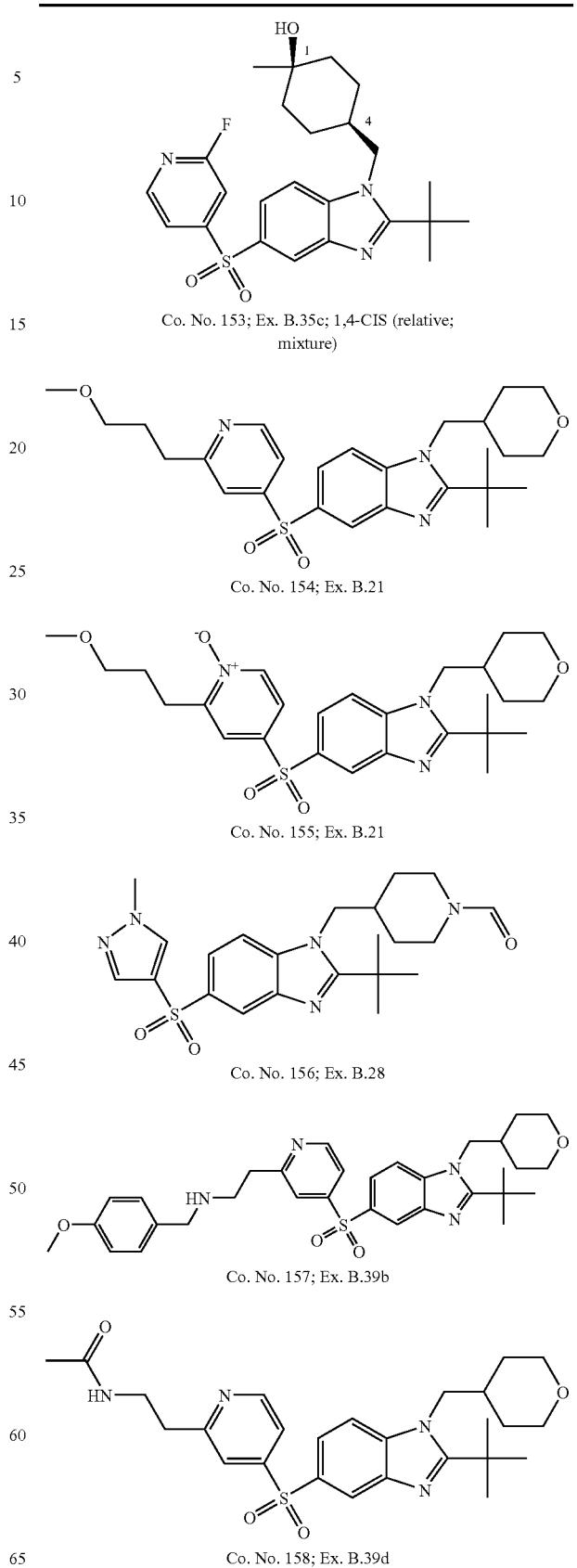
Co. No. 153; Ex. B.35c; 1,4-CIS (relative; mixture)
Co. No. 154; Ex. B.21
Co. No. 155; Ex. B.21
Co. No. 156; Ex. B.28
Co. No. 157; Ex. B.39b
Co. No. 158; Ex. B.39d TABLE F-2-continued
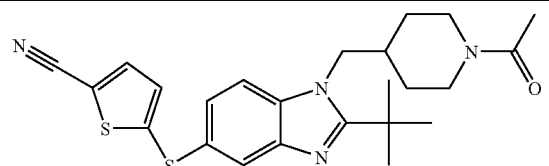
Co. No. 159; Ex. B.26
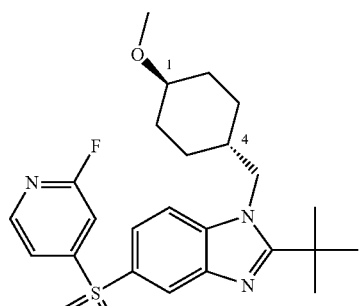
Co. No. 160; Ex. B.4; 1,4-TRANS (relative; mixture)
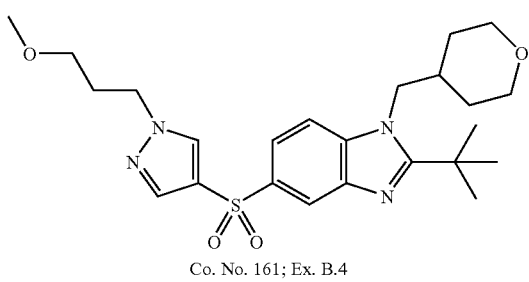
Co. No. 161; Ex. B.4
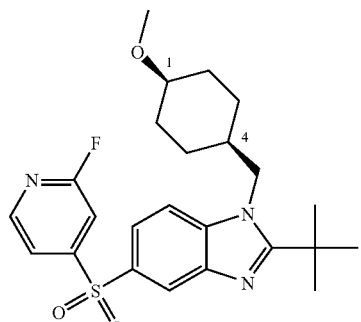
Co. No. 162; Ex. B.4; 1,4-CIS (relative; mixture)
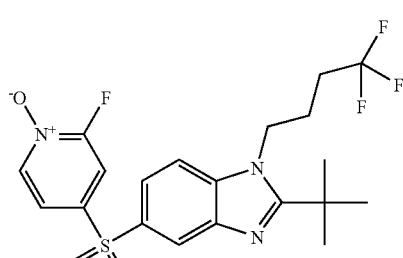
Co. No. 163; Ex. B.29
TABLE F-2-continued
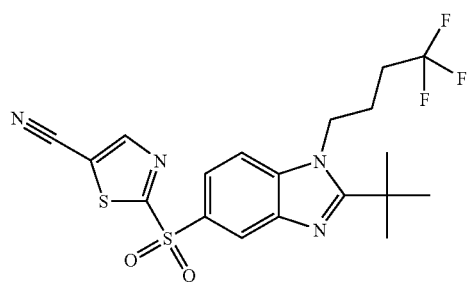 [SMILES: CC(C)(C)c1nc2cc(S(=O)(=O)c3ncc(C#N)s3)ccc2n1CCCC(F)(F)F]
Co. No. 164; Ex. B.4
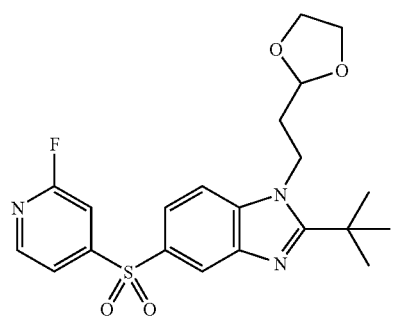 [SMILES: CC(C)(C)c1nc2cc(S(=O)(=O)c3ccnc(F)c3)ccc2n1CCC1OCCO1]
Co. No. 165; Ex. B.40
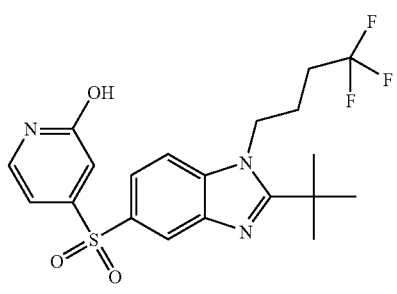 [SMILES: CC(C)(C)c1nc2cc(S(=O)(=O)c3ccnc(O)c3)ccc2n1CCCC(F)(F)F]
Co. No. 166; Ex. B.4
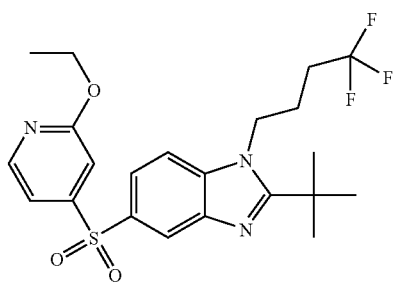 [SMILES: CCOc1cc(S(=O)(=O)c2ccc3c(c2)nc(C(C)(C)C)n3CCCC(F)(F)F)ccn1]
Co. No. 167; Ex. B.4
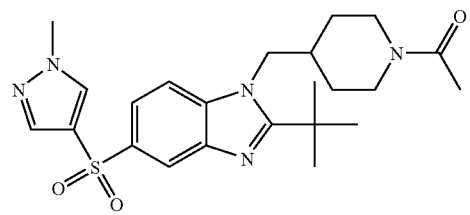 [SMILES: CC(=O)N1CCC(Cn2c(C(C)(C)C)nc3cc(S(=O)(=O)c4cnn(C)c4)ccc32)CC1]
Co. No. 168; Ex. B.27

TABLE F-2-continued

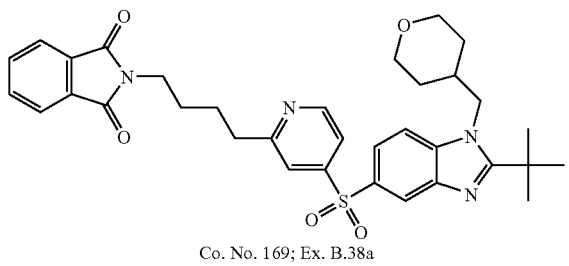

Co. No. 169; Ex. B.38a

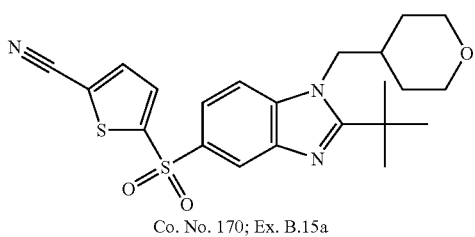

Co. No. 170; Ex. B.15a

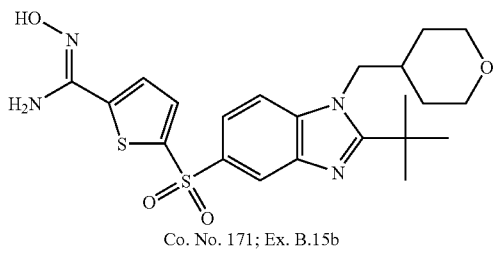

Co. No. 171; Ex. B.15b

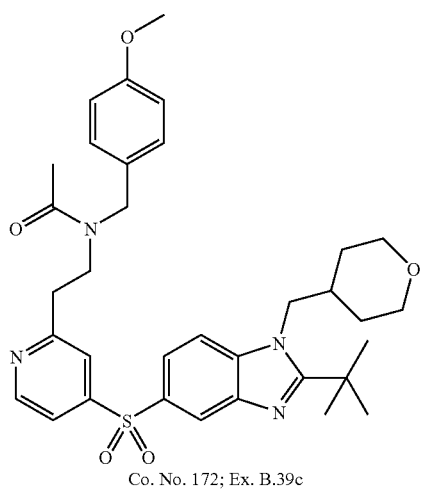

Co. No. 172; Ex. B.39c

Compound Identification

LMCS—General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS—General Procedure B

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS Method 1

In addition to general procedure A: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Method 2

In addition to general procedure A: Reversed phase HPLC was carried out on an Atlantis C18 column (3.5 μm, 4.6×100 mm) (3.5 μm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 μl was used. Cone voltage was 10 V for positive ionization mode and 20 V for negative ionization mode.

LCMS Method 3

In addition to general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 μl was used. Cone voltage was 10 V for positive ionization mode and 20 V for negative ionization mode.

LCMS Method 4

In addition to general procedure A: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Method 5

In addition to general procedure B: Reversed phase UPLC (Ultra Performance Liquid Chromatography) was carried out on a bridged ethylsiloxane/silica (BEH) C18 column (1.7 μm, 2.1×50 mm) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

LCMS Method 6

In addition to general procedure A: Reversed phase HPLC was carried out on a Xbridge C18 column (3.5 µm, 4.6×100 mm) (3.5 µm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 µl was used. Cone voltage was 10 V for positive ionization mode and 20 V for negative ionization mode.

Melting Points

For a number of compounds, melting points were determined with a DSC823e (Mettler-Toledo). In this method, melting points were measured with a temperature gradient of 30° C./minute. Maximum temperature was 400° C.

For a number of compounds melting points were determined with a Büchi melting point apparatus (in open capillary tubes). The heating medium was a metal block. The melting of the sample was visually observed by a magnifying lense and a big light contrast. Melting points were measured with a temperature gradient of either 3 or 10° C./minute. Maximum temperature was 300° C.

For a number of compounds, melting points were obtained with a Kofler hot bench, consisting of a heated plate with linear temperature gradient, a sliding pointer and a temperature scale in degrees Celsius.

Values are either peak values or melt ranges, and are obtained with experimental uncertainties that are commonly associated with this analytical method.

TABLE F-3

Analytical data - Retention time ($R_t$ in minutes), $(MH)^+$ peak, LCMS procedure and physico-chemical data (m.p. is defined as melting point).

| Co. No. | $R_t$ | $(MH)^+$ | Procedure | Physico-chemical data |
|---|---|---|---|---|
| 3 | 4.51 | 430 | 1 | — |
| 4 | 5.14 | 456 | 1 | m.p.: >120° C. (Kofler) |
| 5 | 5.92 | 501 | 1 | m.p.: 192-193° C. (Kofler) |
| 6 | 5.08 | 498 | 1 | m.p.: 259° C. (Kofler) |
| 7 | 1.19 | 568 | 5 | m.p.: 198° C. (Kofler) |
| 10 | 6.13 | 482 | 1 | m.p.: 137.43° C. (DSC) |
| 11 | 5.18 | 445 | 1 | m.p.: 174-180° C. (Kofler) |
| 12 | 1.01 | 446 | 5 | m.p.: 234.8° C. (DSC) |
| 13 | 5.26 | 428 | 1 | m.p.: 180.1° C. (DSC) |
| 14 | 5.47 | 480 | 4 | — |
| 15 | 1.19 | 432 | 5 | — |
| 16 | 4.87 | 457 | 1 | m.p.: 247.1° C. (DSC) |
| 17 | 5.51 | 439 | 1 | m.p.: 201.2° C. (DSC) |
| 18 | 5.77 | 448 | 1 | m.p.: 201.0° C. (DSC) |
| 19 | 4.85 | 429 | 1 | m.p.: 235.9° C. (DSC) |
| 20 | 1.05 | 481 | 5 | m.p.: 165.2° C. (DSC) |
| 21 | 5.24 | 498 | 1 | m.p.: 205.8° C. (DSC) |
| 22 | 4.56 | 471 | 4 | m.p.: 262.3° C. (DSC) |
| 23 | 5.79 | 512 | 4 | m.p.: 166.7° C. (DSC) |
| 24 | 1.19 | 442 | 5 | m.p.: 207.1° C. (DSC) |
| 26 | 6.29 | 429 | 1 | HCl-salt |
| 27 | 4.90 | 490 | 1 | m.p.: 200° C. (Kofler) |
| 28 | 4.70 | 444 | 1 | m.p.: 170° C. (Kofler) |
| 29 | 0.75 | 458 | 3 | m.p.: 220-222° C. (Kofler) |
| 30 | 0.87 | 472 | 3 | m.p.: 195-197° C. (Kofler) |
| 31 | 5.09 | 433 | 1 | |
| 32 | 4.95 | 440 | 1 | |
| 33 | 4.59 | 457 | 1 | |
| 34 | 0.81 | 430 | 3 | |
| 35 | 6.68 | 470 | 1 | |
| 36 | 1.27 | 437 | 3 | m.p.: 215-216° C. (Kofler) |
| 37 | 6.33 | 513 | 1 | m.p.: 206-207° C. (Kofler) |
| 38 | 6.42 | 509 | 1 | |
| 39 | 6.12 | 428 | 1 | |
| 40 | 1.15 | 461 | 5 | m.p.: 151° C. (Kofler) |
| 41 | 1.08 | 463 | 5 | m.p.: 192° C. (Kofler) |
| 42 | 4.79 | 458 | 1 | m.p.: 177-179° C. (Kofler) |
| 43 | 5.33 | 439 | 1 | m.p.: 240° C. (Kofler) |
| 44 | 4.63 | 457 | 1 | m.p.: 259° C. (Kofler) |
| 45 | 5.47 | 500 | 1 | m.p.: 191° C. (Kofler) |
| 46 | 5.57 | 456 | 1 | |
| 47 | 5.11 | 498 | 1 | m.p.: 255-260° C. (Kofler) HCl-salt |
| 48 | 5.74 | 487 | 1 | m.p.: 199° C. (Kofler) |
| 49 | 5.35 | 472 | 1 | m.p.: 140° C. (Kofler) |
| 50 | 5.59 | 456 | 1 | m.p.: 162° C. (Kofler) |
| 51 | 5.43 | 439 | 1 | m.p.: 228° C. (Kofler) |
| 52 | 5.66 | 444 | 1 | m.p.: 198° C. (Kofler) |
| 53 | 5.35 | 477 | 1 | m.p.: 258° C. (Kofler) |
| 55 | 5.35 | 475 | 1 | m.p.: 141.0° C. (Kofler) |
| 56 | 1.05 | 492 | 5 | m.p.: 150-160° C. (Kofler) |
| 57 | 1.09 | 497 | 5 | m.p.: 216° C. (Kofler) |
| 58 | 4.79 | 497 | 4 | m.p.: 224.0° C. (DSC) HCl-salt |
| 59 | 1.15 | 526 | 5 | m.p.: 158° C. (Kofler) |
| 60 | 1.17 | 428 | 5 | m.p.: 145.5-145.7° C. (Büchi) |
| 61 | 6.03 | 516 | 1 | |
| 62 | 1.17 | 575 | 5 | m.p.: 200° C. (Kofler) |
| 63 | see compound 62 (free base) | | | m.p.: 219.36° C. (DSC) HCl-salt |
| 64 | see compound 62 (free base) | | | m.p.: 216.3° C. (DSC) methanesulfonate-salt |
| 65 | 1.26 | 646 | 5 | m.p.: 230° C. (Kofler) |
| 66 | 1.11 | 563 | 5 | m.p.: 224° C. (Kofler) |
| 67 | 1.01 | 492 | 5 | m.p.: 183° C. (Kofler) |
| 68 | 5.35 | 495 | 1 | m.p.: 204-205° C. (Kofler) |
| 69 | 4.73 | 444 | 1 | m.p.: 216° C. (Kofler) |
| 70 | 5.79 | 444 | 1 | |
| 71 | 5.53 | 482 | 4 | m.p.: 198° C. (Kofler) |
| 72 | 1.28 | 462 | 5 | m.p.: 139.6-140.2° C. (Büchi) |
| 73 | 1.02 | 462 | 5 | m.p.: 209.4° C. (DSC) |
| 74 | 1.14 | 500 | 5 | m.p.: 108.5° C. (DSC) HCl-salt |
| 75 | 1.04 | 460 | 5 | m.p.: 231° C. (Kofler) |
| 76 | 5.31 | 570 | 1 | |
| 77 | 4.91 | 507 | 1 | |
| 78 | 5.29 | 522 | 1 | |
| 79 | 1.08 | 532 | 5 | m.p.: 184.6° C. (DSC) |
| 80 | 5.15 | 516 | 1 | m.p.: 172.1° C. (DSC) |
| 81 | 1.26 | 491 | 5 | m.p.: 185.8° C. (DSC) |
| 82 | 1.04 | 448 | 5 | m.p.: 291.8-294.6° C. (Büchi) |
| 83 | 4.89 | 480 | 4 | |
| 84 | 5.98 | 482 | 1 | m.p.: 242.9° C. (DSC) |
| 85 | 5.65 | 466 | 1 | m.p.: 192.9° C. (DSC) |
| 86 | 4.40 | 492 | 1 | |
| 87 | 4.89 | 508 | 1 | m.p.: 205.3° C. (DSC) |
| 88 | 5.20 | 476 | 1 | m.p.: 184.7° C. (DSC) |
| 89 | 4.72 | 444 | 1 | m.p.: 215.3° C. (DSC) |
| 90 | 5.64 | 600 | 1 | m.p.: 113.9° C. (DSC) |
| 91 | 5.44 | 600 | 1 | m.p.: 164.4° C. (DSC) |
| 92 | 1.02 | 456 | 5 | m.p.: 161.1° C. (DSC) |
| 93 | 5.49 | 439 | 1 | m.p.: 215.7° C. (DSC) methanesulfonate-salt |
| 94 | 0.98 | 431 | 5 | m.p.: 218.3° C. (DSC) |
| 95 | 4.87 | 482 | 1 | |
| 96 | 4.39 | 487 | 4 | m.p.: 247.2° C. (DSC) |
| 98 | 1.07 | 439 | 5 | m.p.: 224.5-226.7° C. (Büchi) |
| 99 | 1.23 | 482 | 5 | m.p.: 140.5-142.3° C. (Büchi) |
| 100 | 4.89 | 445 | 1 | m.p.: 224.3° C. (DSC) |
| 101 | 4.88 | 472 | 1 | m.p.: 290.1° C. (DSC) |
| 102 | 4.67 | 458 | 4 | m.p.: 231.7° C. (DSC) |
| 103 | 4.91 | 444 | 1 | m.p.: 259.7° C. (DSC) |
| 104 | 1.03 | 439 | 5 | m.p.: 100.0-105.0° C. (Büchi) |
| 105 | 1.23 | 482 | 5 | m.p.: 139.5-141.0° C. (Büchi) |
| 106 | 1.29 | 471 | 5 | m.p.: 168.0-169.5° C. (Büchi) |

TABLE F-3-continued

Analytical data - Retention time ($R_t$ in minutes), $(MH)^+$ peak, LCMS procedure and physico-chemical data (m.p. is defined as melting point).

| Co. No. | $R_t$ | $(MH)^+$ | Procedure | Physico-chemical data |
|---|---|---|---|---|
| 107 | 5.06 | 429 | 1 | m.p.: 179.7° C. (DSC) |
| 108 | 1.30 | 512 | 5 | |
| 110 | 1.19 | 482 | 5 | m.p.: decomposition at 190° C. (Büchi) |
| 111 | 1.13 | 445 | 5 | m.p.: decomposition at 170° C. (Büchi) |
| 112 | 5.06 | 459 | 1 | m.p.: 196.7° C. (DSC) |
| 113 | 5.74 | 446 | 4 | m.p.: 179.8° C. (DSC) |
| 114 | 5.17 | 473 | 1 | m.p.: 193.9° C. (DSC) |
| 115 | 4.07 | 460 | 4 | |
| 116 | 3.87 | 443 | 4 | |
| 117 | 4.61 | 485 | 1 | m.p.: 199.4° C. (DSC) |
| 118 | 0.99 | 417 | 5 | |
| 119 | 1.28 | 482 | 5 | |
| 120 | 6.79 | 418 | 1 | m.p.: 131.5° C. (DSC) |
| 121 | 5.04 | 515 | 1 | m.p.: 182.3° C. (DSC) |
| 122 | 5.65 | 478 | 4 | |
| 123 | 4.24 | 514 | 4 | m.p.: 217.2° C. (DSC) |
| 124 | 5.43 | 474 | 1 | |
| 125 | 5.94 | 474 | 1 | |
| 126 | 4.83 | 501 | 4 | m.p.: 148.3° C. (DSC) |
| 127 | 5.58 | 404 | 4 | m.p.: 135.4° C. (DSC) |
| 128 | 5.09 | 446 | 4 | m.p.: 177.8° C. (DSC) |
| 129 | 4.67 | 515 | 1 | m.p.: 119.4° C. (DSC) |
| 131 | 4.46 | 487 | 1 | |
| 132 | 6.53 | 529 | 6 | HCl-salt |
| 133 | 5.77 | 480 | 6 | m.p.: 220.8° C. (DSC) |
| 134 | 1.18 | 444 | 5 | m.p.: 164.8° C. (DSC) |
| 136 | 8.02 | 402 | 6 | HCl-salt m.p.: 184.3° C. (DSC) |
| 137 | 0.99 | 417 | 5 | |
| 138 | 5.73 | 499 | 4 | •2HCl•H$_2$O•0.5Cl•0.5H$_4$N |
| 139 | 4.36 | 485 | 1 | |
| 140 | 5.95 | 444 | 1 | m.p.: 138.9° C. (DSC) |
| 141 | 6.31 | 527 | 6 | HCl-salt |
| 142 | 7.03 | 440 | 6 | |
| 143 | 4.97 | 471 | 6 | |
| 144 | 5.76 | 431 | 1 | m.p.: 115.5° C. (DSC) |
| 145 | 5.13 | 460 | 1 | |
| 146 | 7.17 | 446 | 2 | m.p.: 163.6° C. (DSC) |
| 147 | 6.68 | 418 | 1 | m.p.: 130.9° C. (DSC) |
| 148 | 1.41 | 418 | 5 | |
| 149 | 5.70 | 460 | 4 | m.p.: 159.4° C. (DSC) |
| 150 | 7.08 | 488 | 6 | m.p.: 142.9° C. (DSC) |
| 151 | 7.51 | 502 | 6 | m.p.: 106.5° C. (DSC) |
| 152 | 6.62 | 488 | 6 | m.p.: 161.5° C. (DSC) |
| 154 | 6.89 | 486 | 6 | m.p.: 143.4° C. (DSC) |
| 155 | 6.32 | 502 | 6 | |
| 156 | 4.74 | 444 | 6 | m.p.: 213.9° C. (DSC) |
| 157 | 5.16 | 577 | 1 | |
| 158 | 4.60 | 499 | 1 | m.p.: 160.3° C. (DSC) |
| 159 | 6.74 | 485 | 2 | m.p.: 181.2° C. (DSC) |
| 160 | 5.91 | 460 | 1 | |
| 161 | 1.08 | 475 | 5 | |
| 162 | 6.14 | 460 | 1 | m.p.: 133.5° C. (DSC) |
| 163 | 5.15 | 442 | 1 | m.p.: 201.5° C. (DSC) |
| 164 | 5.97 | 457 | 1 | m.p.: 122.0° C. (DSC) |
| 165 | 1.20 | 434 | 5 | |
| 166 | 5.16 | 442 | 1 | m.p.: 277.5° C. (DSC) |
| 167 | 6.41 | 470 | 1 | m.p.: 137.7° C. (DSC) |
| 168 | 5.95 | 458 | 2 | m.p.: 166.2° C. (DSC) |
| 170 | 1.02 | 444 | 3 | m.p.: 156.0° C. (Kofler) |
| 171 | 4.86 | 477 | 1 | |
| 172 | 5.73 | 619 | 1 | |

TABLE F-4

Analytical data - Retention time ($R_t$ in minutes), $(MH)^-$ peak, LCMS procedure and physico-chemical data (m.p. is defined as melting point).

| Co. No. | $R_t$ | $(MH)^-$ | Procedure | Physico-chemical data |
|---|---|---|---|---|
| 1 | 0.83 | 428 | 3 | |
| 2 | 0.74 | 412 | 3 | |
| 8 | 4.10 | 428 | 4 | m.p.: >300° C. (Kofler) |
| 97 | 4.89 | 510 | 4 | m.p.: 152.9° C. (DSC) |
| 9 | 6.16 | 456 | 1 | m.p.: 174° C. (Kofler) |
| 25 | 5.05 | 430 | 4 | m.p.: 171.3° C. (DSC) |

C. Pharmacological Examples

C.1 Inhibition of cAMP in Response to Activation of the Human CB1 and CB2 Receptors Functional activity of the test compounds was assessed by measuring their potency to inhibit forskolin-activated cAMP production upon activation of the human CB1 (hCB1) or human CB2 (hCB2) receptor through homogenous time resolved fluorescence (HTRF) assays.

CHO—K1 cells stably transfected with either hCB1 or hCB2 were grown up to 80-90% confluence in T175 Falcon flasks in DMEM/NUT MIX F-12 culture medium complemented with 2% Solution A ($5.10^6$ IU/l penicillin G, 5g/l streptomycin sulphate, 5.5 g/l pyruvate, 14.6 g/l L-glutamine, 1M NaOH) and 10% foetal calf serum. Before the experiments, medium was removed, cells were washed with PBS/EDTA (140 mM NaCl, 1 mM Na$_2$-EDTA, 8 mM Na$_2$HPO$_4$.2H$_2$O, 8.5 mM KH$_2$PO$_4$, 2.7 mM KCl, 21 mM glucose), resuspended in stimulation buffer (HBSS 1×, IBMX 1 mM, Hepes 5 mM, MgCl2 10 mM, BSA 0.1%, pH 7.4). Cells were diluted to a concentration of $8.10^5$ cell/ml for hCB1 experiments and $10^6$ cells/ml for hCB2 experiments. Assays were performed using the cAMP Dynamic HTRF kit (CIS bio international, France) according to the recommendations of the manufacturer.

For CB1, each well of a 96 flat bottom black polystyrene assay plate (Costar) was filled with 25 μl stimulation buffer containing 6 μM forskolin and either test compound (in 2% DMSO), 2% DMSO or 2 μM CP55490 (in 2% DMSO). Then, 25 μl of the diluted cells was added (20,000 cells/well). After 30 minutes incubation in dark at room temperature, 25 μl cAMP-XL665 and 25 μl anti-cAMP cryptate (both at a final dilution of 1/80) was added to the cells.

For CB2, each well of a 384 flat bottom black polystyrene assay plate (Costar) was filled with 10 μl stimulation buffer containing 15 μM forskolin and either test compound (in 3% DMSO), 3% DMSO or 10 μM Win55212-2 (in 3% DMSO). Then, 20 μl of the diluted hCB2-CHO—K1 cells was added (20,000 cells/well). After 30 minutes incubation in dark at room temperature, 10 μl cAMP-XL665 and 10 μl anti-cAMP cryptate (both at a final dilution of 1/100) was added to the cells.

After equilibration of the reaction mixtures for 1 to 24 hours in dark at room temperature, fluorescence was measured at 665 nm and 620 nm using a Discovery microplate fluorescence counter (Perkin Elmer), and the signal ratio of 665 nm /620 nm was calculated. The signal ratios of the test compounds were expressed relative to the signal ratios of the DMSO control (maximal signal ratio, no inhibition of cAMP) and CP55490 or WIN55212-2 for hCB1 and hCB2, respectively (minimal signal ratio, maximal inhibition of cAMP). From the dose response curves generated for each test compound, the dose at which 50% of the maximal inhibition of cAMP level is observed (EC$_{50}$, expressed in the Tables as pEC$_{50}$=−log(EC$_{50}$) values) and the level of inhibition reached with 10 μM of the test compound compared to CP55490 (for hCB1) or WIN55212-2 (for hCB2) was calculated.

TABLE C-1 pEC50 values for CB-1 and CB-2 agonism

| Co. No. | CB2 pEC50 | CB1 pEC50 | ratio CB2 agonism over CB1 agonism |
|---|---|---|---|
| 1 | 8.30 | <5 | >1995 |
| 2 | 7.42 | <5 | >263 |
| 3 | 8.76 | 6.16 | 398 |
| 4 | 8.72 | 5.49 | 1679 |
| 5 | 9.43 | 6.59 | 676 |
| 7 | 8.74 | <5 | >5495 |
| 8 | 8.51 | 5.33 | 1514 |
| 9 | 9.48 | 5.85 | 4266 |
| 10 | 9.13 | 5.02 | 12883 |
| 11 | 8.90 | 7.22 | 48 |
| 12 | 8.81 | 6.33 | 302 |
| 13 | 8.90 | 5.69 | 1622 |
| 14 | 9.11 | 5.42 | 4898 |
| 15 | 8.98 | 6.24 | 556 |
| 16 | 8.63 | 6.07 | 359 |
| 17 | 8.80 | 5.03 | 5821 |
| 18 | 9.17 | 6.20 | 933 |
| 19 | 8.95 | 6.14 | 638 |
| 20 | 8.90 | 6.36 | 347 |
| 21 | 8.42 | 5.00 | 2630 |
| 22 | 8.95 | 5.70 | 1758 |
| 23 | 8.99 | 6.39 | 398 |
| 24 | 8.66 | 6.05 | 407 |
| 25 | 9.09 | 6.39 | 495 |
| 26 | 9.10 | 6.27 | 676 |
| 27 | 9.15 | <5 | >14125 |
| 28 | 8.54 | <5 | >3467 |
| 29 | 8.50 | 5.88 | 417 |
| 30 | 8.77 | 5.28 | 3055 |
| 31 | 8.92 | 6.37 | 353 |
| 32 | 8.59 | 5.12 | 2951 |
| 33 | 8.51 | 5.24 | 1884 |
| 34 | 8.80 | 5.13 | 4732 |
| 35 | 9.39 | 7.49 | 79 |
| 36 | 9.17 | 7.14 | 108 |
| 37 | 9.03 | <5.00 | >10839 |
| 38 | 8.56 | <5.00 | >3631 |
| 39 | 8.77 | 5.69 | 1216 |
| 40 | 8.97 | 6.68 | 193 |
| 42 | 9.20 | 6.97 | 168 |
| 42 | 8.40 | <5.00 | >2512 |
| 43 | 9.00 | 5.79 | 1622 |
| 44 | 8.70 | 6.90 | 64 |
| 45 | 8.52 | <5.00 | >3311 |
| 46 | 8.98 | 5.41 | 3758 |
| 47 | 8.77 | 5.83 | 871 |
| 48 | 9.24 | 6.70 | 347 |
| 49 | 8.33 | <5.00 | >2138 |
| 50 | 9.16 | 5.35 | 6457 |
| 51 | 8.91 | 7.05 | 73 |
| 52 | 9.16 | 6.64 | 331 |
| 53 | 8.43 | 5.65 | 607 |
| 54 | 9.03 | 6.91 | 133 |
| 55 | 8.64 | 6.08 | 363 |
| 56 | 8.58 | <5.00 | >3802 |
| 57 | 8.96 | 5.84 | 1328 |
| 58 | 9.08 | 5.74 | 2188 |
| 59 | 8.95 | 5.64 | 2018 |
| 60 | 8.98 | 6.18 | 638 |
| 61 | 8.95 | 6.82 | 135 |
| 62 | 9.23 | 5.71 | 3299 |
| 63 | 9.01 | 5.55 | 2818 |
| 64 | 9.32 | 5.73 | 3920 |
| 65 | 8.53 | <5.00 | >3388 |
| 66 | 7.83 | <5.00 | >676 |
| 67 | 8.37 | <5.00 | >2344 |
| 68 | 8.51 | 6.44 | 116 |
| 69 | 8.76 | 6.16 | 398 |
| 70 | 9.26 | 5.85 | 2570 |
| 71 | 9.13 | <5.00 | >13490 |
| 72 | 9.17 | 5.99 | 1525 |
| 73 | 8.86 | 6.93 | 84 |
| 74 | 8.50 | 5.68 | 668 |
| 75 | 8.38 | 5.02 | 2291 |
| 76 | 7.92 | <5.00 | >832 |
| 77 | 8.71 | 5.59 | 1303 |
| 78 | 8.14 | <5.00 | >1380 |
| 79 | 8.53 | 5.80 | 543 |
| 80 | 8.38 | 4.98 | 2483 |
| 81 | 9.30 | 5.97 | 2138 |
| 82 | 8.41 | 5.80 | 407 |
| 83 | 8.70 | 6.39 | 209 |
| 84 | 8.90 | 6.21 | 490 |
| 85 | 9.03 | 6.08 | 891 |
| 86 | 7.92 | <5.00 | >832 |
| 87 | 8.67 | 5.64 | 1072 |
| 88 | 8.63 | 5.90 | 537 |
| 89 | 7.95 | <5.00 | >891 |
| 90 | 8.57 | <5.00 | >3715 |
| 91 | 8.30 | 5.00 | 1995 |
| 92 | 8.16 | 5.53 | 437 |
| 93 | 8.83 | <5.00 | >6761 |
| 94 | 8.60 | 5.57 | 1059 |
| 95 | 8.24 | <5.00 | >1738 |
| 96 | 8.70 | <5.00 | >5012 |
| 97 | 8.73 | 5.41 | 2065 |
| 98 | 9.02 | 6.13 | 794 |
| 99 | 8.88 | 6.03 | 700 |
| 100 | 8.80 | 6.00 | 631 |
| 101 | 8.60 | 6.83 | 58 |
| 102 | 8.30 | 5.04 | 1820 |
| 103 | 8.15 | 5.68 | 295 |
| 104 | 9.13 | 7.06 | 117 |
| 105 | 8.80 | 6.32 | 295 |
| 106 | 9.14 | 6.50 | 432 |
| 107 | 8.62 | 5.81 | 646 |
| 108 | 8.59 | <5.00 | >3890 |
| 109 | 9.09 | 6.58 | 324 |
| 110 | 9.26 | 5.98 | 1905 |
| 111 | 8.94 | 6.37 | 372 |
| 112 | 8.31 | <5.00 | >2030 |
| 113 | 8.58 | 6.10 | 302 |
| 115 | 8.43 | 5.44 | 977 |
| 116 | 8.23 | 5.24 | 966 |
| 117 | 8.35 | 6.01 | 219 |
| 118 | 8.75 | 6.11 | 437 |
| 119 | 8.15 | <5.00 | >1413 |
| 120 | 8.64 | <5.00 | >4365 |
| 121 | 8.51 | 5.55 | 912 |
| 122 | 9.01 | 7.00 | 102 |
| 123 | 8.38 | <5.00 | >2399 |
| 124 | 7.84 | <5.00 | >692 |
| 125 | 8.60 | <5.00 | >3981 |
| 126 | 9.07 | 6.02 | 1129 |
| 127 | 8.78 | <5.00 | 6026 |
| 128 | 8.68 | <5.00 | >4786 |
| 129 | 7.81 | 5.02 | 617 |
| 130 | 8.64 | <5.00 | >4315 |
| 131 | 7.80 | <5.00 | >631 |
| 132 | 8.85 | <5.00 | >7079 |
| 133 | 8.40 | <5.00 | >2512 |
| 134 | 8.86 | 5.42 | 2786 |
| 135 | 8.66 | <5.00 | >4571 |
| 136 | 9.36 | <5.00 | >22734 |
| 137 | 8.95 | 6.11 | 687 |
| 138 | 8.76 | 6.08 | 473 |
| 139 | 7.88 | <5.00 | >759 |
| 141 | 8.25 | <5.00 | >1792 |
| 142 | 9.02 | 5.87 | 1413 |
| 143 | 7.77 | <5.00 | >589 |
| 144 | 8.49 | <5.00 | >3090 |
| 145 | 8.49 | <5.00 | >3090 |
| 146 | 8.60 | <5.00 | >3981 |
| 147 | 9.02 | <5.00 | >10471 |
| 148 | 9.59 | <5.00 | >38905 |
| 149 | 8.90 | <5.00 | >8035 |

TABLE C-1-continued pEC50 values for CB-1 and CB-2 agonism

| Co. No. | CB2 pEC50 | CB1 pEC50 | ratio CB2 agonism over CB1 agonism |
|---|---|---|---|
| 150 | 8.90 | 6.09 | 638 |
| 151 | 9.32 | 5.41 | 8035 |
| 152 | 8.93 | 5.44 | 3090 |
| 153 | 9.07 | <5.00 | >11749 |
| 154 | 8.95 | <5.00 | >9016 |
| 155 | 8.60 | <5.00 | >3951 |
| 156 | 8.39 | 5.60 | 617 |
| 157 | 8.46 | <5.00 | >2884 |
| 158 | 8.85 | 5.08 | 5888 |
| 159 | 8.67 | <5.00 | >4677 |
| 160 | 8.37 | <5.00 | >2344 |
| 161 | 8.74 | 5.28 | 2951 |
| 162 | 9.44 | <5.00 | >27542 |
| 165 | 7.97 | <5.00 | >923 |
| 168 | 8.09 | <5.00 | >1230 |

C.2 Compative Data

Table C.2 lists a number of sulfonyl benzimidazole derivatives bearing an unsubstituted heterocyclic moiety on the sulfonyl group. These compounds are covered by reference WO-2006/048754.

TABLE C-2

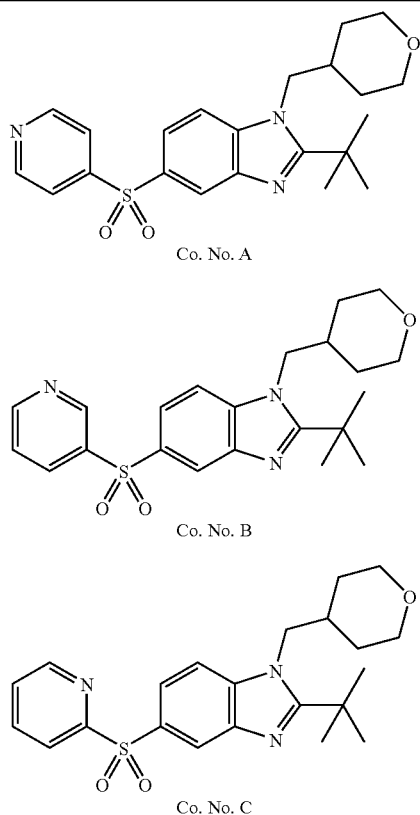

Co. No. A

Co. No. B

Co. No. C

Co. No. D

Co. No. E

The ratio of CB2 agonism over CB1 agonism of the compounds A to E was measured using the same procedures as described in Pharmacological Example C.1. Table C-3 lists the ratio of CB2 over CB1 in comparison with the ratio of CB2 over CB1 for the compounds of formula (I) that structurally differ by the presence of a substituent on the heterocyclic moiety on the sulfonyl group.

TABLE C-3 comparison between art compounds A to E and compounds of the present invention

| Co. No. | ratio CB2 over CB1 agonism | Co. No. | ratio CB2 over CB1 agonism |
|---|---|---|---|
| A | 215 | 3 | 398 |
|   | 215 | 8 | 1514 |
|   | 215 | 9 | 4266 |
|   | 215 | 14 | 4898 |
|   | 215 | 17 | 5821 |
|   | 215 | 19 | 638 |
|   | 215 | 21 | 2630 |
|   | 215 | 22 | 1758 |
|   | 215 | 23 | 398 |
|   | 215 | 25 | 495 |
| B | 30 | 1 | 1995 |
|   | 30 | 28 | 3467 |
| C | 36 | 4 | 1679 |
|   | 36 | 10 | 12883 |
| D | 26 | 12 | 302 |
|   | 26 | 20 | 346 |
| E | 219 | 24 | 407 |

The compounds of the present invention are more selective CB2 agonists than the art compounds A to E.

The invention claimed is:
1. Compound of formula (I)

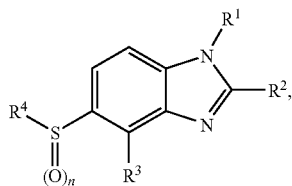

the pharmaceutically acceptable acid addition salts and the stereochemically isomeric forms thereof, wherein
n is an integer 1 or 2;
$R^1$ is $C_{2-6}$alkyl;
  $C_{1-6}$akyl substituted with 1, 2 or 3 substituents each independently selected from halo, hydroxy, $C_{1-4}$akyl, $C_{1-4}$alkyloxy, cyano, nitro, amino, and mono- or di($C_{1-4}$ alkyl)amino;
  $C_{1-6}$alkyl substituted with a cyclic group selected from $C_{3-8}$cycloalkyl, oxo$C_{3-8}$cycloalkyl, $C_{5-8}$cycloalkenyl, bicycle[2.2.1]hept-2-enyl, bicyclo[2.2.1]octanyl and bicycle[3.1.1]heptanyl, wherein said cyclic group is optionally substituted with one or more substituents each independently selected from halo, hydroxy, $C_{1-4}$alkyl, $C_{1-4}$alkyloxy, cyano, nitro, $NR^5R^6$ or $CONR^5R^6$ wherein $R^5$ and $R^6$ are independently selected from hydrogen or $C_{1-4}$alkyl; or
  $C_{1-6}$alkyl substituted with a heterocycle selected from pyrrolidinyl, piperidinyl, homopiperidinyl, piperazinyl, morpholinyl, tetrahydrofuranyl, tetrahydropyranyl, 1,1-dioxo-tetrahydro-thiopyranyl, [1,3]dioxolanyl, [1,4]dioxolanyl, [1,3]dioxanyl, 5-oxo-pyrrolidin-2-yl, or 2-oxo-oxepanyl;
    wherein said heterocycle is optionally substituted with one or two substituents each independently selected from $C_{1-4}$alkyl, polyhalo$C_{1-4}$alkyl, halo, hydroxy, $C_{1-4}$alkyloxy, cyano, trifluoromethyl, $COR^5$, $COOR^5$, $CONR^5R^6$, $SO_2R^5$ wherein $R^5$ and $R^6$ are independently selected from hydrogen or $C_{1-4}$alkyl or polyhalo$C_{1-4}$alkyl;
$R^2$ is $C_{2-6}$alkyl;
  $C_{1-6}$alkyl substituted with 1, 2 or 3 substituents each independently selected from halo, hydroxy, $C_{1-4}$alkyl, $C_{3-6}$cycloalkyl, $C_{1-4}$alkyloxy, polyhalo $C_{1-4}$alkyloxy, trifluoromethyl, cyano, nitro, $NR^7R^8$, $CONR^7R^8$, or $NHCOR^7$ wherein $R^7$ and $R^8$ are independently selected from hydrogen, $C_{1-4}$alkyl or polyhalo$C_{1-4}$alkyl;
  $C_{3-6}$alkenyl;
  $C_{3-6}$alkynyl;
  $C_{3-6}$cycloalkyl; or
  cyclic group selected from pyrrolidininyl, piperidinyl, piperazinyl, morpholinyl, tetrahydrofuranyl, tetrahydropyranyl, [1,3]dioxolanyl, [1,3]dioxanyl, [1,4]dioxanyl, 5-oxo-pyrrolidin-2-yl, bicycle[2.2.1]hept-2-enyl, and bicycle[3.1.1]heptanyl; wherein said cyclic group is optionally substituted with one or two substituents each independently selected from $C_{1-4}$alkyl, halo, hydroxy, $C_{1-4}$alkyloxy, or trifluoromethyl;
$R^3$ is hydrogen, halo, $C_{1-4}$alkyl, $C_{1-4}$alkyloxy, trifluoromethyl or cyano;
$R^4$ is heteroaryl;
  heteroaryl is selected from N-oxy-pyridinyl, N-oxy-pyridazinyl, N-oxy-pyrimidinyl or N-oxy-pyrazinyl; or
  selected from furanyl, thiophenyl, pyrrolyl, pyrazolyl, imidazolyl, isoxazolyl, thiazolyl, triazolyl, tetrazolyl, isothiazolyl, thiadiazolyl, oxadiazolyl, pyridinyl, pyridazinyl, pyrimidinyl, pyrazinyl, triazinyl, N-oxy-pyridinyl, N-oxy-pyridazinyl, N-oxy-pyrimidinyl, N-oxy-pyrazinyl or 2-oxo-1,2-dihydro-pyridinyl, each substituted with 1, 2 or 3 substituents each independently selected from halo; hydroxy; $C_{1-4}$alkyl; $C_{3-6}$cycloalkyl; $C_{2-6}$alkenyl; $C_{2-6}$alkenyl substituted with 1 or 2 substituents selected from halo; $C_{2-6}$alkynyl; $C_{2-6}$alkynyl substituted with $C_{1-4}$alkyloxy; $C_{1-4}$alkyloxy; $C_{1-4}$alkyloxy$C_{1-4}$alkyl; polyhalo $C_{1-4}$alkyl; polyhalo$C_{1-4}$alkyloxy; cyano; nitro; $NR^9R^{10}$; $R^{11}$-carbonyl; $R^{11}$—$SO_2$—; $C_{1-4}$alkyl substituted with hydroxy, $NR^9R^{10}$, $R^{11}$-carbonyl or $R^{11}$—$SO_2$—; oxadiazolyl optionally substituted with $C_{1-4}$alkyl, polyhalo$C_{1-4}$alkyl or $C_{3-6}$cycloalkyl; or dioxolanyl optionally substituted with 1 or 2 $C_{1-4}$alkyl; $C_{1-4}$alkyloxy substituted with hydroxy, $C_{1-4}$alkyloxy, $C_{1-4}$alkylcarbonylamino, $C_{1-4}$alkyloxycarbonylamino, amino, di($C_{1-4}$akyl)amino or morpholinyl; $C_{1-4}$alkylcarbonylamino$C_{1-4}$alkylamino; $C_{1-4}$alkyloxy$C_{1-4}$alkylamino;
  wherein $R^9$ and $R^{10}$ are independently from another selected from hydrogen, $C_{1-4}$alkyl, polyhalo $C_{1-4}$alkyl, aminosulfonyl, or $C_{1-8}$alkylsulfonyl; or $R^{11}$-carbonyl;
  wherein $R^9$ and $R^{10}$ are taken together with the nitrogen atom bearing $R^9$ and $R^{10}$ may form a pyrrolidinyl, piperidinyl, piperazinyl or morpholinyl ring; and
  wherein $R^{11}$ is $C_{1-4}$alkyl, $C_{1-4}$alkyloxy, hydroxy, amino, mono- or di-($C_{1-4}$alkyl)amino, (hydroxy$C_{1-4}$alkyl) amino, ($C_{1-4}$alkyloxy$C_{1-4}$alkyl)amino, di($C_{1-4}$alkyl) amino$C_{1-4}$alkyl, pyrrolidinyl, piperidinyl, morpholinyl, N-methyl-piperazinyl, or $C_{1-4}$alkyl substituted with hydroxy, $C_{1-4}$alkyloxy, trifluoromethyl, $C_{1-4}$alkyloxy$C_{1-4}$alkyl, pyrrolidinyl, piperidinyl, morpholinyl, N-methyl-piperazinyl, or 2-oxo-imidazolidin-1-yl.

2. A compound as claimed in claim 1 wherein n is 2.
3. A compound as claimed in claim 1 wherein $R^1$ is $C_{1-6}$alkyl substituted with a cyclic group selected from $C_{3-8}$cycloalkyl or tetrahydropyranyl.
4. A compound as claimed in claim 1 wherein $R^2$ is $C_{1-6}$alkyl.
5. A compound as claimed in claim 1 wherein $R^4$ is N-oxy-pyridinyl.
6. A compound as claimed in claim 1 wherein $R^4$ is $R^4$ is furanyl, thiophenyl, oxadiazolyl, pyridinyl, or pyridazinyl; each substituted with 1, 2 or 3 substituents each independently selected from halo; hydroxy; $C_{1-4}$alkyl; $C_{1-4}$alkyloxy; polyhalo$C_{1-4}$alkyl; polyhalo$C_{1-4}$alkyloxy; cyano; $NR^9R^{10}$; $R^{11}$-carbonyl; $R^{11}$—$SO_2$—; or oxadiazolyl optionally substituted with $C_{1-4}$alkyl; wherein $R^9$ and $R^{10}$ are independently from another selected from hydrogen or $R^{11}$-carbonyl; and wherein $R^{11}$ is $C_{1-4}$ alkyl, amino, or morpholinyl.

7. A pharmaceutical composition comprising a pharmaceutically acceptable carrier and a therapeutically active amount of a compound as claimed in claim 1.
8. A process for preparing a pharmaceutical composition as claimed in claim 7 wherein a therapeutically active amount of a compound as claimed in claim 1 is intimately mixed with a pharmaceutically acceptable carrier.
9. A process for preparing a compound of formula (I-a), defined as a compound of formula (I) as claimed in claim 1 wherein n is 1, by S-oxidizing an intermediate (A), wherein $R^1$, $R^2$, $R^3$ and $R^4$ are as defined in claim 1, with an oxidizing agent such as, $NaIO_4$, tert-butyloxychloride, acyl nitrites, sodium perborate and peracids such as meta-chloroperbenzoic acid

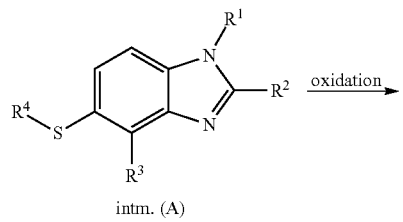

intm. (A)

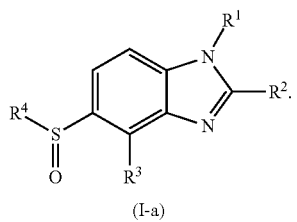

(I-a)

10. A process for preparing a compound of formula (I-b), defined as a compound of formula (I) as claimed in claim 1 wherein n is 2, by S-oxidizing an intermediate (A), wherein $R^1$, $R^2$, $R^3$ and $R^4$ are as defined in claim 1, with an oxidizing agent such as, $NaIO_4$, tert-butyloxychloride, acyl nitrites, sodium perborate and peracids such as meta-chloroperbenzoic acid

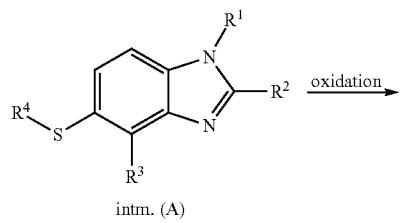

intm. (A)

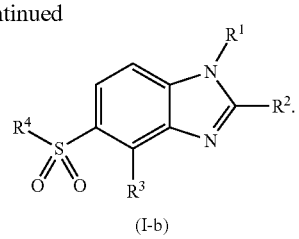

(I-b)

11. A process for preparing a compound of formula (I-b), defined as a compound of formula (I) as claimed in claim 1 wherein n is 2, by subjecting an intermediate of formula (XIII), wherein $R^1$, $R^2$, $R^3$ and $R^4$ are as defined in claim 1, to a condensation reaction under acidic or basic conditions

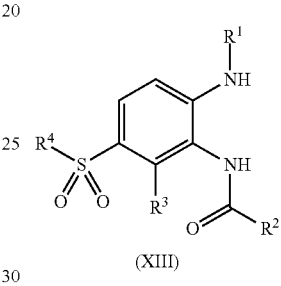

(XIII)

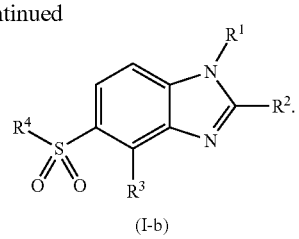

(I-b)

* * * * *